United States Patent
Chillon Rodriguez et al.

(10) Patent No.: US 12,036,268 B2
(45) Date of Patent: Jul. 16, 2024

(54) SECRETED SPLICING VARIANT OF MAMMAL KLOTHO AS A MEDICAMENT FOR COGNITION AND BEHAVIOUR IMPAIRMENTS

(71) Applicants: UNIVERSITAT AUTONOMA DE BARCELONA, Bellatera (ES); FUNDACIÓ INSTITUCIÓ CATALÀ DE RECERCA I ESTUDIS AVANçATS, Barcelona (ES)

(72) Inventors: Miguel Chillon Rodriguez, Barcelona (ES); Anna Masso Chacon, Vilanova i la Geltrú (ES); Assumpció Bosch Merino, Sant Cugat del Vallès (ES)

(73) Assignees: Universitat Autònoma De Barcelona, Barcelona (ES); Fundació Institució Català de Recerca i Estudis Avançats, Barcelona (ES)

( * ) Notice: Subject to any disclaimer, the term of this patent is extended or adjusted under 35 U.S.C. 154(b) by 593 days.

(21) Appl. No.: 15/777,456

(22) PCT Filed: Nov. 21, 2016

(86) PCT No.: PCT/EP2016/078320
§ 371 (c)(1),
(2) Date: May 18, 2018

(87) PCT Pub. No.: WO2017/085317
PCT Pub. Date: May 26, 2017

(65) Prior Publication Data
US 2019/0030138 A1 Jan. 31, 2019

(30) Foreign Application Priority Data
Nov. 19, 2015 (EP) .................... 15195470

(51) Int. Cl.
*A61K 38/47* (2006.01)
*A61K 9/00* (2006.01)
(Continued)

(52) U.S. Cl.
CPC ............ *A61K 38/47* (2013.01); *A61K 9/0085* (2013.01); *A61K 45/06* (2013.01); *A61P 25/28* (2018.01);
(Continued)

(58) Field of Classification Search
CPC ...... A61K 38/47; A61K 9/0085; A61K 45/06; A61K 48/00; A61P 25/28; C07K 16/40; C12N 9/2402; C12Y 302/01031
See application file for complete search history.

(56) References Cited

U.S. PATENT DOCUMENTS

| | | | |
|---|---|---|---|
| 2010/0130594 A1* | 5/2010 | Barkats | A61P 25/00 514/44 R |
| 2012/0177605 A1* | 7/2012 | Kaspar | A61K 48/005 435/320.1 |
| 2016/0120959 A1* | 5/2016 | Sun | A61K 38/47 424/93.2 |

FOREIGN PATENT DOCUMENTS

| | | | |
|---|---|---|---|
| JP | 2001072607 A * | 3/2001 | ............ A61K 48/00 |
| WO | WO 2008/135993 A1 | 11/2008 | |

(Continued)

OTHER PUBLICATIONS

Dubal (Cell Reports, 7: 1065-1076, 2014 (Year: 2014).*
(Continued)

*Primary Examiner* — Anoop K Singh
*Assistant Examiner* — Suzanne E Ziska
(74) *Attorney, Agent, or Firm* — Shawn P. Foley; Gabriel L. Hendricks

(57) ABSTRACT

The invention discloses using secreted splicing variant of mammal Klotho (s-KL) as an agent for the prevention and/or
(Continued)

treatment of cognitive and/or behaviour impairments. It also refers to gene constructs and expression vectors useful in gene therapy for the delivery of said s-KL variant to the central nervous system of a mammal, in particular a rodent or a human. Pharmaceutical compositions comprising either the protein s-KL or any gene construct for expressing the protein in the CNS are also disclosed.

32 Claims, 12 Drawing Sheets

Specification includes a Sequence Listing.

(51) Int. Cl.
      A61K 45/06      (2006.01)
      A61K 48/00      (2006.01)
      A61P 25/28      (2006.01)
      C07K 16/40      (2006.01)
      C12N 9/24       (2006.01)
(52) U.S. Cl.
     CPC ............ *C07K 16/40* (2013.01); *C12N 9/2402* (2013.01); *C12Y 302/01031* (2013.01); *A61K 48/00* (2013.01); *C12N 2710/10043* (2013.01)

(56) References Cited

FOREIGN PATENT DOCUMENTS

| WO | WO 2014/152993 | A1 | 9/2014 | |
|---|---|---|---|---|
| WO | WO 2016/127097 | A1 | 8/2016 | |
| WO | WO-2016127097 | A1 * | 8/2016 | .............. A61P 25/28 |
| WO | WO 2016/135295 | A1 | 9/2016 | |

OTHER PUBLICATIONS

Kuang, (Neurobiology of Aging, 35: 169-178, 2014). (Year: 2014).*
Seignourel (Clin Psychol Rev, 28(7): 1071-1072, 2008). (Year: 2008).*
Menche (JCI Insight, 2(20): e94375, 2017) (Year: 2017).*
Borges (Molecular and Clinical Oncology 16: 93, 2022) (Year: 2022).*
Kuro-o (Pflugers Arch—Eur J Physiol, 459: 333-343, 2010) (Year: 2010).*
JP2001072607-A (JP607) (English language machine translation) (Year: 2001).*
Nooyens et al ("Type 2 Diabetes and Cognitive Decline in Middle-Aged Men and Women," Diabetes Care, vol. 33, No. 9, Sep. 2010) (Year: 2010).*
McLean et al ("Widespread neuron-specific transgene expression in brain and spinal cord following synapsin promoter-driven AAV9 neonatal intracerebroventricular injection," Neuro-science Letters 576 (2014) 73-77) . (Year: 2014).*
Sang et al ("Dextromethorphan and Memantine in Painful Diabetic Neuropathy and Postherpetic Neuralgia: Efficacy and Dose-Response Trials," Anesthesiology 2002; 96:1053-61) (Year: 2022).*
Ristow et al ("Neurodegenerative disorders associated with diabetes mellitus," J Mol Med (2004) 82:510-529) (Year: 2004).*
Nelson et al ("Human cerebral neuropathology of Type 2 diabetes mellitus," Biochimica et Biophysica Acta 1792 (2009) 454-469) (Year: 2009).*
Smith et al ("Association of diabetes with anxiety: A systematic review and meta-analysis," Journal of Psychosomatic Research 74 (2013) 89-99). (Year: 2013).*
Chen et al (Rosiglitazone Increases Cerebral Klotho Expression to Reverse Baroreflex in Type 1-Like Diabetic Rats, BioMed Research International vol. 2014, Article ID 309151, 9 pages, published Feb. 13, 2014). (Year: 2014).*
Arvanitakis et al ("Diabetes Mellitus, dementia and cognitive function in older persons," The Journal of Nutrition, Health & Aging; Jul./Aug. 2006; 10, 4). (Year: 2006).*
Altschul et al., "Gapped BLAST and PSI-BLAST: a new generation of protein database search programs", Nucleic Acids Research, 25(17): 3389-3402 (1997).
Dubal et al., "Life Extension Klotho Enhances Cognition", Cell Reports, 7(1-12) (2014).
Forster et al., "Vitamin D Receptor Controls Expression of the Anti-aging Klotho Gene in Mouse and Human Renal Cells", Biochem Biophys Res Commun., 414(3): 557-562 (2011).
Hirt et al., "Selective Extraction of Polyoma DNA from Infected Mouse Cell Cultures", J Mol. Biol., (26): 365-369 (1967).
Imura et al., "Secreted Klotho protein in sera and CSF: implication for post-translational cleavage in release of Klotho protein from cell membrane", FEBS Letters, (565): 143-147 (2004).
Kuang et al., "Klotho upregulation contributes to the neuroprotection of ligustilide in an Alzheimer's disease mouse model", Neurobiology of Aging, (35): 1-10 (2014).
Kuro-o, et al., "Mutation of the mouse klotho gene leads to a syndrome resembling ageing", Nature, (390): 45-51 (1997).
Kurosu, et al., "Regulation of Fibroblast Growth Factor-23 Signaling by Klotho", J. Biol. Chem., 281(10): 6120-6123 (2006).
Massó et al., "Secreted and Transmembrane [alpha] Klotho Isoforms Have Different Spatio-Temporal Profiles in the Brain during Aging and Alzheimer's Disease Progression", PLOS ONE, 10(11): 1-15 (2015).
Matsumura et al., "Identification of the Human Klotho Gene and Its Two Transcripts Encoding Membrane and Secreted Klotho Protein", Biochem Biophys Res Commun., (242): 626-630 (1998).
Shiraki-Iida et al., "Structure of the mouse klotho gene and its two transcripts encoding membrane and secreted protein", FEBS Letters, (424): 6-10 (1998).
Wang et al, "Current understanding of klotho", Ageing Res. Rev., (8): 43-51 (2009).
Deary et al., "KLOTHO genotype and cognitive ability in childhood and old age in the same individuals", Neuroscience etters, 378: 22-27 (2005).
Dubal et al., "Life Extension Factor Klotho Prevents Mortality and Enhances Cognition in hAPP Transgenic Mice", The Journal of Neuroscience, 35(6): 2358-2371 (2015).
Piedra et al., "Development of a Rapid, Robust, and Universal PicoGreen-Based Method to Titer Adeno-Associated Vectors", Human Gene Therapy Methods, 26: 35-42 (2015).
Lentz et al., "Viral Vectors for Gene Delivery to the Central Nervous System," Neurobiol Dis., 48(2): 179-188, DOI:10.1016/j.nbd.2011.09.014 (Nov. 2012).
Wang and Su, "Current understanding of klotho," Ageing Res. Rev., 8(1):43-51, DOI:10.1016/j.arr.2008.10.002 (Jan. 2009).
Letter dated May 30, 2021 from Dr. Carmela R. Abraham of Boston University School of Medicine, Department of Biochemistry.
Mencke, et al: "Human alternative Klotho mRNA is a nonsense-mediated mRNA decay target inefficiently spliced in renal disease", JCI Insight; Oct. 19, 2017; vol. 2(20); e94375.

* cited by examiner (A)

(B)

(A)

(B)

(A)

(B)

(A)

(B)

(C)
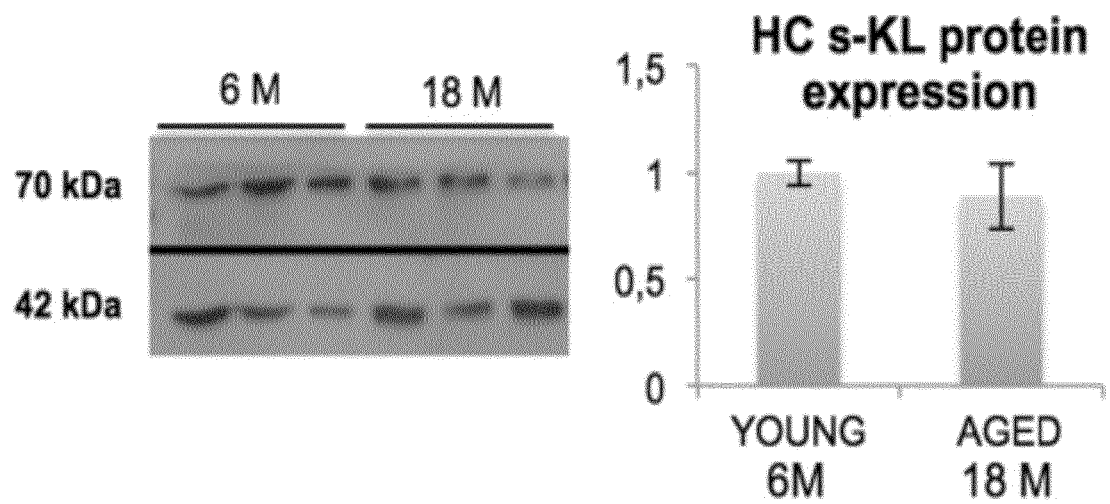
(D)
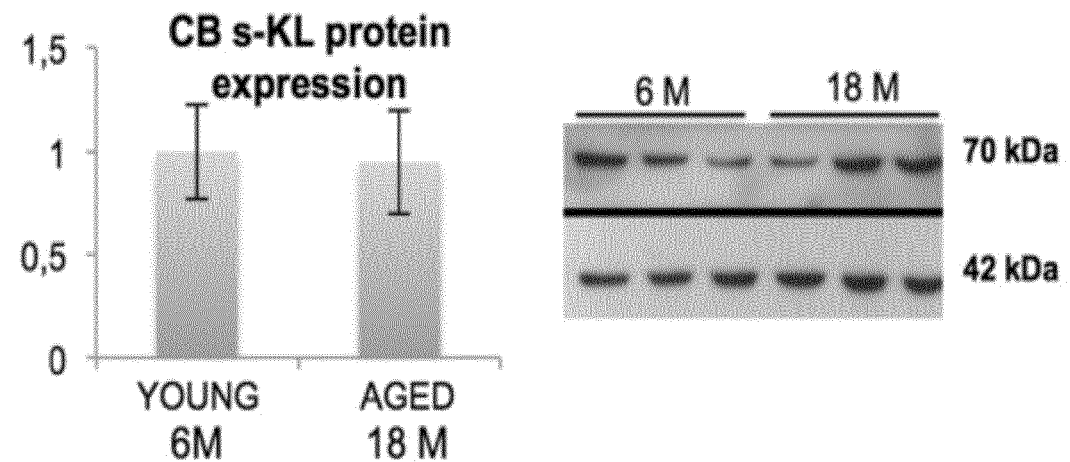
Cont. FIG. 10

SECRETED SPLICING VARIANT OF MAMMAL KLOTHO AS A MEDICAMENT FOR COGNITION AND BEHAVIOUR IMPAIRMENTS

CROSS-REFERENCE TO RELATED APPLICATIONS

This application is a United States national stage filing under 35 U.S.C. § 371 of international (PCT) application no. PCT/EP2016/078320, filed Nov. 21, 2016, and designating the US, which claims priority to European patent application no. 15195470.8, filed Nov. 19, 2015.

The present invention relates to the field of medical approaches for preventing and/or treating cognition impairment and behaviour impairments in patients suffering from diseases related to memory loss, and to learning difficulties, and/or with neurodegenerative and/or neuropathological diseases.

BACKGROUND ART

It is widely known that memory is frequently lost along years and that some aspects can be changed leading to a loss of memory efficiency. Examples of these aspects include the difficulty of maintaining concentration to more than one thing at the same time; difficulties in learning new things that require an effort, and slow old information recuperation. Spoken abilities, information processing, problem resolution, working memory, long-term memory and spatial memory and ability are reduced with age, meanwhile expertise and cognitive abilities, such as semantic memory (vocabulary), world knowledge and implicit memory remain stable with age or even are bettered if no pathologies or neurodegeneration is present.

In connection with the neurodegenerative and/or neuropathological diseases, many of them related with aging, imply also cognitive impairments. Examples of these include Alzheimer's disease, Parkinson's disease, Huntington's disease, depression and schizophrenia.

In addition, with aging or in case of neurodegenerative and/or neuropathological diseases also behaviour impairments are observed, such as an increase in disorientation, anxiety episodes to unknown situations or places or even to the disorientation itself, as well as irrational fear.

All these cognitive and behaviour impairments are the major aim not only in the treatment of the symptomatology of many of the neurodegenerative and/or neuropathological diseases, but also in the prevention of cognition and behaviour problems during aging.

Among the several and complex mechanisms associated with memory loss during aging or in case of neuropathology or neurodegeneration, the role of the mammal protein Klotho has been studied.

In three independent human assays it was discovered that some mutations in klotho allele, namely the KL-VS klotho allele in vitro promoting an increase of klotho secretion, could get better results in cognitive tests in an independent manner of the age of the subjects. These data derive from the document of Deary et al., "Klotho genotype and cognitive ability in childhood and old age in the same individuals", *Neurosci Lett*—2005, vol. 378(1), pp. 22-27.

Klotho is a protein detected primarily in the distal convoluted tubule of the kidney, parathyroid hormone-secreting cells and choroid plexus epithelium of the brain. To a lesser extent α-klotho gene is also expressed in heart, skeletal muscle, urinary bladder, placenta, pancreas, testes, ovaries, colon and inner ear. Several studies in mice have revealed that the mutation of the single gene α-klotho on chromosome 13, induces a process of accelerated aging (See. Kuro-o, et al., Mutation of the mouse klotho gene leads to a syndrome resembling ageing. *Nature*—1997, vol. no. 390, pp.: 45-51; and Wang, Y. et al, "Current understanding of klotho", *Ageing Res Rev*—2009, vol. no. 8, pp.: 43-511) with mimicking typical symptoms such as atherosclerosis, osteoporosis/osteopenia, ectopic calcification in various tissues, emphysema, cognitive problems and infertility. Moreover, knockout α-klotho (kl$^-$/kl$^-$) mice showed dramatically reduced survival with prematurely around 2 months of age (Kuro-o, et al, supra). In contrast, transgenic mice overexpressing this gene had between 30 to 40% greater life expectancy. Similarly, several studies indicate that human klotho gene polymorphisms also affect the longevity and appearance of disorders associated with aging. In mice and humans, α-klotho gene encodes a transcript of a 5.2 kb. In the third exon there is an alternative splicing donor site that can generate two different transcripts: one encoding a transmembrane form (full transcript or full-length, 1014 amino acids) and the other a secreted form of the protein (half transmembrane transcript, 550 amino acids). The full-length transcript encodes a single pass transmembrane protein with a molecular weight of approximately 130 kDa (m-KL). The protein contains three domains: a short transmembrane domain at the C-terminal, an extracellular domain composed of two internal repeated sequences of about 550 amino acids called KL1 and KL2 respectively, and a very short intracellular domain of 10 amino acids. The transcript from alternative splicing generates a truncated form of the protein (s-KL) that is formed solely by the KL1 domain, with an approximate weight of 70 kDa. This alternative mRNA includes a specific secretion signal consisting of 15 amino acid tail that is not found in the m-KL transcript, and for this reason is also called the secreted isoform of klotho, s-KL, or the secreted splicing variant of klotho protein (See Matsumura et al., "Identification of the human klotho gene and its two transcripts encoding membrane and secreted Klotho protein", *Biochem Biophys Res Commun*—1998, vol. No. 242, pp.: 626-630). However, there is some controversy regarding this protein (s-KL) because it has not been detected in body fluids using antibodies. It has been specifically detected at mRNA levels, but not at protein level since the available antibodies cannot differentiate it from the KL1 domain cleaved from the transmembrane Klotho.

In addition, the extracellular domain of the transmembrane form can be cleaved by metalloproteinases ADAM10 and ADAM17 resulting in another form of soluble Klotho of about 130 kDa (abbreviated p-KL for proteolyzed membrane isoform), which has been detected in serum, urine, and cerebrospinal fluid. Moreover, two recent studies indicate that there is a second recognition site for the proteases ADAM10 and 17 located between the KL1 and KL2 domains, which generates two new 70 kDa isoforms, one contained the KL1 domain only (like the one generated from alternative splicing but without the specific amino acid tail), and the other one contained the KL2 domain. Thus, Klotho protein might enter the circulatory system through two main mechanisms: (a) from an alternative splicing (s-KL), and (b) by proteolytic cleavage mediated by ADAM 10 and 17. However, it is unknown the percentage that each of these events occurs.

With the aim of elucidating the role of Klotho as anti-aging factor and as agent improving learning and memory skills, systemically over-expressing Klotho transgenic mice have been obtained. Dubal et al. 2014 discloses that the variant of the human klotho gene KL-VS is associated with enhanced cognition in heterozygous carriers. This allele increased klotho levels in serum. Then they analyzed transgenic mice with global overexpression of full-length transmembrane klotho, performing better than controls in multiple tests of learning and memory (Dubal et al., "Life Extension Klotho Enhances Cognition", *Cell Reports*—2014, vol. 7, pp.: 1065-1076).

Another transgenic mouse also analyzed by Dubal et al., is particularly focused on Alzheimer's disease and it shows that elevating klotho expression decreases premature mortality, network dysfunction, cognitive deficits and behavioural abnormalities in human amyloid precursor protein (hAPP) transgenic mice, and all without altering the levels of hAPP (Dubal et al., Life Extension factor Klotho Prevents Mortality and Enhances Cognition in hAPP Transgenic Mice", *The Journal of Neuroscience*—2015, vol. 35/6, pp.: 2358-2371).

In said transgenic models it is likely evaluated the effect of the full-length transmembrane protein with a molecular weight of approximately 130 kDa (m-KL), and if any of the other isoforms are contributing to the effect, specially the processed Klotho (p-KL) isoform, this cannot be determined from the experimental procedure used by authors since current available detection systems are not capable of distinguishing among the different klotho isoforms. Although transgenic animals over-expressing a protein of interest may be good models for the analysis of its effects, they also imply the inconvenient of having this protein expressed ubiquitously (body and brain), and data may in addition be made up by the genetic background of the transgenic animal.

Another document showing the potential role of klotho in a mouse model of senescence (named SAMP8) is the one of Kuang et al., "Klotho upregulation contributes to the neuroprotection of ligustilide (LIG) in an Alzheimer's disease mouse model", *Neurobiology of Aging*—2013, pp. 1-10. In this document ligustilide is proposed as treatment in Alzheimer's disease (AD) for reducing memory deficits. The data show that chronic administration of LIG prevents the development of AD-like neuropathologies and memory impairment in aging. In addition data suggest that the likely underlying mechanism involve Klotho up-regulation. Thus klotho protein is suggested as therapeutic target for age-related AD. According to the experimental methodologies disclosed by Kuang et al. (use of antibody of Santa Cruz Biotechnology, Santa Cruz, CA, USA to detect Klotho protein), no distinction among the acting protein isoform is possible (m-KL, p-KL). When Kuang et al. refers to "secreted klotho", it does not refer to the secreted splicing variant of mammal Klotho but to other soluble forms of klotho. In fact, at that time, and until the findings of the inventors of the present invention, the alternatively secreted Klotho isoform was considered a very minor variant, not expressed (or expressed at negligible levels). In fact as reported by Forster et al.: "A klotho form containing both the KL1 and KL2 domains has been detected in both serum and cerebral spinal fluid (CSF), and has been interpreted as a proteolytic fragment of m-KL. The existence of a circulating klotho species that exactly corresponds to the peptide which would be produced from the alternatively spliced mRNA has not been reported in serum or CSF" (Forster et al. "Vitamin D Receptor Controls Expression of the Anti-aging Klotho Gene in Mouse and Human Renal Cells" Biochem Biophys Res Commun. 2011 Oct. 28; 414(3): 557-562).

Albeit the several approaches for facing cognitive impairments due to aging or some neurodegenerative diseases, there is still need of alternative treatments for ameliorating cognitive and behaviour maintenance.

SUMMARY OF THE INVENTION

The present invention results from inventor's determination of the real expression at protein level (not only as mRNA) of the splicing variant of mammal klotho protein in mouse wild-type brain tissue. Using a self-made antibody raised against a peptide amino acid sequence comprised in the last twenty amino acids of the C-terminal end of the mice s-KL, inventors detected that in the whole brain of wild-type mice (C57Bl6 of Harlan Laboratories BV), and in some specific parts of the brain the expressed isoform of Klotho protein was an isoform having a molecular weight near 70 KDa, likely s-KL but with posttranslational modifications. In addition, inventors found (data not shown) that expression levels of this protein were lowered during aging and with AD progression.

Further assays revealed that in brain this splicing variant could be determined at protein level. Moreover, the inventors have found that the secreted klotho isoform is at least ten times more abundant in the brain than in the kidney suggesting that the two isoforms may have different functions, and that s-KL activity is the isoform with an important role in the nervous system.

The inventors have herein studied the functional relevance at behavioural level, of modifying s-KL levels in the aging brain. They used AAVrh10 vectors to deliver and sustained expression of s-KL in adult and middle-aged wild-type C57BL/6J males. This study demonstrates for the first time in vivo, that six months after a single injection of s-KL into the CNS, long-lasting and quantifiable enhancement of learning and memory capabilities are found. More importantly, cognitive improvement is observable in 18-months-old mice treated once, at middle-age. These findings demonstrate the therapeutic potential of s-KL as a treatment for cognitive decline.

In summary, it is herein demonstrated that local overexpression of the secreted Klotho isoform locally in the brain after a single administration of an AAV-sKL vector protects against age-dependent memory deficits, being these effects long-lasting and quantifiable in old animals, and therefore suggesting a therapeutic potential of s-KL for dementia. Local expression of s-KL in the CNS improves cognitive performance in aged mice. s-KL expression in the CNS does not affect body weight or sensorimotor skills. Cognitive improvement is observed in 18-months-old mice treated once, at middle-age. As important, specific s-KL inhibition in hippocampus by specific shRNA-sKL impairs cognitive performance. Therefore, the inventors are able to demonstrate the key implication of secreted Klotho in memory formation, by using a dual strategy based on: (1) sKL overexpression to increase memory performance, and (2) sKL inhibition to reduce memory performance.

Thus, it is believed that the inventors have found for first time, that the klotho transcript produced by alternative splicing generates a protein of 70 KDa which they demonstrate that it is stable, and that this isoform is more abundant in brain that in other parts of the body. Moreover, it is believed that is the first time that secreted klotho is directly administered in vivo, not expressed by means of a transgenic model. As said before, the administration of s-KL leads to an amelioration of cognitive and behaviour faculties. Thus, the inventors provide the use of s-KL as a new treatment for cognitive and/or behaviour impairments, and/or with neurodegenerative and/or neuropathological diseases. This represents a more specific and CNS-oriented treatment for these diseases, since it is demonstrated herein that s-KL is the most prevalent isoform in brain parts related to cognition and behaviour natively expresses s-KL.

Prior art, as explained before, relates to transgenic mice systemically overexpressing the full-length coding region of klotho. However, full-length coding region may allow not only transcription of the transmembrane isoform, but also the alternatively splice isoform. Therefore it is not possible to dilucidate whether the amelioration of learning and memory effects reported are due to one or the other klotho isoforms. On the other hand, despite the inventors observed that both klotho isoforms seem to participate in memory performance, interestingly, overexpression of m-KL may affect in a non-specifically way other pathways unknown at this moment, resulting in relevant side effects, such as the ones described in Example 2C of this description, while specific overexpression of s-KL does not. In addition, differently from the transgenic mice of the prior art, the present approach does not alter natural Klotho levels from the birth of the animal, which may induce the apparition of compensatory effects, until key stages in the aging process are reached. Then levels are specifically modified in the brain through administration of AAVrh10 vectors with neuronal tropism.

Thus, the inventors propose as a first aspect the secreted splicing variant of mammal Klotho protein or the nucleic acid sequence coding therefor for use in the prevention and/or treatment of cognitive and/or behaviour impairment, and/or with neurodegenerative and/or neuropathological diseases in a mammal.

This aspect can also be formulated as the use of s-KL as defined above for the manufacture of a medicament for the prevention and/or treatment of cognitive and/or behaviour impairment, and/or with neurodegenerative and/or neuropathological diseases. The present invention also relates to a method for the treatment or prevention of cognitive and/or behaviour impairment, and/or with neurodegenerative and/or neuropathological diseases, comprising administering a therapeutically effective amount of s-KL protein or of nucleic acid sequence coding therefor as defined above, together with pharmaceutically acceptable excipients or carriers, in a subject in need thereof, including a human.

The splicing variant s-KL of Klotho protein appears, as above exposed, disclosed in Matsumura. In addition, other documents refer also to this splicing variant. As a way of example, the document Shiraki-lida et al., "Structure of the mouse klotho gene and its two transcripts encoding membrane and secreted protein", *FEBS Letters*—1998, vol 424, pp.: 6-10, discloses a supposed s-KL1 secreted protein detected at mRNA level. On the other side, the document of Imura et al., "Secreted Klotho protein in sera and CSF: implication for post-translational cleavage in release of Klotho protein from cell membrane", *FEBS Letters*—2001, vol 565, pp.: 143-147 refers also to a putative secreted isoform that is not detected in extracellular fluid. None of these documents points to any role of the splicing variant s-KL of klotho protein.

The term "secreted splicing variant of mammal Klotho" abbreviated as "s-KL", refers to the protein resulting from the transcript from alternative splicing, which generates a truncated form of the protein (s-KL) that is formed solely by the KL1 domain, with an approximate weight of 70 kDa. This alternative mRNA includes a specific secretion signal consisting of 15 amino acid tail that is not found in the m-KL transcript, and for this reason is also called the secreted isoform of klotho, s-KL, or the secreted splicing variant of klotho protein. s-KL is different from other forms of soluble klotho, namely p-KL, p-KL1 and p-KL2. In this description, m-KL stands for the full-length transmembrane form; p-KL stands for the soluble proteolyzed klotho, which is generated by cleavage of the m-KL; and p-KL1 and p-KL2 stand for the soluble klotho forms consisting of the KL1 domain and the KL2 domain of p-KL. m-KL comes from the full-length transcript encoding a single pass transmembrane protein with a molecular weight of approximately 130 kDa (m-KL). The protein contains three domains: a short transmembrane domain at the C-terminal, an extracellular domain composed of two internal repeated sequences of about 550 amino acids called KL1 and KL2 respectively, and a very short intracellular domain of 10 amino acids. The extracellular domain of the transmembrane form can be cleaved by metalloproteinases ADAM10 and ADAM17 resulting in another form of soluble Klotho of about 130 kDa (abbreviated p-KL for proteolyzed membrane isoform. Moreover, there is a second recognition site for the proteases ADAM10 and 17 located between the KL1 and KL2 domains, which generates two new 70 kDa isoforms, one contained the KL1 domain only (like the one generated from alternative splicing but without the specific amino acid tail), and the other one contained the KL2 domain. However, it has not been demonstrated in vivo that p-KL is proteolyzed into p-KL1 and p-KL2.

In a second aspect the invention relates to a gene construct comprising a nucleic acid sequence coding for the secreted splicing variant of mammal klotho protein (s-KL) operatively linked to an expression promoter.

Another aspect of the invention is an expression vector with central nervous system tropism comprising the gene construct as defined above, thus comprising a nucleic acid sequence coding for the secreted splicing variant of mammal klotho protein (s-KL) operatively linked to an expression promoter.

Yet another aspect of the invention is a pharmaceutical composition comprising a therapeutically effective amount of the secreted splicing variant of mammal klotho protein and/or the gene construct as defined above, and/or the vector as defined above, together with one or more pharmaceutically acceptable excipients or carriers.

It is also an aspect of the invention the secreted splicing variant of mammal klotho protein or the nucleic acid sequence coding therefor, for use in combination therapy for the prevention and/or treatment of cognitive and/or behaviour impairment, and/or with neurodegenerative and/or neuropathological diseases in a patient, wherein the protein or the nucleic acid sequence coding therefor is to be administered in combination with another active agent for the same indication.

It is also an aspect of the invention a combination of the secreted splicing variant of mammal klotho protein and/or the nucleic acid construct as defined above, and/or the vector as defined above with another active agent for use in the prevention and/or treatment of cognitive and/or behaviour impairment, and/or with neurodegenerative and/or neuropathological diseases. The combination relates to a pharmaceutically composition or preparation for administration of s-KL with any other active agent, which can be done separately, in any order, within a therapeutically effective interval, or for the simultaneously administration of the active agents.

Hereinafter are described the advantages derived from the invention and the results obtained from the experimental procedures provided below.

The Open Field test was used to study whether s-KL is able to affect locomotion, exploratory activity, emotionality, neophobia and anxiety like behaviors. Briefly, the inventors found that regardless of age, the animals overexpressing s-KL show mild hyperactivity, an increased locomotor activity when compared to control animals, and therefore, that the administration of s-KL in the CNS seems to reverse, at least partially, the gradual decline in locomotor activity observed around 12 months of age. In addition, the latencies of movement (an indicator of behavioral inhibition as a result of neophobia or anxiety) tended to be shorter in s-KL treated animals, indicating a higher disinhibition, although this effect reached statistical significance only in middle-age animals (6→12 setting), but not in old animals (12→18 setting). Consistently, the inhibition of s-KL expression mediated by shRNA-sKL had an opposite effect. Thus, some animals of the shRNA-sKL group exhibited behavioral inhibition at the start of the test, showing freezing or petrification, and latencies in leaving the central area far superior to mice overexpressing s-KL.

Next, to evaluate the effect of s-KL overexpression on the working memory the T-maze test was used. Again, the results show that administration of s-KL, regardless of age, improves cognitive abilities since s-KL treated mice make less errors in solving the task as compared to control animals. These results concur with the increase in s-KL levels found in the prefrontal cortex of the (12→18 months setting) animals. Given that in mice, deficits in working memory appear around 24 months of age, Klotho seems to be acting as an enhancer of cognitive functions.

Finally, the Morris Water Maze test was used to assess the effect of s-KL overexpression/inhibition on visual perceptual learning and memory and learning abilities. The results from both experiments showed again that s-KL treated mice are more efficient in solving the task and they learn faster than the control animals, indicating that s-KL significantly improves long-term memory in mice. In contrast, animals injected with shRNA-sKL showed problems in learning the task and swam a greater distance to reach the platform. Moreover, these opposite effects were also observed in the final memory tests (24 hours after the last training). Animals overexpressing s-KL prioritized the search in the quadrant where the platform was previously located, whilst shRNA-sKL treated animals showed no particular preference for the training quadrant, suggesting memory and/or learning problems. As expected, when compared to controls, quantification of s-KL levels 6 months after treatment (both, mRNA and protein) showed a very strong positive correlation with cognitive capacities, being statistically higher in AAV/s-KL treated mice and lower in AAV/shRNA-sKL treated mice. This pattern was observed regardless of whether animals were inyected in adulthood (6→12 months setting) or middle age (12→18 months setting).

In summary, this study provides new evidence indicating an important role for s-KL in cognitive functions, with reduced levels in hippocampus being associated to low cognitive performance. The study also demonstrates that a single icv injection of s-KL into the CNS has great potential as a long-lasting and quantifiable agent to stimulate cognitive skills, even, protecting age-dependent cognitive decline when mice were treated at old ages. To the inventors' knowledge, these are the first data obtained in vivo, in which the action of only the secreted Klotho protein improves the learning and memory capabilities of old animals when treated in adulthood. Furthermore, taking into account that these experiments were performed in naive aged animals, the results suggest s-KL may have therapeutic potential for dementia. This represents a promising new therapeutic approach for neurodegenerative disorders such as Alzheimer's Disease or Multiple Sclerosis among others.

BRIEF DESCRIPTION OF THE DRAWINGS

FIG. 4 (A) depicts per each place task (PT) test performed 1 to 4, the mean speed (in cm/s) to get the platform. FIG. 4 (B) indicates the mean distance (in cm) to get the platform. The test was performed with 18 months old mice. This figure is related to Example 2D.

FIG. 8 (A) depicts per each place task (PT) test performed 1 to 4, the mean latency (in seconds, s) to get the platform. FIG. 8 (B) indicates the mean distance (in cm) to get the platform. The test was performed with 18 months old mice. FIG. 8 (C) shows the results of the Morris Water Maze memory test performed in 12-months old mice, and performed 24 hours after the cue test part of the test. In Y-axis it is recorded the percentage of distance (%) in relation to the total distance done in several squares of the swimming pool. Left bar in each group (s-KL, shRNA-sKL and Control) is the percentage of distance in the square where previously the platform was disposed (PTf square); second bar in each group shows the percentage of distance in the opposite square (Opos PTf), third bar is the percentage of distance made in the square at right of the platform (R PTf), and right bar in each group is the percentage of distance made in the square at the left of the platform (L PTf). This figure is related to Example 3C.

DETAILED DESCRIPTION OF THE INVENTION

Figure 1:
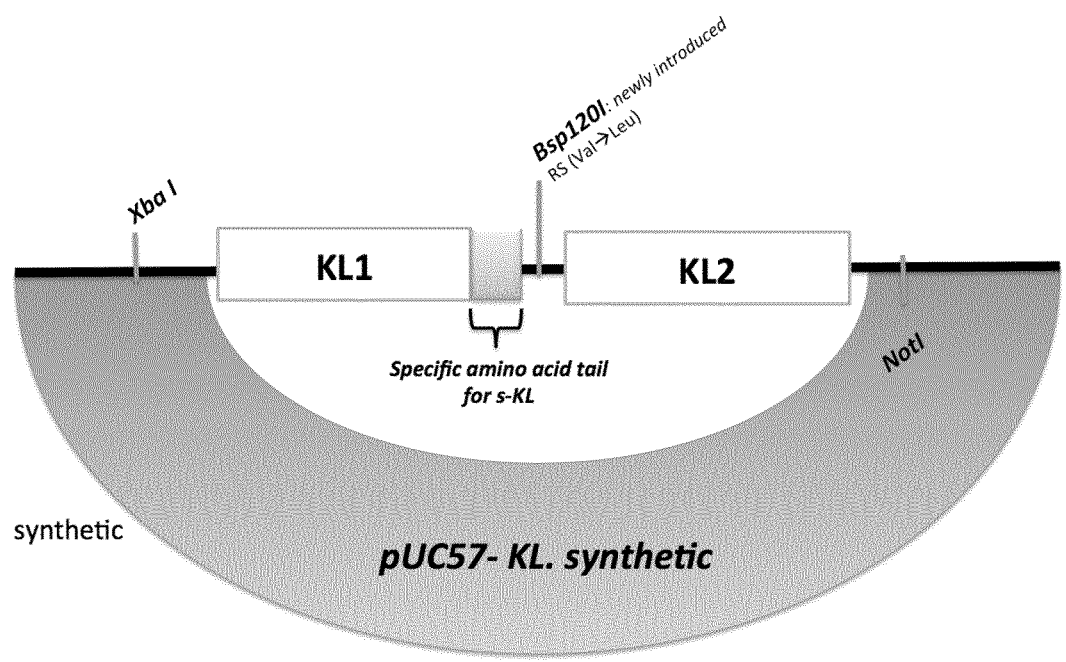
FIG. 1 is a schematic view of the procedure for constructing adeno-associated virus as vectors carrying a plasmid with the gene construct of the invention for expressing the different variants of klotho protein. In (A) the pUC57-KL synthetic plasmid (GenScript, USA) is partially represented showing an insert coding for klotho protein and indicating the restriction sites. KL1 indicates the sequence coding for KL1 domain and comprises a contiguous square representing the sequence coding for the tail of amino acids only present in the secreted splicing variant of klotho s-KL. KL2 represents the sequence coding for KL2 domain of klotho. In panel (B) it is schematically viewed the strategy to obtain from the synthetic pUC57-pKL, the pGG2-sKL plasmids carrying the sequence coding for the klotho protein. This plasmid is then introduced in 293-AAV cells (Stratagene). AAV-s-KL (or AAVrh10-s-KL) designates the adeno-associated virus carrying the plasmid with the gene construct coding for s-KL. This figure is related to Example 1.
Figure 1:
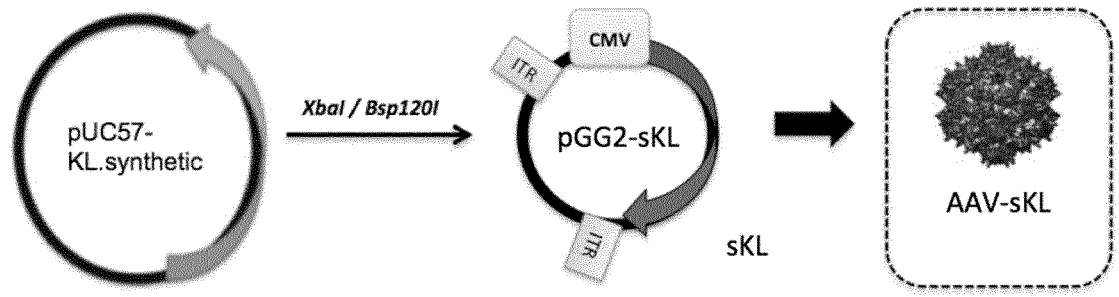

All terms as used herein, unless otherwise stated, shall be understood in their ordinary meaning as known in the art. Other more specific definitions for certain terms as used in the present application are as set forth below and are intended to apply uniformly throughout the description and claims unless an otherwise expressly set out definition provides a broader definition.

A "gene construct" according to the invention can also be named as an "expression cassette". It refers to a polynucleotide sequence including in turn a sequence coding for a protein of interest, which is operatively linked to a expression promoter, said promoter controlling expression of the sequence coding for the protein. For "operatively linked" is to be understood that the sequence coding for the protein is disposed after the sequence of the promoter (in the 5'-3' direction), or near the promoter in case restriction sites are included, or other stabilizing elements of the gene construction are present. The gene constructs (expression cassette) may also comprise small fragments with useful sequences to adapt it to more complex expression systems (vectors, plasmids), or a polyadenylation tail disposed after the sequence coding for the protein of interest. The expression cassette itself is also a expression system, being vectors or plasmids further used to protect the gene construct, or to promote entrance to cells in case of viral vectors. The "promoters" are of DNA regions that initiate transcription of a particular genes. Promoters are located near the transcription start sites of genes, on the same strand and upstream on the DNA (towards the 5' region of the sense strand). Promoters can be about 100-1000 base pairs long. A "constitutive promoter" is a promoter that is active in all circumstances in the cell, contrary to others that are regulated, becoming active in the cell only in response to specific stimuli, such as "inducible promoters". Other promoters are tissue or cell-specific, such as "neuron-specific promoters". For "polynucleotide sequence" it is to be understood as a nucleic acid molecule (DNA or RNA) comprising deoxyribonucleotides or ribonucleotides. Nucleic acid can be single or double stranded, and it includes, but it is not limited to, nucleotide sequences coding for polypeptides.

The term "adeno-associated virus (AAV)" as used herein refers to a viral vector that infects both dividing and quiescent primate (and human) cells. Because they seem to lack any pathogenic effects, and usually integrate in the same place of the genome (the AAVS1 site, in chromosome 19), this viral vectors can safely be used to transduce foreign DNA into human cells in gene therapy applications. An "expression vector", otherwise known as an "expression construct", is usually a plasmid or virus designed for protein expression in cells. The vector is used to introduce a specific gene into a target cell, and can commandeer the cell's mechanism for protein synthesis to produce the protein encoded by the gene. Expression vectors are the basic tools in biotechnology for the production of proteins. An expression vector has features that any vector may have, such as an origin of replication, a selectable marker, and a suitable site for the insertion of a gene such as the multiple cloning site.

The "percentage of homology" between two amino acid sequences is to be understood as the percentage of the sequence positions identical or replaced with other amino acids with lateral chains of similar features (i.e. polar, non-polar, with amino groups, with —SH groups, that is, amino acids the same class), according to the broadly accepted classifications known by an expert in the field. The "percentage of identity" between two amino acid sequences is to be understood as the percentage of the sequence positions with identical amino acids. The percentage of homology and of identity between sequences may be calculated by means of "sequence alignment". The sequence alignment may be local or global. In the sense of the present invention the percentage of homology and of identity will be calculated, preferably, over a global alignment, among the entire sequence or an entire active fragment of the sequence. Global alignments are more useful when the sequences are similar and have approximately the same size (long). There are several algorithms available in the state of the art for performing these global alignments. There are also bioinformatics tools using such algorithms to obtain the percentage of identity and homology between sequences. As an example, global alignment between sequences may be performed by means of the well-known GGSEARCH or GLSEARCH software. The identity between two amino acid sequences is preferably determined by using the BLASTP algorithm disclosed in Altschul, S. F., et al. "Gapped BLAST and PSI-BLAST: a new generation of protein database search programs", *Nucleic Acids Research*—1997, Vol. No. 25, pp.: 3389-3402, and NCBI.

As will be depicted in the examples below, brain injection to mice of expression vectors comprising gene constructs with a nucleic acid sequence coding for the secreted splicing variant of mammal klotho protein (s-KL) operatively linked to an expression promoter, lead to an amelioration of cognitive and behaviour functions when these mice were submitted to several tests. These data prove that s-KL can be used in the treatment and/or prevention of cognitive and/or behaviour impairment, and/or with neurodegenerative and/or neuropathological diseases.

The invention encompasses the administration of both the s-KL as protein or as nucleic acid sequence coding therefor, this last in a suitable form to be administered, such as in the form of a gene construct and/or expression vector. Thus, "s-KL" herein means both forms of s-KL.

In a particular embodiment, the cognitive and/or behaviour impairment is associated with aging. The term "associated with" means that cognitive and/or behaviour impairment takes place when mammals, in particular human, get older (aging), such as in senile dementia, and also may take place in some neurodegenerative and/or neuropathological diseases, being cause or consequence of the physiological parameters also affected in said diseases. Senile dementia is related to a condition appearing due to the natural non-pathological aging, and it implies many cognitive and/or behaviour impairments, such as balance problems, tremors, memory distortions, anxiety, depression, apathy, agitation and irritability. Senile dementia may also be associated with neurodegenerative diseases as Alzheimer's disease.

In a particular embodiment the cognitive and/or behaviour impairment associated with aging is one manifested in senile dementia.

Thus, in a particular embodiment of the first aspect of the invention, the s-KL is for use in the prevention and/or treatment of a cognitive impairment selected from the group consisting of learning and memory problems. More particularly, is for use in learning impairments, in particular learning procedure impairments, and memory problems, in particular memory losses, impairment of working memory, and impairment of long-term memory, the latter including spatial and episode memory impairments.

In another particular embodiment, optionally in combination with any embodiment above or below, s-KL is for use in the prevention and/or treatment of a behaviour impairment selected from anxiety and agoraphobia.

Also in another particular embodiment, optionally in combination with any embodiment above or below, s-KL is for use in the prevention and/or treatment of cognitive and/or behaviour impairment associated to neurodegenerative and/or neuropathological diseases selected from the group consisting of Alzheimer's disease, Parkinson's disease, Huntington's disease and Amyotrophic lateral sclerosis, Dementia with Lewy bodies, Creutzfeldt-Jakob disease, Multiple Sclerosis, and Ataxia telangiectasia, post stroke dementia, post-traumatic dementia, senile dementia, and craniocerebral trauma.

In a more particular embodiment s-KL is for use in the prevention and/or treatment of cognitive and/or behaviour impairment associated to Alzheimer's disease. In particular it is for use in the prevention and/or treatment of anxiety impairment in Alzheimer's disease.

Thus, s-KL for use according to the invention is, in a particular embodiment for the prevention and/or treatment of cognitive and/or behaviour impairment in mammals, and particularly in humans. Klotho protein has a high percentage of homology among mammals as it is shown in the following table (analysis by BLAST, amino acid sequences from NCBI):

|  | Rat | Dog | Mouse | Goat | Cebus |
|---|---|---|---|---|---|
| Human | 92% | 94% | 92% | 93% | 93% |
| Cebus Capuccino (primate) | 90% | 92% | 90% | 92% | — |
| Goat | 93% | 94% | 93% | — | — |
| Mouse | 97% | 93% | — | — | — |
| Dog | 92% | — | — | — | — |
| Rat | — | — | — | — | — |

In a particular embodiment, s-KL for use as above exposed is a polypeptide selected from SEQ ID NO: 1, SEQ ID NO: 2 and a polypeptide with a percentage of identity of at least 88% with any of SEQ ID NO: 1 or SEQ ID NO: 2. The percentage of identity determined by using the BLASTP algorithm.

In yet a more particular embodiment it is a polypeptide selected from amino acid sequences SEQ ID NO: 1 and SEQ ID NO: 2. In other particular embodiments, s-KL for use as above exposed is a polypeptide with a percentage of identity with either SEQ ID NO: 1 or SEQ ID NO: 1 from 88% to 100%. Ranges of identity percentages comprise 88%, 88.5%, 89%, 89.5%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5% and 100%. In another more particular embodiment the percentage of identity of the polypeptide is from 88% to 90%; and yet more particularly from 88% to 88.5%.

SEQ ID NO: 1 is the amino acid sequence of the transcript from alternative splicing of α-klotho human gene, comprising the KL1 domain sequence, with an approximate weight of 70 kDa, but with a specific secretion signal consisting of 15 amino acid tail that is not found in the m-KL transcript. α-klotho human gene is the one located in Chromosome 13 NC_000013.11 (33016063 . . . 33066145) of the assembly GRCh38 (24 Dec. 2013) for the human genome maintained by the Genome Reference Consortium. SEQ ID NO: 1 derives from the corresponding cDNA of SEQ ID NO: 5, deriving from the alternative splicing transcript of the mRNA sequence with the GenBank database accession number NM_004795 of 5012 base pairs, version 3 of 3 May 2014.

SEQ ID NO: 2 is the amino acid sequence of the transcript from alternative splicing of α-klotho mouse gene, comprising the KL1 domain sequence, with an approximate weight of 70 kDa, but with a specific secretion signal consisting of 15 amino acid tail that is not found in the m-KL transcript. α-klotho mouse gene is the one located in Chromosome 5 (150,952,607-150,993,809) of UCSC Genome Browser on Mouse July 2007 (NCBI37/mm9) Assembly for the mouse genome. SEQ ID NO: 2 derived from the corresponding cDNA of SEQ ID NO: 6, deriving in turn from the alternative splicing transcript of the mRNA sequence with the GenBank database accession number NM_013823 of 5124 base pairs, version 2 of 15 Feb. 2015.

The polypeptides with a percentage of identity of at least 88% with any of SEQ ID NO: 1 or SEQ ID NO: 2 encompass mammal proteins derived from amino acid variations of the sequences including single or of two or three amino acid substitutions in SEQ ID NO: 1 or 2, deletion of one or two amino acids, insertion of one or two amino acids at any position of the sequence, all these amino acid variations in relation to SEQ ID NO: 1 or 2 with the proviso that the resulting proteins have the same function as the s-KL from which derive. The polypeptides with a percentage of identity of at least 88% with any of SEQ ID NO: 1 or SEQ ID NO: 2 encompass also s-KL of mammals other that mice and human. As above indicated, the identity is determined by global alignment between sequences performed by means of the BLASTP algorithm.

In another particular embodiment of the first aspect of the invention, the s-KL for use as above exposed is a polypeptide consisting in SEQ ID NO: 1 or SEQ ID NO: 2.

s-KL may be used directly in the form of the protein, conveniently directed or finally reaching brain or central nervous system (CNS). This protein can be administered, for example in the form of a pharmaceutically composition comprising a therapeutically amount of the protein suspended o dissolved in a carrier (solvent) useful for injection into the brain or useful for intravenous injection (mainly), together with acceptable excipients for stabilizing the protein.

On the other hand, s-KL can be expressed inside target cells of CNS by means of gene therapy. To this aim the invention also provides the new gene construct comprising a nucleic acid sequence coding for the secreted splicing variant of mammal klotho protein (s-KL) operatively linked to an expression promoter. When in the present invention it is said "a nucleic acid sequence coding for the secreted splicing variant of mammal klotho protein (s-KL)" is to be understood, in particular, the cDNA sequence resulting from the reverse transcription (RT-PCR) of mRNA for said s-KL in the mammal. In a particular embodiment the expression promoter operatively linked is selected from a constitutive expression promoter, an inducible promoter and a neuron-specific expression promoter. In a particular embodiment, the gene construct according to the invention comprises the nucleic acid sequence SEQ ID NO: 3. SEQ ID NO: 3 comprises the cytomegalovirus intermediate-early (CMV IE) promoter, the sequence coding for s-KL (cDNA of mouse s-KL) and a polyadenylation chain (poly A). In another particular embodiment the gene construct according to the invention comprises the nucleic acid sequence SEQ ID NO: 4, equivalent to SEQ ID NO: 3 but with the sequence coding for human s-KL protein (cDNA of human s-KL).

In another particular embodiment the gene constructs consist in either SEQ ID NO: 3 or SEQ ID NO: 4.

All these gene constructs are able to express the protein of interest once in the cell, and particularly in the CNS cells.

In order to facilitate administration of the constructs the invention also proposes new expression vectors with central nervous system tropism comprising the gene construct as defined above, thus comprising a nucleic acid sequence coding for the secreted splicing variant of mammal klotho protein (s-KL) operatively linked to an expression promoter, and particularly to a constitutive expression promoter.

Suitable expression vectors for the purposes of the invention are vectors with central nervous system (CNS) tropism or that effectively transduce CNS cells. Expression vectors for gene therapy are usually viruses, and particularly retroviruses, adenoviruses, envelope protein pseudotyping of viral vectors, replication-competent vectors, cis and trans-acting elements, or Herpes simplex virus.

In a particular embodiment of these expression vectors, they are viral vectors.

More particularly, the expression vectors are adeno-associated virus, and more particularly adeno-associated virus with CNS tropism, which can be of serotype 1-10. Particularly, the adeno-associated virus is of serotype rh10 (AAVrh10).

Other possible vectors for the delivery of the gene constructs comprising s-KL coding sequence include liposomes, micro- and nanoparticles that avoid damage of the gene construct and moreover facilitate entrance of the construct inside the CNS cells in an effective and specific manner. s-KL in the form of plasmids or naked DNA can also be administered for gene therapy by non-viral methods, such as injection of naked DNA, physical methods to enhance delivery, electroporation, gene gun, sonoporation, magnetofection, or hydrodynamic delivery. Other chemical methods to enhance delivery are the use of oligonucleotides, lipoplexes, polymersomes, polyplexes, dendrimers or inorganic nanoparticles.

Another aspect of the invention is, as above exposed, a combination of the secreted splicing variant of mammal klotho protein and/or the nucleic acid construct as defined above, and/or the vector as defined above with another active agent for use in the prevention and/or treatment of cognitive and/or behaviour impairment associated with aging, and/or with neurodegenerative and/or neuropathological diseases.

In a particular embodiment, said combination is for the prevention and/or treatment of cognitive and/or behaviour impairment associated with Alzheimer's disease (AD). The combination relates to a pharmaceutically composition or preparation for administration of s-KL with any other active agent, such as donepezile hydrochloride (Aricept, Pfizer), memantine, rivastigmine, and ligustilide, which can be done separately, in any order, within a therapeutically effective interval, or for the simultaneously administration of the active agents. In yet a more particular embodiment the combination is for use in the prevention and/or treatment of anxiety in patients of AD.

s-KL can be administered to the patient via mucosa (e.g., nasal, sublingual, vaginal, buccal, or rectal), parenterally (e.g., subcutaneous, intravenous, intramuscular, or intraarterial injection, either bolus or infusion), orally, transdermally or via inhalation by means e.g. of an aerosol. Formulations suitable for parenteral administration, such as, for example, by intraarticular, intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In some embodiments, the composition is administered by injection e.g subcutaneous, intraperitoneal, intravesically, intravenous, by infusion, e.g., using a reservoir or osmotic minipump or intramuscular. The formulation can be provided in unit-dose or multi-dose sealed containers, such as ampoules and vials.

In a particular embodiment s-KL is administered to the patient parenterally and more particular, intravenously.

In other particular embodiments s-KL is administered with direct deliver to the central nervous system, more particularly injected intrathecally or intracisterna magna (ICM), and particularly by means of a patch, a micropump or a microcapsule delivery system.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1. Generation of Plasmidic Vectors Coding for Secreted Klotho Protein. Production of AAV Viral Vectors for Transduction Generation of viral vectors for gene therapy was performed from synthetic constructs. Gene construct (plasmid) pCR-KL-TOPO-KL (ImaGenes™, Germany) coded for full-length cDNA of the transmembrane protein isoform of Klotho (m-KL). Klotho sequences were then cloned in pGG2 plasmid (of SEQ ID NO: 12 and courtesy of Genethon) by means of ligation with restriction enzymes, said pGGs plasmid carrying the Inverted Terminal Repeat (ITR) sequences of the adeno-associated virus serotype 2 (AAV2) genome and a multiple cloning site (MCS) where the gene of interest was cloned under the control of cytomegalovirus immediate-early promoter (CMV IE). To do this a cDNA of m-KL was extracted from pCR-KL-TOPO-KL with XbaI/EcoRI restriction enzymes and cloning the fragment in vector p123T comprising sequence of CMV IE promoter (MoBiTec, Alemania), EMBL-EBI accession number Z46733, release 121 of 29 Aug. 2014) using the same enzymes. The fragment comprising sequences of CMV IE promoter and the sequence coding for m-KL (herewith termed CMV IE-mKL) was cloned in pGG2 plasmid, comprising sequence of CMV IE promoter, to obtain the expression cassette flanked with Inverted terminal repeats (ITR). This plasmid was termed pGG2-m-KL (of SEQ ID NO: 13).

A gene construct comprising the cDNA coding for s-KL was generated from synthetic pUC57-KL. (GenScript, USA) of SEQ ID NO: 14. This plasmid contained appropriate restriction sites for cloning s-KL. In FIG. 1(A) it is schematically depicted the plasmid map. FIG. 1(B) shows strategy to clone the s-KL isoforms that could be derived from synthetic pUC57-KL.

A plasmid including the s-KL coding sequence (pGG2-s-KL, SEQ ID NO: 15) was generated with XbaI/Bsp120I targets, which are compatible with NotI/XbaI to open pGG2 vector.

pGG2-s-KL and pGG2-m-KL were in this particular example obtained with pGG2 plasmid. Anyway, other plasmids are useful while allowing packaging in viral capsid of the gene constructs comprising CMV IE promoter operatively linked to the sequence coding for s-KL and a polyadenylation chain (SEQ ID NO: 3 for murine s-KL, and SEQ ID NO: 4 for human s-KL); as well as of the same constructs for m-KL (human or murine). The packaging of these sequences leads to the same viral genome and viral capsid proteins, independently of the plasmids used for the generation of AAV as exemplified below.

Further AAV vectors comprising either plasmid pGG2-mKL or pGG2-sKL were generated by means of triple transfection of 293-AAV cells from Stratagene (70% confluency) with the pGG2 plasmids, the pXX6 plasmid (SEQ ID NO: 16, by courtesy of Genethon), carrying AAV genes for AAV amplification, and the plasmid pREp2Cap10 (SEQ ID NO: 17) (MTA Dr. J. M. Wilson, University of Pennsylvania), this later carrying sequences Cap and Rep of AAVrh10. Viruses were then purified using ultra centrifugation in iodixanol gradient, counted by picogreen method (Piedra et al., "Development of a rapid, robust, and universal picogreen-based method to titer adeno-associated vectors", *Hum Gene Ther Methods*—2015, vol 26(1), pp: 35-42; or doi: 10.1089/hgtb.2014.120 PMID: 25640021) and stored at −80° C. until moment of use. The expression vectors were named AAVrh10_pGG2-sKL and AAVrh10_pGG2_mKL. Primers for quantification of AAVrh10_pGG2_mKL are m-KL-forward 5'-TTCAAACCCGGAAGTCTTTG-3' (SEQ ID NO: 7), and m-KL-reverse 5'-CCAGGCA-GACGTTCACATTA-3' (SEQ ID NO: 8).

The procedure was as follows: 20 plates of 15 cm of diameter with 293-AAV cells from Stratagene (70% confluency) were transfected with Polyethyleneimine PEI (PolyScience) with 500 μg of pXX6, 250 μg of pRep2Cap10 and 250 μg of pGG2 plasmid. The three plasmids were mixed in media DMEM and added to the plates to a final volume of 14 ml/plate. 6 hours later the media was changed. 48 hours post-transfection cells were scrapped and centrifuged. They were resuspended in lysis buffer (50 mM Tris (Sigma), 20 mM NaCl (Panreac) and 2 mM MgCl2 (Panreac)). For AAV purification and after 3 cycles of frost and defrost, cell residues were obtained by centrifugation and supernatant was saved. Benzonase (50 U/ml) was added to the supernatant to decompose cell DNA. Viral particles were further precipitated with polyethyleneglycol (PEG at 1 ml/4 ml of cell lysate). Centrifugation at 8000 g for 15 minutes allowed a pellet with the viral particles. 15 ml of lysis buffer were added to iodixanol gradient tubes and the viral particles removed after centrifugation at 690000 g for 1 hour.

Example 2. In Vivo Administration of AAV s-KL Vectors in Old Mice

Example 2A: Administration of AAV Vectors

Figure 2:
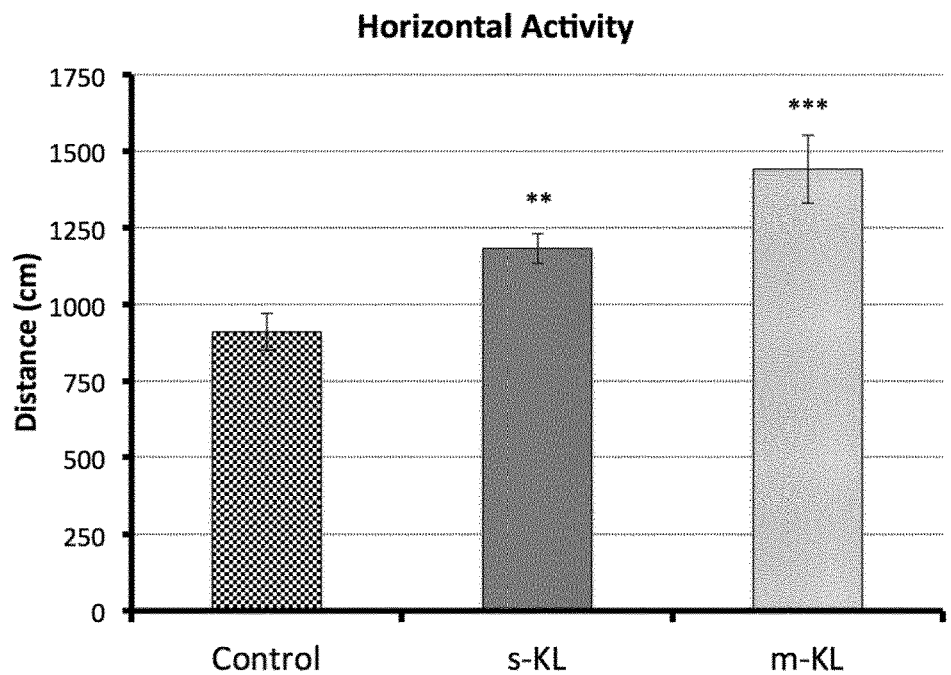
FIG. 2 (A, B) shows, respectively, the total distance (cm) in open field test made by Null, m-KL or s-KL 18 months old mice (panel A); the total distance (cm) made per minute for each type of mouse (panel B), recorded during one minute (in X-axis, MIN is the minute 1 to 5 of assay, circles for Null, squares for m-KL and triangles for s-KL). This figure is related to Example 2C.
Figure 2:
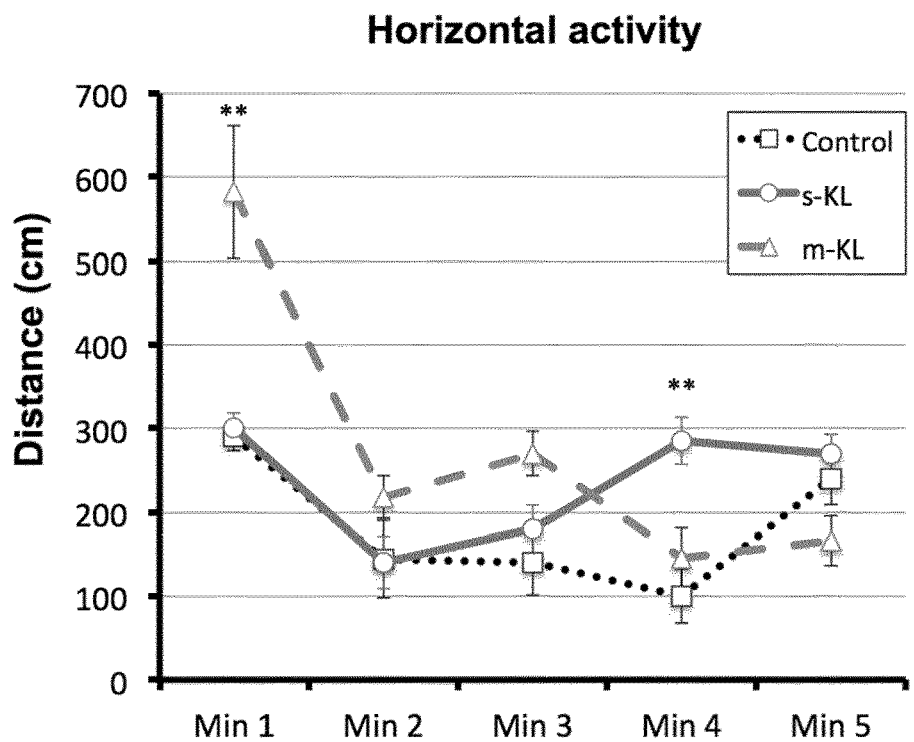
Figure 3:
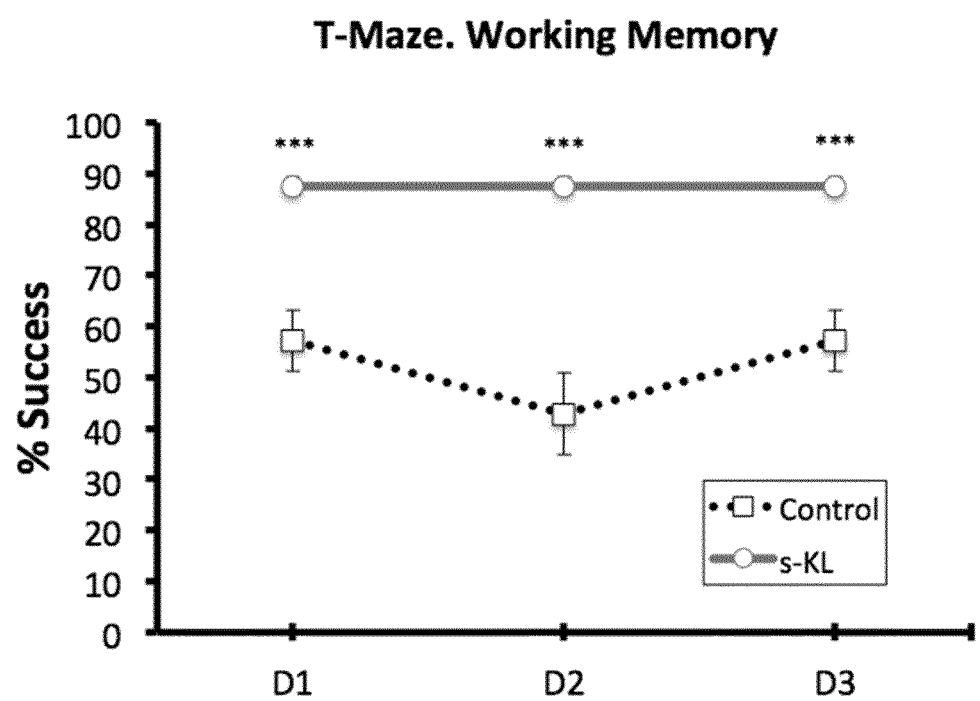
FIG. 3 shows the results of a T-maze test performed in control mice (squares), and s-KL mice (circles). Percentage of success in the free choice test distributed along the different days of the assay (from day 1 to day 3). This figure is related to Example 2D.

Long-term effects of klotho overexpression in the aging CNS were evaluated in C57BL/6 mice injected at 12 months of age (middle-aged, N=10), and tested 6 months later, when they reached old age (18 months), through a battery of tests for behavioural assessment and functional analysis (FIG. 2 and FIG. 3). The control group was injected with an AAVrh10 vector encoding an irrelevant DNA sequence and the treated group with an AAVrh10 vector encoding the secreted (s-KL) Klotho isoform. AAV vectors were injected intracerebroventricularly (icv) to mimic the endogenous production system, in which Klotho produced in the CNS is released into the CSF and distributed throughout the brain.

For the in vivo assays, C57B16 mice of Harlan Laboratories BV (wild-type males) were used. All experiments with animals and necropsies were done in Universitat Autònoma de Barcelona (Spain) according to Spanish applicable law. Protocols were approved by Ethics Committee. Animals were fed ad libitum in Macrolon cages at 22° C. and 12 hours of dark and light cycles starting at 8:00 h.

Mice were anesthetized by intraperitoneal injection of ketamine (10 mg/kg of body weight; Imalgene 500; Rhone-Merieux) and xylazine (1 mg/kg of body weight; Rompun; Bayer) and mounted onto a stereotactic frame (David Kopf Instruments, CA, USA). Wild-type mice (12 months old) were injected in the brain to reach cerebrospinal fluid (CSF) with the expression vectors of Example 1. So, there were generated s-KL mice (injected with AAVrh10_pGG2-sKL, also abbreviated AAVrh10-s-KL). As control (Null mice), a vector coding for an irrelevant gene was used. Experimental groups consisted in 10 animals per group (n=10). Intraventricular injection was performed in the third lateral ventricle of brain with the aid of a stereotaxic device. The administered dose of the expression AAV vector was of $1.10^{10}$ vector genomes per mouse (vg/mouse) in a single dose of 3 μL.

Example 2B. Overexpression of s-KL in the CNS does not Affect Body Weight or Sensorimotor Skills in Old Mice Behaviour and cognitive tests were conducted when mice were 18-months old. Firstly, sensorimotor tests were conducted (Day 1), followed by the corner test and the open field test (Day 2). Next, it was performed the T-maze test (Day 3-5). The Morris Water Maze (MWM) test was done at the end (Days 6-12).

The body weight of animals was monitored once a month, from 12 to 19 months of age. Reflexes (visual reflex and posterior legs extension reflex tests) were measured three times by holding the animal by his tail and slowly lowering it onto a black surface. The motor coordination and equilibrium were assessed by the distance covered and the latency to fall off a horizontal wooden rod (1.3 cm wide) on two consecutive 20 s trials, respectively. In order to increase the difficulty of the task, the test was repeated on a metal wire rod (1 cm diameter). Prehensility and motor coordination were measured as the distance covered on the wire hang test, which consisted in allowing the animal to cling from the middle of a horizontal wire (diameter: 2 mm, length: 40 cm, divided into eight 5 cm segments) with its forepaws for two trials of 5 s and a third 60 s trial. Muscle strength was measured as the time until falling off the wire in the 60 s trial. All the apparatus was suspended 40 cm above a padded table.

Behavioural assessment of treated animals started with the evaluation of putative effects of s-KL in physical status, namely body weight and reflexes as well as basic sensorimotor functions such as balance, coordination, prehensility, strength and resistance. These measures allow detecting possible differences between groups that could subsequently affect results depending on motor performance. Of note, there were no significant differences in the mean weight between both groups of animals (p=0.48). However, s-KL treated mice had a relatively stable body weight throughout the 6 months post injection, whilst the null-treated group's weight progressively increased during middle age and decreased in old age. The results shown in Table 1, also show a similar sensorimotor function in s-KL treated and control groups as measured by the visual placing and hindlimb reflexes test; the wood and metal rod tests; and the hanger tests. It is therefore assumed that all animals were in similar physical conditions when analyzed in subsequent behavioural tests.

TABLE 1

| Sensorimotor Tests | | |
|---|---|---|
| | Control | s-KL |
| Visual reflex (correct) | 100% | 100% |
| Wooden Bar (s) | 19.0 ± 1.0 | 17.86 ± 1.25 |
| Metal Bar (s) | 3.5 ± 0.67 | 3.21 ± 1.19 |

Example 2C: s-KL Overexpression in the CNS Ameliorates Age-Related Motor Decline without Affecting Anxiety-Like Behaviours in Old Mice Human aging, both normal and in age-related diseases, is associated with highly correlated changes in motor performance that parallel alterations in cognition and motivation. Therefore, since locomotion and exploratory behaviours decrease with age, we first sought to determine whether overexpression of the secreted Klotho isoform in the CNS could affect locomotor/exploratory behaviour in injected mice compared to controls using the Open Field Test.

This test was developed to study neophobia and anxiety-like behaviours and is most often used in rodents to qualitatively and quantitatively measure general locomotor activity (horizontal and vertical activities) and willingness to explore (mostly shown by the vertical activity). Open field activity, including total distance travelled, rearing exploratory behaviour, latency of behavioural events, self-grooming behaviour and defecations, were examined in order to determine whether sKL overexpression in the aged mice brain elicited changes in locomotion, exploratory activity, emotional and anxiety-like behaviors.

In order to know specifically whether m-KL and s-KL may induce different effects in the treated animals, wild-type mice (12 months old) were also injected intraventricularly in the brain with the AAVrh10_pGG2_mKL vector (n=10).

Results of this test are depicted in FIG. 2 (A, B). In FIG. 2(A) total distance (cm) made in open field is depicted in bars. In FIG. 2(B) there are recorded the total distance (cm) made per minute for each type of mouse. In Table 2 different parameters to evaluate the exploratory activity of the animals in the open field test.

TABLE 2

| Exploratory activity in the open field test | | |
|---|---|---|
| | Control | s-KL |
| Latency to leave the center(s) | 6.75 ± 1.79 | 3.98 ± 1.11 |
| Latency to arrive to periphery (s) | 9.14 ± 1.36 | 7.7 ± 1.09 |
| Latency first rearing (s) | 18.42 ± 2.91 | 24.33 ± 3.92 |
| Number of groomings | 2.86 ± 0.10 | 2.29 ± 0.12** |
| Latency first grooming (s) | 84.17 ± 11.63 | 90.33 ± 24.06 |
| Number of defecations | 2.13 ± 0.49 | 1.94 ± 0.32 |

As shown in FIG. 2A when tested at the age of 18-19 months, mice previously icv administered at 12 months with s-KL or m-KL travelled a greater total distance compared to control mice (p<0.01; p<0.001 respectively). Interestingly, the greater locomotor activity observed in m-KL treated mice appears to be related to anxiety, since differences in the distance travelled were not observed in the first three minutes of the test (FIG. 2B). In comparison, the greater locomotor activity observed for the s-KL mice is not associated with anxiety since the distance run is statistically significant at the end of the test, and therefore is more associated with exploratory behaviour, which is more typical of younger animals (FIG. 2B). This is in agreement with the other parameters measured, such as the sequence of behavioural events and the number of defecations, which indicate similar levels of neophobia and emotionality in both groups of animals when confronting the open arena (Table 2). Only, a reduction in the number of groomings (p=0.0032) in treated animals was statistically significant.

Example 2D: CNS s-KL Overexpression Improves Cognitive Performance in Old Mice In order to study the possible long-lasting neuroprotective effect of Klotho in the CNS, animal's cognitive skills were evaluated in two learning and memory tests: T-maze and Morris Water Maze.

The spontaneous exploratory behavior was tested in a T-shaped maze (arms, length 25 cm). Animals were placed inside the vertical arm of the maze facing the end wall. The performance was evaluated by determining the time elapsed until the animal crossed (four-paw criteria) the intersection of the three arms. The working memory paradigm consisted in two consecutive trials: one forced choice and one free choice, with a 90 s intertrial interval. In the forced choice, only one of the arms according to a random order (contra-balanced in each group) was accessible. Each mouse was placed in the "vertical" arm of the maze with its head facing the end wall and it was allowed to explore the maze. After spending 20 s in the accessible arm (learning criterion), the animal was put back into the home cage starting box. Nineteen seconds later, it was again allowed to explore the maze in a free choice trial where both arms were accessible. The arm chosen by the mouse and the time spent in each arm during the free choice was recorded. The choice of the already visited arm in the previous trial before exploring the arm that was inaccessible was considered as an error. Also the time spent to complete the exploration of the three arms in the maze was recorded. The olfactory trails were removed by cleaning the surface of the maze during the intertrial intervals.

TABLE 3

Different parameters in the forced choice and free-choice trial

| | Control | s-KL |
|---|---|---|
| Forced Choice in T-maze | | |
| T-intersection (latency, s) | 15.14 ± 1.38 | 12.04 ± 1.11 |
| Criteria Achievement (frequency/total n) | 6/8 | 5/6 |
| Exploration criteria (latency, s) | 76.19 ± 3.13 | 102.0 ± 14.56 |
| Memory Assay in T-maze | | |
| Criteria achievement (frequency/total n) | 5/6 | 5/5 |
| Errors (frequency/total n) | 2.94/6 | 0.65/5** |

As shown in Table 3, in the forced choice tasks in the T-maze all groups met the criteria similarly, although not all animals were able to complete the task. Subsequently, only those animals that met the criteria were administered a second trial, the memory task. Results show that the increase in s-KL expression in the CNS in aged mice significantly improved their memory score (frequency of errors of 0.65/5) compared to the control group (frequency of errors of 2.94/6). This is demonstrated by significantly fewer errors in choosing the maze path (p=0.0018). Moreover, this ability was sustained over three consecutive days (FIG. 3).

These data indicated that an increase in the expression of s-KL in CNS allows improving punctuation in relation to controls. This moreover implies a better working memory, said memory of particular interest in aging people and in Alzheimer's disease.

Further analysis of cognitive abilities in treated animals was performed in the Morris Water Maze. This test consists of one cue task for visual perceptual learning, four days of place task for spatial reference learning and memory followed by a probe trial for long-term (24 h) memory. In the place-learning task, mice were trained to locate a platform (7 cm diameter, 1.5 cm below the water surface, position indicated by a visible 5×8 cm striped flag) in a circular pool (Intex Recreation Corp. CA, USA; 91 cm diameter, 40 cm height, 25° C. opaque water) located in a test room with distal visual cues. This required four platform trial sessions per day with trials spaced 15 min apart. In each trial, the mouse was gently released (facing the wall) from one randomly selected starting point (N, S, E, or W) and allowed to swim until escaping onto the platform (always in the middle of the SE quadrant). Mice that failed to find the platform within 60 s were placed on it for 20 s, the same period as was allowed for the successful animals. Twenty-four hours after the last cued platform trial, animals were tested for the cue learning of a visual platform consisting of four hidden platform trials (20 min apart). The platform was hidden 1.5 cm below the water surface, with its new position (NW) indicated by a visible striped flag (5×8 cm), and the distal cues were removed. During each trial, the escape latency, the distance traveled, and the mean speed were measured by means of a computerized tracking system (SMART, Panlab S.A., Spain).

Figure 4:
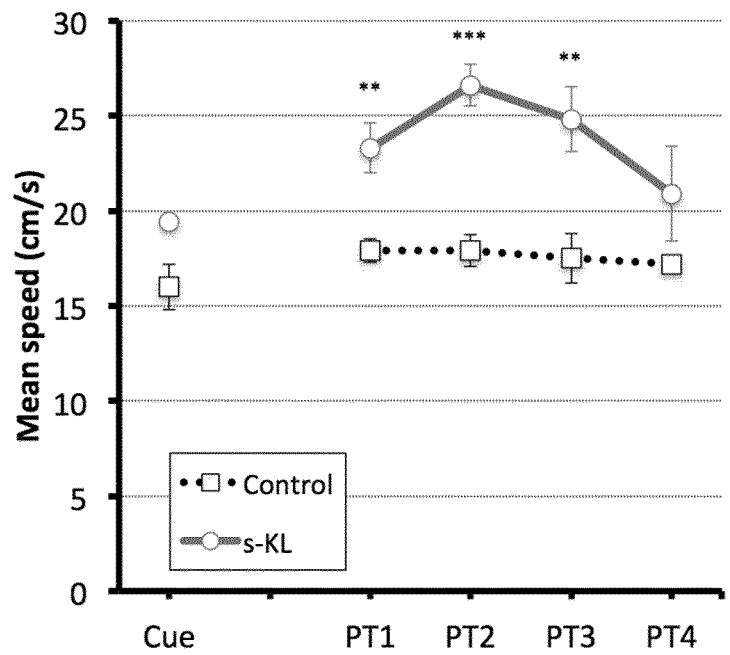
FIG. 4 depicts the results of a Morris Water Maze test performed in s-KL mice (circles), and Null mice (squares).
Figure 4:
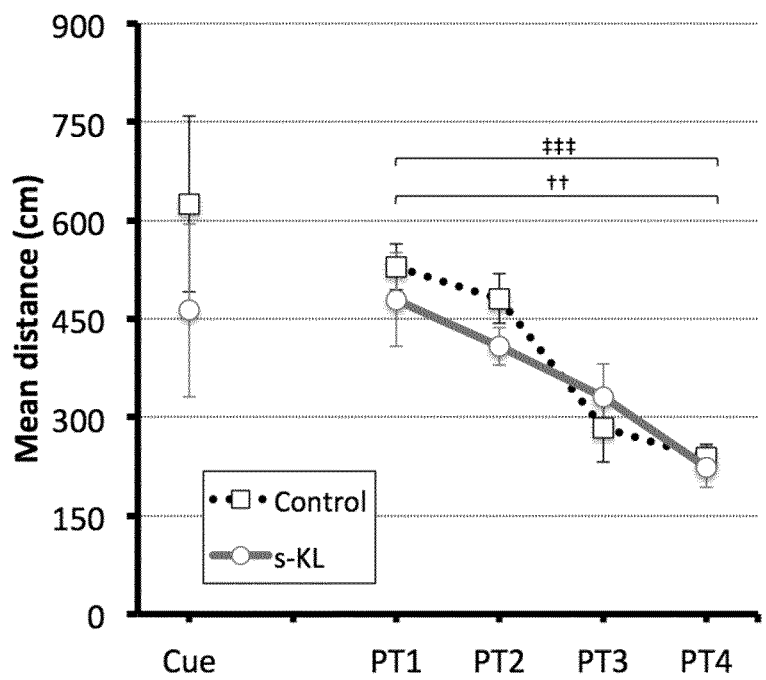

Notably, swimming speeds were significantly higher in the group treated with s-KL (FIG. 4A). This is in agreement with the increased horizontal locomotor activity observed in these same animals in the open-field test. We therefore considered distance was a more accurate variable than latencies or speed to evaluate learning and memory skills in these animals. Importantly, despite their age, both groups demonstrated learning over the four training days since there was a gradual reduction in the distance covered to solve the task (FIG. 4B, p<0.01 for Control; p<0.001 for s-KL). Finally, the acquisition of spatial learning was similar, regardless of the group. This indicates that before the memory tests, all animals were equal when facing the task.

Figure 5:
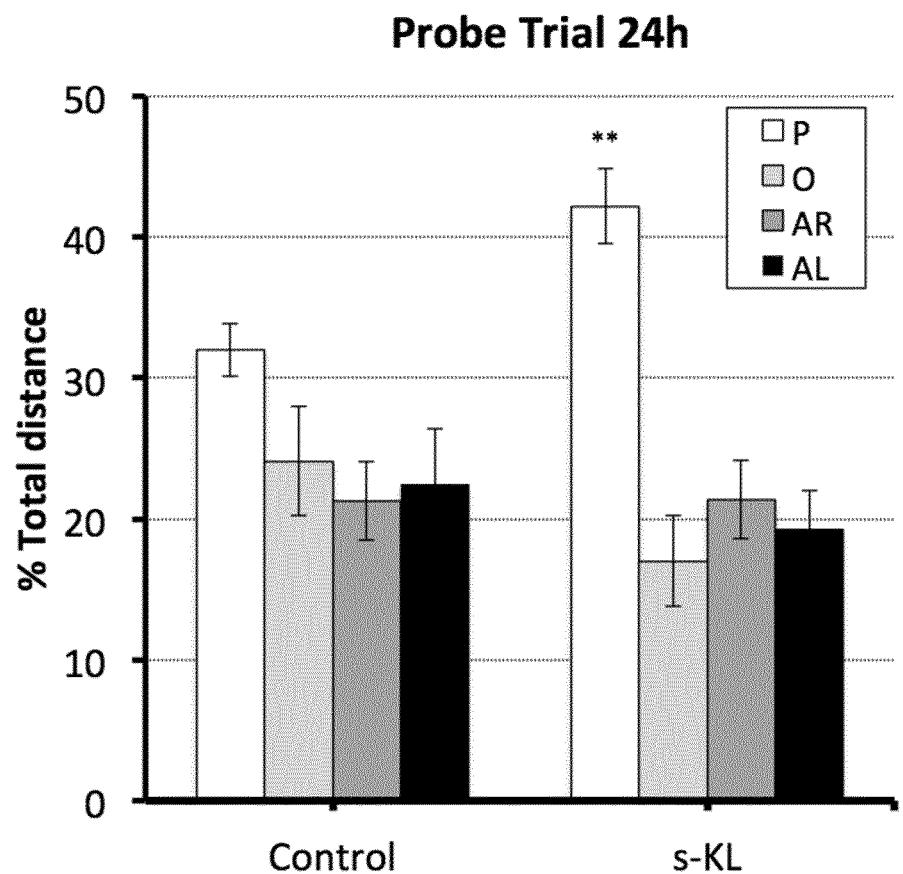
FIG. 5 is a graphic showing the results of a long-term memory test performed 24 hours after a cue test part of the Morris Water Maze test. The test was performed with 18 months old mice. In Y-axis it is recorded the percentage of distance (%) in relation to the total done in several squares of the swimming pool. Left bar in each group (Null, or s-KL) is the percentage of distance in the square where previously the platform was disposed (PTf square); second bar in each group shows the percentage of distance in the opposite square (Opos PTf), third bar is the percentage of distance made in the square at right of the platform (R PTf), and right bar in each group is the percentage of distance made in the square at the left of the platform (L PTf). This figure is related to Example 2D.

Finally, 24 hours after the last session of acquisition (Probe Trial 24 h), aged control mice had a poorer performance in the long-term memory trial. They showed less preference for the training quadrant than they displayed in the short-term memory trial. In contrast, the s-KL treated group had a clear preference for the training quadrant, statistically significant from the control (p<0.01, FIG. 5). These results indicate that the cognitive effects of increased levels of s-KL in the CNS are connected with selective improvement in long-term memory.

Example 2E. Quantification of Viral Genomes in the CNS of Injected Mice

After all tests were terminated mice were sacrificed and one half of brains fixed in paraformaldehyde (4%) for histology. Other half part of brains was used for determining in different brain sections (prefrontal cortex, PFC; cortex, C; hippocampus, H; and cerebellum, CB), the presence of viral genomes (vg) and the expression levels of s-KL.

For these analyses, quantitative PCRs were performed. For the detection of viral genomes the DNA Hirt extraction process (Hirt B et al., "Selective extraction of polyoma DNA from infected mouse cell cultures", *J Mol Biol*—1967, vol 26, pp: 365-369) was conducted, allowing isolation of viral episomes from the inside cells. Quantitative PCR was carried out with specific primers for CMV IE promoter. Primers used to detect by quantitative PCR (qPCR) levels of s-KL were:

```
s-KL-forward
                                  (SEQ ID NO: 9)
5'-TGGCTTTCCTCCTTTACCTG-3', s-KL-reverse
                                  (SEQ ID NO: 10)
5'-GCCGACACTGGGTTTTGT-3', CMV-Fwd:
                                  (SEQ ID NO: 18)
5'-TACATAACTTACGGTAAATGGC-3'
and, CMV-Rev:
                                  (SEQ ID NO: 19)
5'-AAAGTCCCTATTGGCGTTACT-3'.
```

Viral expression was conducted by extracting RNA from the brain sections. qPCR was carried out following suppliers instructions with iTaq Universal SYBR Green Supermix (BioRad), the thermocycler CFX384 Touch™ Real-Time PCR Detection System (BioRad), Hard-Shell Rhin-Wall 384-Weel Skirted PCR Plates (BioRad), Microseal "B" Adhesive Seals (BioRad). cDNA was diluted 1/5. Amplification program was of 98° C. for 2 minutes, 40 cycles at 95° C. for 5 seconds and 58° C. for 30 seconds.

Figure 6:
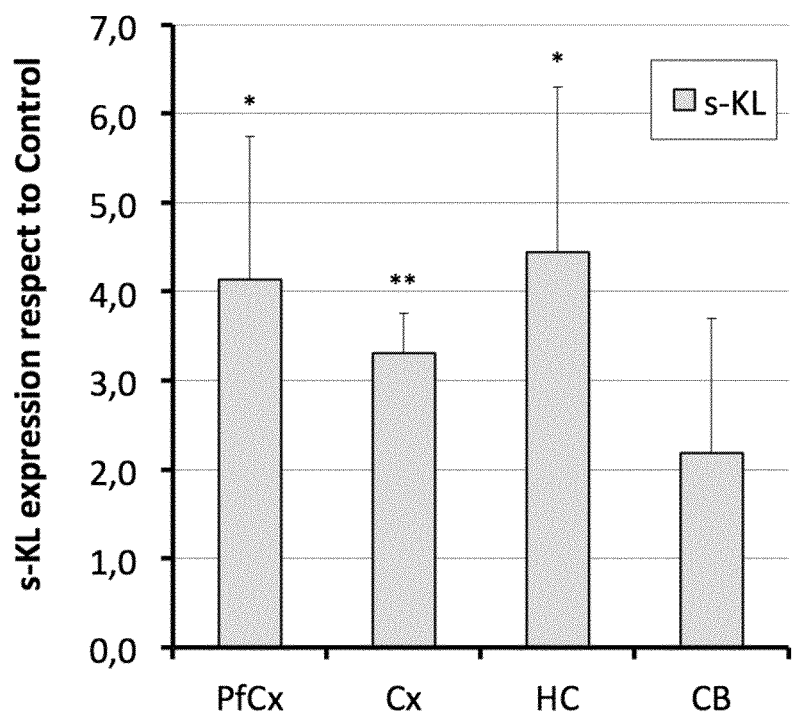
FIG. 6 shows relative expression in relation to controls of s-KL in several brain parts or sections (Prefrontal cortex, PFC; cortex, C; hippocampus, H; and cerebellum, CB) of AAV-treated animals. This figure is related to Example 2E.

AAV genomes were detected in all injected animals, AAV-s-KL distributed similarly to AAV-Null control (data not shown). Thus 6 months after intraventricular administration, AAVrh10 vector was still present in the CNS of 18 month-old mice. More importantly, s-KL expression was increased in all the brain areas analyzed (by qPCR on s-KL mRNA), ranging from 2 times higher in cerebellum to 4 times in prefrontal cortex and hippocampus (FIG. 6). These results confirm that the differences in the behaviour and cognitive tests disclosed above for old mice where due to s-klotho over-expression.

Example 3. In Vivo Administration of s-KL in Young Mice

In order to study whether long-term expression of s-KL could improve the physical, non-cognitive and cognitive status of middle-aged animals, a second set of mice (n=11-14) was treated at 6 months of age. They were then assessed at 12 months by the same battery of tests. There is a much lower efficiency of AAV transduction in older compared to younger brains. By testing a group of relatively younger adult animals, we could avoid this limitation. In addition, for this group AAV was specifically injected into the hippocampus. The main reasons were (i) the klotho gene is abundantly expressed in hippocampus; (ii) hippocampus is involved in learning and memory processes; and (iii) in mice, the hippocampus develops structurally until 12 months of age, later undergoing age-dependent functional decline. Actually, there are other brain regions where klotho is also highly expressed (e.g. plexus choroide, and cerebellum). However, we were interested to see if specifically enhancing s-KL in the hippocampus during a period of plasticity, would improve hippocampal-dependent learning and memory processes and thereby reduce the future impact of functional decline.

In the same experimental design, we also compared whether s-KL inhibition worsened cognitive deficits in naive mice, with respect to control-treated and s-KL treated animals. To achieve specific inhibition of the secreted Klotho isoform, we administered AAV vectors carrying shRNA against s-KL. The shRNA sequence was designed against the extra sequence in the tail of s-KL not present in m-KL. An AAV carrying a shRNA-scrambled sequence was used as a control.

Example 3A. Administration of AA Vectors

In vivo assay was performed as in Example 2, but with young animals (6-months old when injected with the AAV vectors comprising coding sequences for s-KL, or scramble DNA as control). In this case animals were injected in hippocampus (2 injections of $5 \times 10^9$ vg/mouse, one injection per hemisphere). Animal body weight was measured at the beginning of the experiment (6 months), at 9 and 12 months of age. The same behaviour and cognitive tests were conducted when mice were 12-months old. As in Example 2, weight (monthly determined) was increased during the assay, as expected. Of note, sustained overexpression or inhibition of s-KL over time had no significant effect and all groups showed a steady, similar weight gain (data not shown).

TABLE 4

| Sensorimotor functions | | |
|---|---|---|
| | Null | s-KL |
| Visual reflex (Extension of extremities when mice are approximated to a black panel while being hanged through the tail. If done punctuation of "1" is accorded) | 3/3 | 3/3 |
| Wooden bar (Latency to fall down, in seconds, of a 40 cm high suspended bar) | 14.45 ± 1.95 | 17.92 ± 1.16 |
| Metallic bar (Latency to fall down, in seconds, of a 40 cm high suspended bar) | 9.09 ± 1.86 | 6.85 ± 1.27 |
| Hanger (Latency to fall down, in seconds, of a 60 cm high suspended hanger, where mice are hanged by means of frontal extremities) | 34.36 ± 7.04 | 39.57 ± 5.84 |

Likewise in the previous experiment with older animals, sustained overexpression or inhibition of s-KL from 6 to 12 months of age did not affect the reflexes and sensorimotor skills of all groups, the reflexes and sensorimotor skills of all groups were not affected (Table 4).

Figure 7:
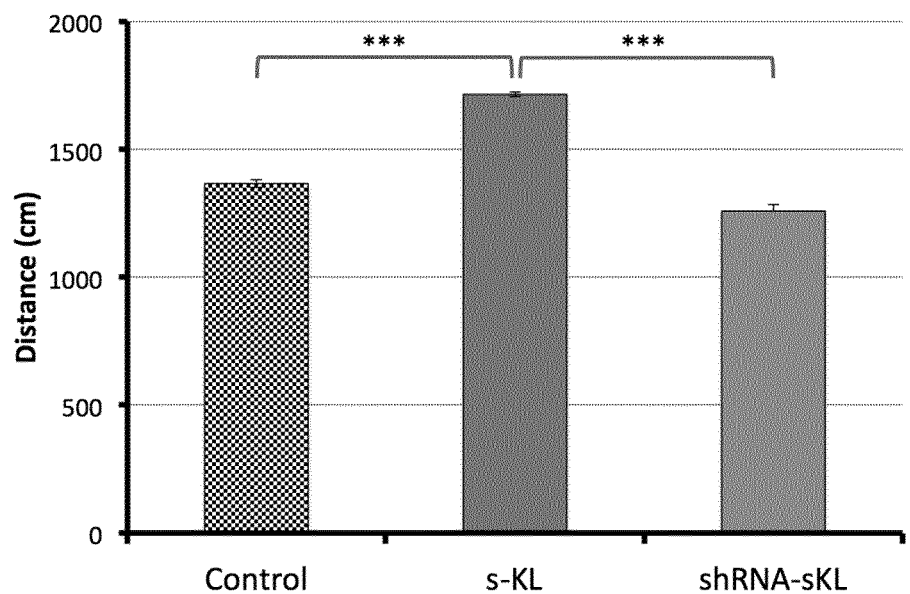
FIG. 7 (A, B) shows, respectively, the total distance (cm) in open field test made by s-KL, shRNA-sKL and Control, 12-months old mice (panel A); the total distance (cm) made per minute for each type of mouse (panel B), recorded during one minute (in X-axe, MIN is the minute 1 to 5 of assay, squares for Null, triangles for shRNA-sKL and circles for s-KL); and different parameters to evaluate the exploratory activity in the open field test. (panel C). This figure is related to Example 3B.
Figure 7:
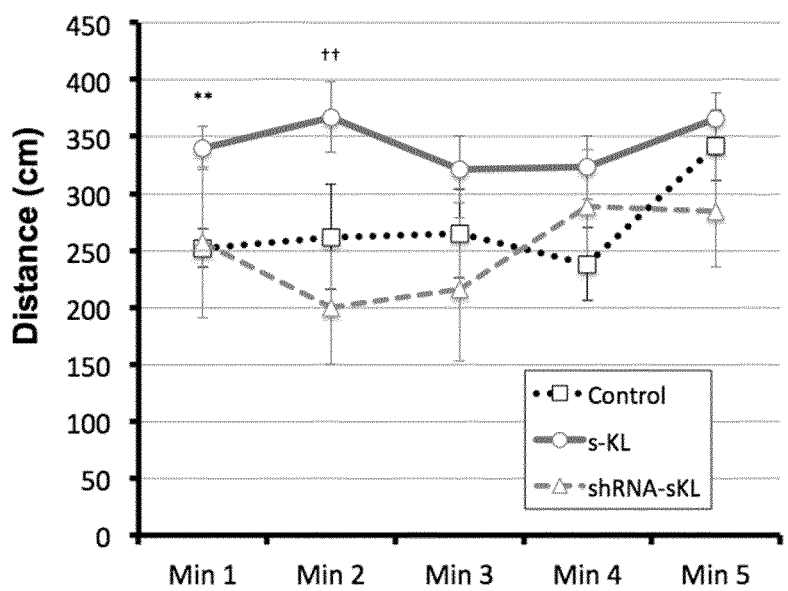

Example 3B. Hippocampal s-KL Overexpression Results in an Increase in Horizontal Activity and has a Mild Anxiolytic Effect in Middle-Aged Adult Mice In the open field test (FIG. 7) it could also be observed that over-expression of klotho induced changes in spontaneous activity in relation to wild-type mice. Consistent with previous results in aged mice, modification of s-KL levels by gene therapy approaches was able to change horizontal locomotor activity (FIG. 7A, 7B), but not the vertical activity (data not shown) of mice in the open field test. Thus, when s-KL cDNA was overexpressed in hippocampus, the total distance travelled by mice was significantly higher than in the other two groups (p<0.0001) (Control: 1365±14 cm;

s-KL: 1734±8 cm; shRNA/s-KL: 1259±27. cm). On the other hand, during the first minute of the test, some control animals froze for a while which is a direct measure of increased anxiety. In the case of mice overexpressing s-KL, a shorter latency to leave the central area was recorded although this difference was only statistically significant with respect to shRNA-sKL injected mice (p=0.0008) (Table 5). No differences were detected between the groups in the other variables analysed.

TABLE 5

Exploratory activity in the open field test

| | Control | s-KL | shRNA-sKL |
|---|---|---|---|
| Latency to leave the center(s) | 5.18 ± 1.60 | 3.00 ± 0.97*** | 8.00 ± 0.78 |
| Latency to arrive to periphery (s) | 9.12 ± 1.57 | 7.33 ± 1.22 | 10.34 ± 1.09 |
| Latency first rearing (s) | 27.63 ± 3.96 | 26.92 ± 4.08 | 23.80 ± 2.74 |
| Number of groomings | 1.81 ± 0.42 | 1.42 ± 0.32 | 1.81 ± 0.31 |
| Latency first grooming (s) | 115.54 ± 25.49 | 164.92 ± 23.16 | 112.36 ± 18.43 |
| Number of defecations | 2.33 ± 0.47 | 1.96 ± 0.35 | 2.4 ± 0.40 |

Example 3C. Hippocampal s-KL Overexpression Improves Cognitive Performance in Middle-Aged Adult Mice, while s-KL Inhibition Impairs it When working memory is evaluated in T Maze test, also meaningful differences are observed between treated and control animals.

Results are presented as the mean values obtained for each of the three test days. First, in the forced-choice trial, all control animals and those overexpressing s-KL were able to meet the criteria. On the contrary, about 10% of shRNA-sKL treated animals did not, and therefore were discarded. In addition, in the first trial, mice overexpressing s-KL needed less time to reach the intersection point of the maze compared to mice injected with shRNA-sKL (p=0.009) (Table 6). Thereafter, in the free-choice trial, all animals met all the established criteria, but differences between groups were observed in terms of efficiency in choosing the correct path. The control group solved the task with an error rate of 36.36%. This score was improved in the s-KL overexpression group with an error rate of 21.42%. In contrast silencing s-KL increased the percentage of error up to 40% (Table 6).

TABLE 6

Different parameters in the forced choice and free-choice trial of a T-maze test performed in control, s-KL, and shRNA-sKL mice

| | Control | s-KL | shRNA-sKL |
|---|---|---|---|
| Forced choice in T-maze | | | |
| T-intersection (latency, s) | 8.48 ± 1.77 | 5.29 ± 1.29** | 10.28 ± 1.11 |
| Criteria Achievement (frequency/total n) | 11/11 | 14/14 | 10/11 |
| Exploration criteria (latency, s) | 72.15 ± 5.41 | 50.47 ± 4.38 | 57.27 ± 5.24 |
| Memory Assay in T-maze | | | |
| Criteria achievement (frequency/total n) | 11/11 | 14/14 | 10/11 |
| Errors (frequency/total n) | 4/11 | 3/14 | 4/10 |

Finally in the Morris Water Maze test, during the cue learning task latency no meaningful differences were observed, probably due to the mice being young.

In the place task all groups showed a learning curve while training was performed, seen as a lower distance to get the platform. In relation to controls, m-KL and s-KL mice had a faster learning curve day by day.

In the memory tests, 2 hours after the last cue assay, platform was removed and mice were evaluated to see if they could remember where the platform was. This was done determining the distance mice made in the square where the platform was (PTf), the distance in the opposite square (Opos PTf), in the right platform square (R PTf), and in the left platform square (L PTf). Data are not shown but all groups (null, and s-KL) were able to prioritize PTf square.

Figure 8:
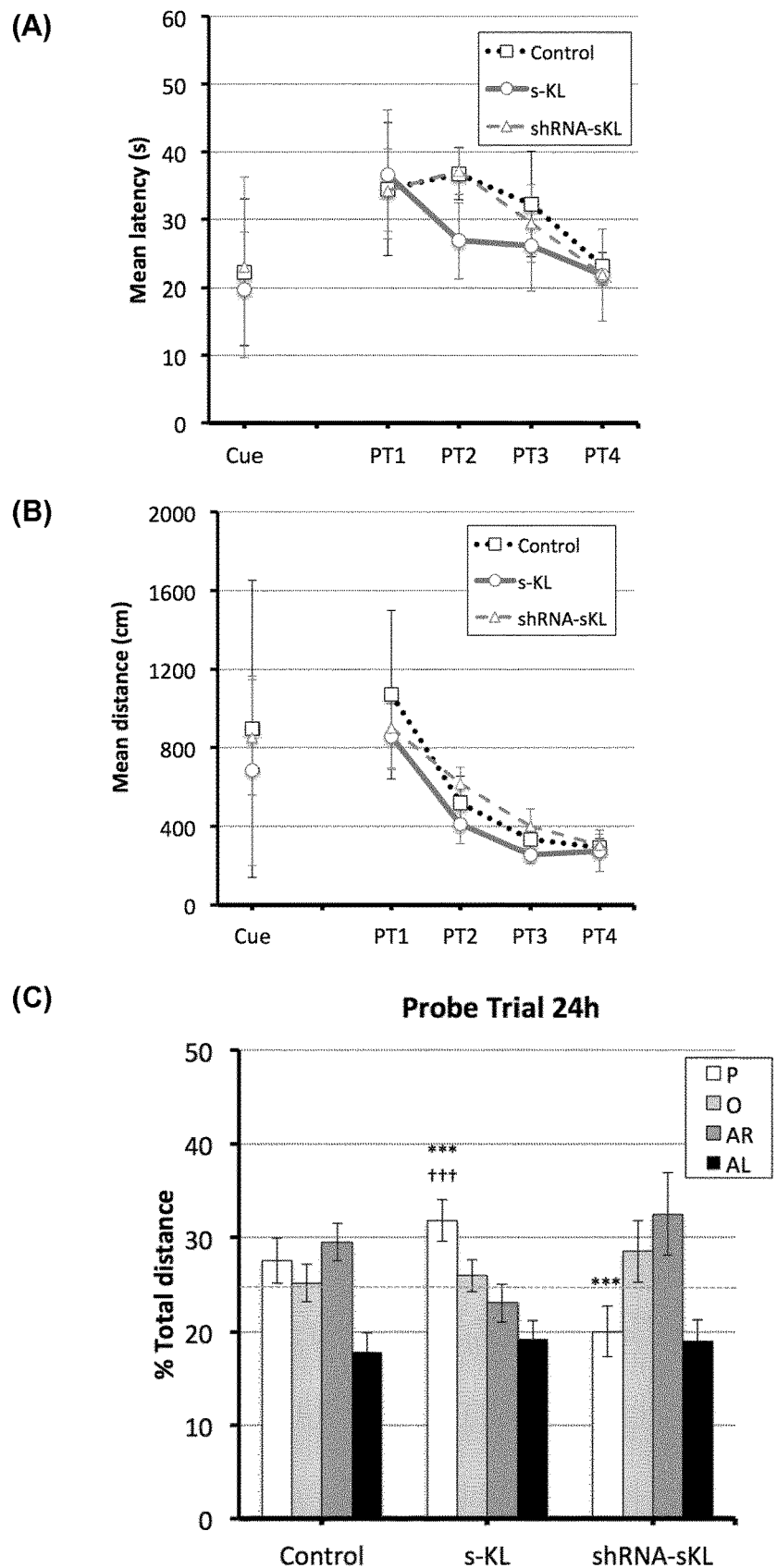
FIG. 8 depicts the results of a Morris Water Maze test performed in in 12-months old mice. s-KL mice (circles), shRNA-sKL mice (triangles), and Null mice (squares).

On the other hand, if the test was performed 24 hours after the last cue test (long-term memory test), klotho treated groups were able to prioritize PTf square in a more efficient way than controls (p<0.001 for s-KL injected mice). Graphic data are depicted in FIG. 8, where percentage of total distance made in each of the squares is depicted for each mouse type.

Again, it could be concluded that as in older mice, klotho treatment improved memory skills (in this case long-term memory).

Visual perceptual learning and spatial reference learning and memory were assessed in the Morris Water Maze, following the same protocol as used previously. In the Place learning Task (PT) all groups showed the capacity to learn the task, reflected by the gradual reduction in latency to reach the platform (FIG. 8A) and in distance travelled to it (FIG. 8B). Finally, a memory probe test performed 24 hours after last training session allowed us to assess the effects of s-KL in long-term memory in 12 month old mice. FIG. 9C shows that mice overexpressing s-KL have a greater preference for the training quadrant (p=0.0003 versus Control and p<0.0001 versus shRNA-sKL). As before, shRNA-sKL treated animals showed the lowest preference for the training quadrant and random preference for the other quadrants (p<0.0001 versus control animals). We therefore conclude that, as in aged animals, elevation of s-KL levels enhances the ability to discriminate the quadrants, especially at long-term. Furthermore, silencing s-KL worsens the animals' performance, confirming it has a role in cognitive functions.

Example 4. Detection of s-KL Protein Isoform with Specific Antibody

Protein extracts (15-25 μg per sample) from tissue samples were run in denaturing acrylamide gels, and then electrotransferred to PDVF membranes (GE Healthcare). Membranes were blocked with TBS-T (20 mM Tris-HCl pH 7.5, 150 mM NaCl, 0.2% Tween-20) containing 5% skimmed milk, and incubated with the primary K113 antibody. Detection was performed with an appropriate horseradish peroxidase-conjugated secondary antibody (EZBiolab, IN, USA) and enhanced chemiluminescence reagent (GE Healthcare). The K113 antibody was used at 1/5,000 dilution; KM2076 antibody was used at 1/1000; polyclonal rabbit anti-actin antibody (Sigma A2066, USA) at 1/1,000; and secondary HRP-anti-Ig antibody (Dako-Cytomation, P0399, Denmark) at 1/10,000.

As indicated above, the present invention results from inventors' determination in mouse wild-type brain tissue of the real expression at protein level (not only as mRNA) of a Klotho isoform, probably the splicing variant of mammal klotho protein.

Figure 9:
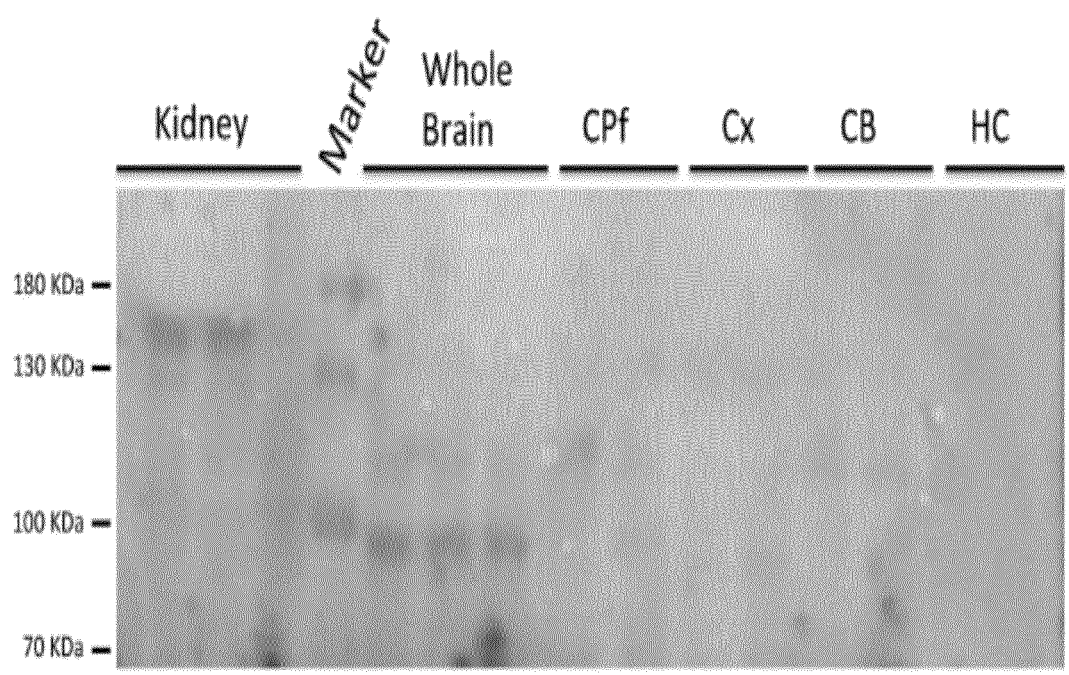
FIG. 9 is a Western blot image of an assay conducted to detect klotho protein in wild-type mice (C57Bl6) tissues with a commercial antibody (KM2076, of Cosmobio Japan): Kidney, Whole brain and particular brain sections prefrontal cortex (CPf), in cortex (Cx), cerebellum (CB), and hippocampus (HC). Klotho protein in brain had a molecular weight between 70 and 100 KDa, meanwhile in kidney the protein has a molecular weight near 130 KDa. This figure is related to Example 4.

This hypothesis results from an analysis of the klotho proteins detectable in wild-type mice tissues. Using the commercial antibody (KM2076, Cosmobio Japan) it could be determined in a Western Blot assay (FIG. 9) that in kidney the membrane isoform of 130 kDa was present, meanwhile in brain it only could be detected an isoform with a molecular weight similar to that of 70 KDa (the approximate weight of the KL1 domain of klotho or of the s-KL variant). The molecular weight of the brain detectable klotho isoform had a molecular weight between 70 KDa and 100 KDa, probably due to post-transcriptional modification in the amino acid sequence. FIG. 9 shows detection in whole brain, but also in prefrontal cortex (CPf), in cortex (Cx), cerebellum (CB), and hippocampus (HC).

Besides, in a parallel assay inventors determined with a self-made polyclonal antibody specific for mouse s-KL, if this isoform was in different brain sections. This specific polyclonal antibody (herewith named Ab K113) against s-KL was generated in rabbit by EZBiolab company (Carmel, USA) using the designed immunogenic peptide of SEQ ID NO: 11 (SPLTKPSVGLLLPH) as antigen. This sequence is not present either in m-KL o any p-KL, and it is for this reason that the antibody was specific for s-KL isoform.

Figure 10:
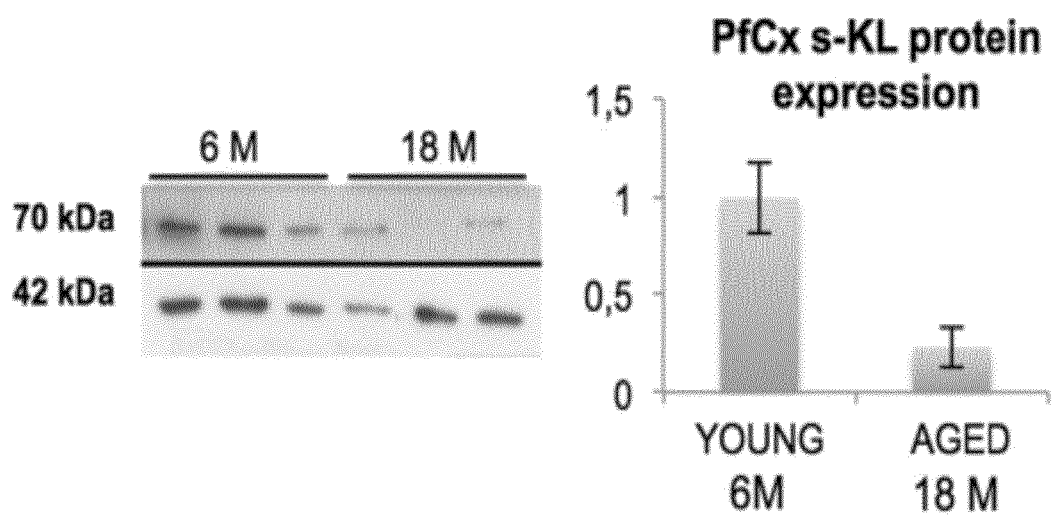
FIG. 10 (A-D) shows the analysis of the s-KL protein by Western-blot using a rabbit anti-mouse antibody (self-made and named Ab K113), raised specifically against s-KL. Prefrontal cortex (PfCx, panel (A)), cortex (CX, panel (B)), hippocampus (HC, panel (C)), and cerebellum (CB, panel (D)) of 6 and 18 months old C57Bl/6 mice (YOUNG 6M, AGED 8M). Actine (42 kDa) was used to normalize the amount of protein analyzed. Samples were quantified by densitometry using ImageJ software, the public domain, Java-based image processing program developed at the National Institute of Health. For each brain area analysed, Fold-change from 18 months-old mice relative to those obtained from 6 months-old mice are depicted in bar diagrams.
Figure 10:
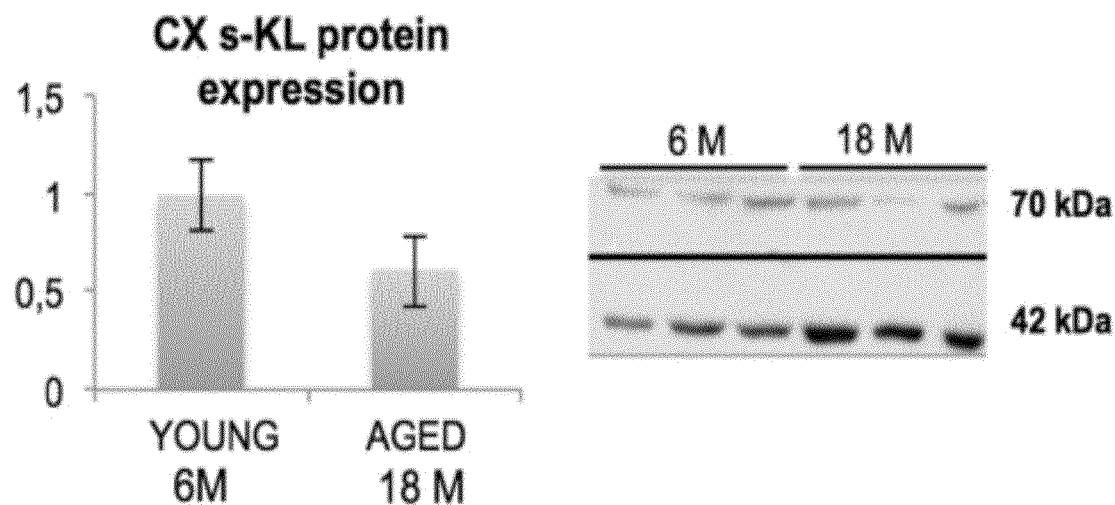

The levels of the s-KL protein were particularly analyzed in prefrontal cortex (PfCX s-KL), cortex (CX s-KL), hippocampus (HC s-KL) and cerebellum (CB s-KL) of 6 months old and 18 months-old mice using that K113 antibody. Data are depicted in FIG. 10, wherein Western-blot analysis is shown for each region together with densitometry assays (using Image J software). FIG. 10(A) depicts data from PfCX, FIG. 10(B) data from CX, FIG. 10(C) depicts data from HC and FIG. 10(D) data from CB.

All these data allow to conclude that the isoform of between 70-100 KDa detected by the commercial antibody in brain was likely s-KL, as the one specifically detected by K113 antibody of the inventors in the parallel assay of FIG. 10.

Therefore, if the variant of klotho protein that is endogenously expressed in brain is mainly s-KL, using it in the prevention and/or treatment of cognitive and/or behaviour impairment associated with aging, and/or with neurodegenerative and/or neuropathological diseases, supposes a real advantage.

First, because from the data of Examples 2 and 3 of this invention it is derived that s-KL treatment supposes amelioration skills (memory and behaviour) in relation with non-treated animals.

Second, it is known from Kurosu, et al., "Regulation of fibroblast growth factor-23 signalling by klotho", *J Biol Chem*—2006, vol 281(10), pp.: 6120-3, that m-KL acts as a co-receptor of fibroblast growth factor receptor of FGF23 (FGF23R). This receptor is involved in calcium homeostasis. Therefore, by using s-KL, with similar effects than m-KL, this will avoid any interference with calcium homeostasis, since s-KL is not a co-receptor of FGF23R.

According to inventor's knowledge, this is the first time s-KL has been administered (in this case by gene therapy) to wild-type animals (mice). It has moreover been made plausible that this protein is therapeutically effective in terms of preserving and/or ameliorating cognitive and behaviour impairments associated with aging (in particular senile dementia) and with some neurodegenerative diseases, such as Alzheimer's disease (AD). In particular, therapeutically effective in preserving impairments in memory skills, such as memory losses and anxiety, all of them usually common in old people and in AD people.

In the case of neurodegenerative diseases and neuropathological diseases, it is highly recommendable proposing s-KL as accompanying treatment, if any.

Figure 11:
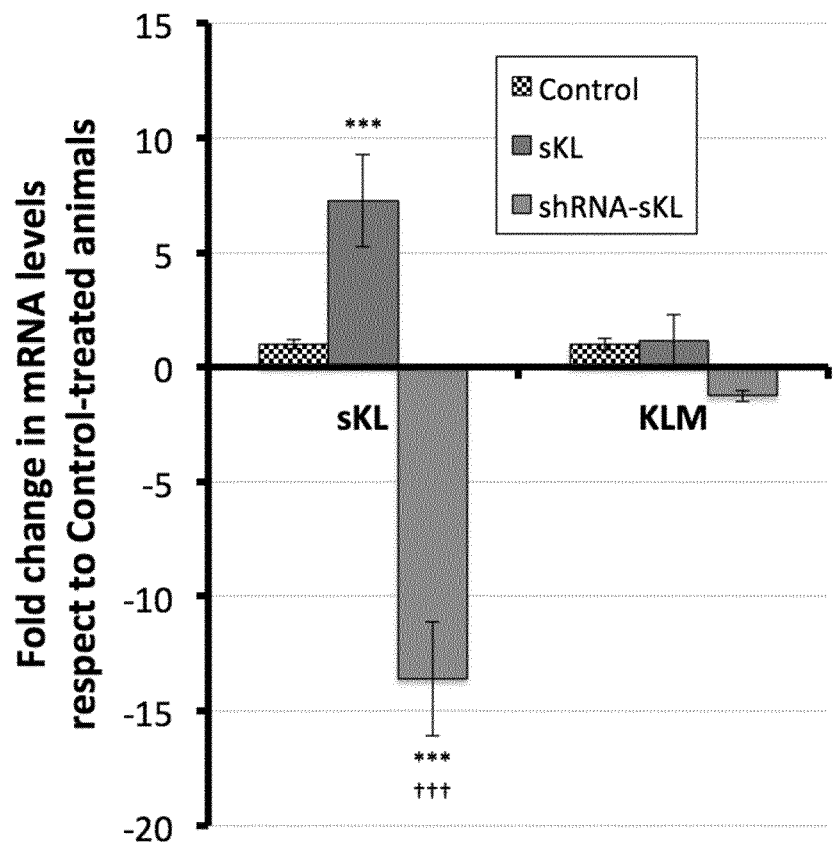
FIG. 11. s-KL and m-KL expression levels in AAV-treated mice. s-KL levels were quantified in the hippocampus of s-KL, shRNA-sKL and null treated animals 6 months after hippocampal administration. mRNA levels of s-KL and m-KL transcripts were normalized respect the values obtained in control animals. This figure is related to Example 5.

Example 5. Administration of s-KL and shRNA-sKL Expressing Vectors in Hippocampus Specifically Modifies Expression Levels of s-KL, but no m-KL s-KL levels were quantified in the hippocampus of treated animals to determine whether the effects observed in cognition were induced by s-KL overexpression and/or s-KL inhibition. Hence, mRNA levels of s-KL in the AAV/s-KL injected group were increased 7.25±2.0 times with respect to animals injected with AAV-Control (p=0.035), while in AAV/shRNA-sKL animals, s-KL expression levels were reduced by 13.6±2.5 times (p=0.007) (FIG. 11). These changes were specific to the secreted Klotho isoform since expression of the m-KL transmembrane isoform was not affected either by s-KL overexpression (1.15±1.1 times vs control), nor by specific s-KL inhibition (−1.24±0.27 times vs control).

Statistical Analysis

Values are presented as mean values±SEM. Statistical analyses and calculations were performed using the G-Stat version 2.0 and Prism 5.04 programs. Statistical analysis between individual groups was performed by two-tailed unpaired Student's t-test or one-way of variance ANOVA followed by Tukey post-hoc test. In all cases differences in means were considered statistically significant if $p<0.05$.

REFERENCES CITED IN THE APPLICATION

Deary et al., "Klotho genotype and cognitive ability in childhood and old age in the same individuals", *Neurosci Lett*—2005, vol. 378(1), pp. 22-27.

Kuro-o, et al., Mutation of the mouse klotho gene leads to a syndrome resembling ageing. *Nature*—1997, vol. no. 390, pp.: 45-51.

Wang, Y. et al, "Current understanding of klotho", Ageing Res Rev-2009, vol. no. 8, pp.: 43-511.

Matsumura et al., "Identification of the human klotho gene and its two transcripts encoding membrane and secreted Klotho protein", *Biochem Biophys Res Commun*—1998, vol. No. 242, pp.: 626-630.

Dubal et al., "Life Extension Klotho Enhances Cognition", *Cell Reports* 2014, vol. 7, pp.: 1065-1076.

Dubal et al., Life Extension factor Klotho Prevents Mortality and Enhances Cognition in hAPP Transgenic Mice", *The Journal of Neuroscience*—2015, vol. 35/6, pp.: 2358-2371.

Kuang et al., "Klotho upregulation contributes to the neuroprotection of ligustilide in an Alzheimer's disease mouse model", *Neurobiology of Aging*—2013, pp. 1-10.

Forster et al. "Vitamin D Receptor Controls Expression of the Anti-aging Klotho Gene in Mouse and Human Renal Cells" Biochem Biophys Res Commun. 2011 Oct. 28; 414(3): 557-562.

Shiraki-lida et al., "Structure of the mouse klotho gene and its two transcripts encoding membrane and secreted protein", FEBS Letters—1998, vol 424, pp.: 6-10.

Imura et al., "Secreted Klotho protein in sera and CSF: implication for post-translational cleavage in release of Klotho protein from cell membrane", FEBS Letters—2001, vol 565, pp.: 143-147.

Altschul, S. F., et al. "Gapped BLAST and PSI-BLAST: a new generation of proteina database search programnns", Nucleic Acids Research—1997 Vol. No. 25, pp.: 3389-3402.

Piedra et al., "Development of a rapid, robust, and universal picogreen-based method to titer adeno-associated vectors", *Hum Gene Ther Methods*—2015, vol 26(1), pp: 35-42; or doi: 10.1089/hgtb.2014.120 PMID: 25640021.

Hirt B et al., "Selective extraction of polyoma DNA from infected mouse cell cultures", *J Mol Biol*—1967, vol 26, pp: 365-369.

Kurosu, et al., "Regulation of fibroblast growth factor-23 signaling by klotho", *J Biol Chem*—2006, vol 281(10), pp.: 6120-3.

The invention claimed is:

1. A method for the treatment of a cognitive impairment disease in a mammal, comprising administering to the mammal, by injecting directly into the brain, by intramuscular injection, by intravenous injection, or by delivering directly into the central nervous system (CNS), a therapeutically effective amount of an adeno-associated virus expression vector with a CNS tropism comprising an expression promoter operatively linked to a nucleic acid encoding an alternative splicing variant of mammalian klotho protein consisting of the amino acid sequence of SEQ ID NO: 1 or SEQ ID NO: 2 in a pharmaceutically acceptable excipient or carrier, wherein said AAV expression vector is serotype AAVrh10 or serotype 9, and wherein said mammal is a human, a mouse, a rat, a dog, a goat or a primate.

2. The method according to claim 1, wherein said cognitive impairment disease affects memory loss or learning.

3. The method according to claim 1, wherein said cognitive impairment disease is a neurodegenerative disease.

4. The method according to claim 1, wherein said cognitive impairment disease is a neuropathological disease.

5. The method according to claim 1, wherein said cognitive impairment disease is selected from anxiety and agoraphobia.

6. The method according to claim 1, wherein said cognitive impairment disease is associated with aging.

7. The method according to claim 1, wherein said cognitive impairment disease is selected from the group consisting of Alzheimer's disease, Parkinson's disease, Huntington's disease, Amyotrophic lateral sclerosis, Creutzfeldt-Jakob disease, Multiple Sclerosis, Ataxia telangiectasia, dementia, and craniocerebral or spinal trauma.

8. The method according to claim 7, wherein the cognitive impairment disease is Alzheimer's disease.

9. The method according to claim 8, where the treatment is for Alzheimer's disease-associated anxiety.

10. The method according to claim 1, wherein said therapeutically effective amount of the AAV expression vector is administered in combination with a second active agent.

11. The method according to claim 10, wherein said second active agent is selected from the group consisting of donepezile hydrochloride, memantine, rivastigmine, and ligustilide.

12. The method according to claim 1, wherein the nucleic acid encodes the amino acid sequence of SEQ ID NO:1.

13. The method according to claim 12, wherein the cognitive impairment disease is Alzheimer's disease.

14. The method according to claim 13, wherein the mammal is a human.

15. The method according to claim 1, wherein the injecting directly into the brain is by intracerebroventricular injection.

16. The method according to claim 1, wherein the delivering directly into the CNS comprises intrathecal injection, intracisterna magna injection, patch, micropump or microcapsule delivery.

17. The method according to claim 7, wherein the dementia is Dementia with Lewy bodies, post stroke dementia, post-traumatic dementia, or senile dementia.

18. A method for improving cognition performance in a mammal, comprising administering to the mammal, by injecting directly into the brain, by intramuscular injection, by intravenous injection, or by delivering directly into the CNS, a therapeutically effective amount of an adeno-associated virus expression vector with a CNS tropism comprising an expression promoter operatively linked to a nucleic acid encoding an alternative splicing variant of mammalian klotho protein consisting of the amino acid sequence of SEQ ID NO: 1 or SEQ ID NO: 2 in a pharmaceutically acceptable excipient or carrier, wherein said AAV expression vector is serotype AAVrh10 or serotype 9, and wherein said mammal is a human, a mouse, a rat, a dog, goat or a primate.

19. A method for treatment of cognitive decline in a mammal, comprising administering to the mammal, by injecting directly into the brain, by intramuscular injection, by intravenous injection, or by delivering directly into the CNS, a therapeutically effective amount of an adeno-associated virus expression vector with a CNS tropism comprising an expression promoter operatively linked to a nucleic acid encoding an alternative splicing variant of mammalian klotho protein consisting of the amino acid sequence of SEQ ID NO: 1 or SEQ ID NO: 2, in a pharmaceutically acceptable excipient or carrier, wherein said AAV expression vector is serotype AAVrh10 or serotype 9, and wherein said mammal is a human, a mouse, a rat, a dog, a goat or a primate.

20. The method according to claim 1, wherein the AAV expression vector is an adeno-associated virus of serotype AAV9.

21. The method according to claim 18, wherein the AAV expression vector is an adeno-associated virus of serotype AAV9.

22. The method according to claim 19, wherein the AAV expression vector is an adeno-associated virus of serotype AAV9.

23. The method according to claim 18, wherein said mammal is a human.

24. The method according to claim 19, wherein said mammal is a human.

25. The method according to claim 7, wherein the cognitive impairment disease is Parkinson's disease.

26. The method according to claim 25, wherein the mammal is a human.

27. The method of claim 26, wherein the nucleic acid encodes the amino acid sequence of SEQ ID NO:1.

28. The method according to claim 7, wherein the cognitive impairment disease is Amyotrophic lateral sclerosis.

29. The method according to claim 28, wherein the mammal is a human.

30. The method of claim 29, wherein the nucleic acid encodes the amino acid sequence of SEQ ID NO:1.

31. The method of claim 23, wherein the nucleic acid encodes the amino acid sequence of SEQ ID NO:1.

32. The method of claim 24, wherein the nucleic acid encodes the amino acid sequence of SEQ ID NO:1.

* * * * *

SEQUENCE LISTING

<160> NUMBER OF SEQ ID NOS: 19

<210> SEQ ID NO 1
<211> LENGTH: 549
<212> TYPE: PRT
<213> ORGANISM: Homo sapiens

<400> SEQUENCE: 1

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Val Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270
```

```
Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
            370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
            450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
            515                 520                 525

Asp Asn Tyr Ile Gln Val Ser Gln Leu Thr Lys Pro Ile Ser Ser Leu
            530                 535                 540

Thr Lys Pro Tyr His
545

<210> SEQ ID NO 2
<211> LENGTH: 550
<212> TYPE: PRT
<213> ORGANISM: Mus musculus

<400> SEQUENCE: 2

Met Leu Ala Arg Ala Pro Pro Arg Arg Pro Arg Leu Val Leu Leu
1               5                   10                  15

Arg Leu Leu Leu Leu His Leu Leu Leu Leu Ala Leu Arg Ala Arg Cys
            20                  25                  30

Leu Ser Ala Glu Pro Gly Gln Gly Ala Gln Thr Trp Ala Arg Phe Ala
            35                  40                  45

Arg Ala Pro Ala Pro Glu Ala Ala Gly Leu Leu His Asp Thr Phe Pro
        50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95
```

```
His His Ser Gly Ala Ala Pro Ser Asp Ser Pro Ile Val Val Ala Pro
            100                 105                 110

Ser Gly Ala Pro Ser Pro Pro Leu Ser Ser Thr Gly Asp Val Ala Ser
            115                 120                 125

Asp Ser Tyr Asn Asn Val Tyr Arg Asp Thr Glu Gly Leu Arg Glu Leu
            130                 135                 140

Gly Val Thr His Tyr Arg Phe Ser Ile Ser Trp Ala Arg Val Leu Pro
145                     150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
            180                 185                 190

Leu Tyr His Trp Asp Leu Pro Gln Arg Leu Gln Asp Thr Tyr Gly Gly
            195                 200                 205

Trp Ala Asn Arg Ala Leu Ala Asp His Phe Arg Asp Tyr Ala Glu Leu
210                 215                 220

Cys Phe Arg His Phe Gly Gly Gln Val Lys Tyr Trp Ile Thr Ile Asp
225                     230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
            260                 265                 270

Leu Leu Leu Ala His Ala Lys Val Trp His Leu Tyr Asn Thr Ser Phe
            275                 280                 285

Arg Pro Thr Gln Gly Gly Arg Val Ser Ile Ala Leu Ser Ser His Trp
            290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
            340                 345                 350

Asp Phe Thr Glu Ser Glu Lys Arg Leu Ile Arg Gly Thr Ala Asp Phe
            355                 360                 365

Phe Ala Leu Ser Phe Gly Pro Thr Leu Ser Phe Gln Leu Leu Asp Pro
370                 375                 380

Asn Met Lys Phe Arg Gln Leu Glu Ser Pro Asn Leu Arg Gln Leu Leu
385             390                 395                 400

Ser Trp Ile Asp Leu Glu Tyr Asn His Pro Ile Phe Ile Val Glu
                405                 410                 415

Asn Gly Trp Phe Val Ser Gly Thr Thr Lys Arg Asp Asp Ala Lys Tyr
                420                 425                 430

Met Tyr Tyr Leu Lys Lys Phe Ile Met Glu Thr Leu Lys Ala Ile Arg
            435                 440                 445

Leu Asp Gly Val Asp Val Ile Gly Tyr Thr Ala Trp Ser Leu Met Asp
            450                 455                 460

Gly Phe Glu Trp His Arg Gly Tyr Ser Ile Arg Arg Gly Leu Phe Tyr
465             470                 475                 480

Val Asp Phe Leu Ser Gln Asp Lys Glu Leu Leu Pro Lys Ser Ser Ala
                485                 490                 495

Leu Phe Tyr Gln Lys Leu Ile Glu Asp Asn Gly Phe Pro Pro Leu Pro
            500                 505                 510
```

-continued

```
Glu Asn Gln Pro Leu Glu Gly Thr Phe Pro Cys Asp Phe Ala Trp Gly
        515                 520                 525

Val Val Asp Asn Tyr Val Gln Val Ser Pro Leu Thr Lys Pro Ser Val
    530                 535                 540

Gly Leu Leu Leu Pro His
545                 550

<210> SEQ ID NO 3
<211> LENGTH: 3024
<212> TYPE: DNA
<213> ORGANISM: Artificial
<220> FEATURE:
<223> OTHER INFORMATION: Gene construct comprising nucleotide sequence
      coding for Mus musculus klotho secreted splicing variant

<400> SEQUENCE: 3
```

| | |
|---|---:|
| tctagacatg gctcgacaga tctcaatatt ggccattagc catattattc attggttata | 60 |
| tagcataaat caatattggc tattggccat tgcatacgtt gtatctatat cataatatgt | 120 |
| acatttatat tggctcatgt ccaatatgac cgccatgttg gcattgatta ttgactagtt | 180 |
| attaatagta atcaattacg gggtcattag ttcatagccc atatatggag ttccgcgtta | 240 |
| cataacttac ggtaaatggc ccgcctggct gaccgcccaa cgacccccgc ccattgacgt | 300 |
| caataatgac gtatgttccc atagtaacgc caatagggac tttccattga cgtcaatggg | 360 |
| tggagtattt acggtaaact gcccacttgg cagtacatca agtgtatcat atgccaagtc | 420 |
| cgccccctat tgacgtcaat gacggtaaat ggcccgcctg gcattatgcc cagtacatga | 480 |
| ccttacggga ctttcctact tggcagtaca tctacgtatt agtcatcgct attaccatgg | 540 |
| tgatgcggtt ttggcagtac accaatgggc gtggatagcg gtttgactca cggggatttc | 600 |
| caagtctcca ccccattgac gtcaatggga gtttgttttg gcaccaaaat caacgggact | 660 |
| ttccaaaatg tcgtaacaac tgcgatcgcc cgccccgttg acgcaaatgg gcggtaggcg | 720 |
| tgtacggtgg gaggtctata taagcagagc tcgtttagtg aaccgtcaga tcactagaag | 780 |
| ctttattgcg gtagtttatc acagttaaat tgctaacgca gtcagtgctt ctgacacaac | 840 |
| agtctcgaac ttaagctgca gtgactctct taaggtagcc ttgcagaagt tggtcgtgag | 900 |
| gcactgggca ggtaagtatc aaggttacaa gacaggttta aggagaccaa tagaaactgg | 960 |
| gcttgtcgag acagagaaga ctcttgcgtt tctgataggc acctattggt cttactgaca | 1020 |
| tccactttgc ctttctctcc acaggtgtcc actcccagtt caattacagc tcttaaggct | 1080 |
| agagtactta atacgactca ctataggcta gcaatgctcg cccgcgcccc tcctcgccgc | 1140 |
| ccgccgcggc tggtgctgct ccgtttgctg ttgctgcatc tgctgctgct cgccctgcgc | 1200 |
| gcccgctgcc tgagcgctga gccgggtcag ggcgcgcaga cctgggctcg cttcgcgcgc | 1260 |
| gctcctgccc cagaggccgc tggcctcctc cacgacacct tccccgacgg tttcctctgg | 1320 |
| gcggtaggca gcgccgccta tcagaccgag ggcggctggc gacagcacgg caaaggcgcg | 1380 |
| tccatctggg acactttcac ccatcactct ggggcggccc cgtccgactc cccgatcgtc | 1440 |
| gtggcgccgt cgggtgcccc gtcgcctccc ctgtcctcca ctggagatgt ggccagcgat | 1500 |
| agttacaaca acgtctaccg cgacacagag gggctgcgcg aactgggggt cacccactac | 1560 |
| cgcttctcca tatcgtgggc gcgggtgctc cccaatggca ccgcgggcac tcccaaccgc | 1620 |
| gagggggctgc gctactaccg gcggctgctg agcggctgcg gggagctggg cgtgcagccg | 1680 |
| gtggttaccc tgtaccattg ggacctgcca cagcgcctgc aggacaccta tggcggatgg | 1740 |
| gccaatcgcg ccctggccga ccatttcagg gattatgccg agctctgctt ccgccacttc | 1800 |

```
ggtggtcagg tcaagtactg gatcaccatt gacaacccct acgtggtggc ctggcacggg    1860
tatgccaccg ggcgcctggc cccgggcgtg aggggcagct ccaggctcgg gtacctggtt    1920
gcccacaacc tacttttggc tcatgccaaa gtctggcatc tctacaacac ctctttccgc    1980
cccacacagg gaggccgggt gtctatcgcc ttaagctccc attggatcaa tcctcgaaga    2040
atgactgact ataatatcag agaatgccag aagtctcttg actttgtgct aggctggttt    2100
gccaaaccca tatttattga tggcgactac ccagagagta tgaagaacaa cctctcgtct    2160
cttctgcctg attttactga atctgagaag aggctcatca gaggaactgc tgactttttt    2220
gctctctcct tcggaccaac cttgagcttt cagctattgg accctaacat gaagttccgc    2280
caattggagt ctcccaacct gaggcagctt ctgtcttgga tagatctgga atataaccac    2340
cctccaatat ttattgtgga aaatggctgg tttgtctcgg aaccaccaa aagggatgat    2400 gccaaatata tgtattatct caagaagttc ataatggaaa ccttaaaagc aatcagactg    2460 gatgggtcg acgtcattgg gtacaccgcg tggtcgctca tggacggttt cgagtggcat    2520
aggggctaca gcatccggcg aggactcttc tacgttgact ttctgagtca ggacaaggag    2580
ctgttgccaa agtcttcggc cttgttctac caaaagctga tagaggacaa tggctttcct    2640
cctttacctg aaaaccagcc ccttgaaggg acatttccct gtgactttgc ttggggagtt    2700
gttgacaact acgttcagct gagtcctttg acaaaaccca gtgtcggcct cttgcttcct    2760
cactaagggc cgcttccctt tagtgagggt taatgcttcg agcagacatg ataagataca    2820
ttgatgagtt tggacaaacc acaactagaa tgcagtgaaa aaaatgcttt atttgtgaaa    2880
tttgtgatgc tattgcttta tttgtaacca ttataagctg caataaacaa gttaacaaca    2940
acaattgcat tcattttatg tttcaggttc aggggagat gtgggaggtt ttttaaagca    3000
agtaaaacct ctacaaatgt ggta                                            3024
```

<210> SEQ ID NO 4
<211> LENGTH: 3018
<212> TYPE: DNA
<213> ORGANISM: Artificial
<220> FEATURE:
<223> OTHER INFORMATION: Gene construct comprising nucleotide sequence
      coding for Homo sapiens klotho secreted splicing variant

<400> SEQUENCE: 4

```
tctagacatg gctcgacaga tctcaatatt ggccattagc catattattc attggttata     60
tagcataaat caatattggc tattggccat tgcatacgtt gtatctatat cataatatgt    120
acatttatat tggctcatgt ccaatatgac cgccatgttg gcattgatta ttgactagtt    180
attaatagta atcaattacg gggtcattag ttcatagccc atatatggag ttccgcgtta    240
cataacttac ggtaaatggc ccgcctggct gaccgcccaa cgacccccgc ccattgacgt    300
caataatgac gtatgttccc atagtaacgc caatagggac tttccattga cgtcaatggg    360
tggagtattt acggtaaact gcccacttgg cagtacatca agtgtatcat atgccaagtc    420
cgccccctat tgacgtcaat gacggtaaat ggcccgcctg gcattatgcc cagtacatga    480
ccttacggga ctttcctact tggcagtaca tctacgtatt agtcatcgct attaccatgg    540
tgatgcggtt ttggcagtac accaatgggc gtggatagcg gtttgactca cggggatttc    600
caagtctcca ccccattgac gtcaatggga gtttgttttg gcaccaaaat caacgggact    660
ttccaaaatg tcgtaacaac tgcgatcgcc cgccccgttg acgcaaatgg gcggtaggcg    720
tgtacggtgg gaggtctata taagcagagc tcgtttagtg aaccgtcaga tcactagaag    780
```

```
ctttattgcg gtagtttatc acagttaaat tgctaacgca gtcagtgctt ctgacacaac    840
agtctcgaac ttaagctgca gtgactctct taaggtagcc ttgcagaagt tggtcgtgag    900
gcactgggca ggtaagtatc aaggttacaa gacaggttta aggagaccaa tagaaactgg    960
gcttgtcgag acagagaaga ctcttgcgtt tctgataggc acctattggt cttactgaca   1020
tccactttgc ctttctctcc acaggtgtcc actcccagtt caattacagc tcttaaggct   1080
agagtactta atacgactca ctataggcta gcaatgcccg ccagcgcccc gccgcgccgc   1140 cgcggccgc cgccgccgtc gctgtcgctg ctgctggtgc tgctgggcct gggcggccgc    1200
cgcctgcgtg cggagccggg cgacggcgcg cagacctggg cccgtgtctc gcggcctcct   1260
gcccccgagg ccgcgggcct cttccagggc accttccccg acggcttcct ctgggccgtg   1320
ggcagcgccg cctaccagac cgagggcggc tggcagcagc acggcaaggg tgcgtccatc   1380
tgggacacgt tcacccacca ccccctggca ccccgggag actcccggaa cgccagtctg     1440
ccgttgggcg cccgtcgcc gctgcagccc gccaccgggg acgtagccag cgacagctac    1500
aacaacgtct tccgcgacac ggaggcgctg cgcgagctcg gggtcactca ctaccgcttc   1560
tccatctcgt gggcgcgagt gctccccaat ggcagcgcgg cgtccccaa ccgcgagggg    1620 ctgcgctact accggcgcct gctggagcgg ctgcgggagc tgggcgtgca gcccgtggtc   1680
accctgtacc actgggacct gcccccagcgc ctgcaggacg cctacggcgg ctgggccaac   1740
cgcgccctgg ccgaccactt cagggattac gcggagctct gcttccgcca cttcggcggt   1800
caggtcaagt actggatcac catcgacaac ccctacgtgg tggcctggca cggctacgcc   1860
accgggcgcc tggccccgg catccggggc agcccgcggc tcgggtacct ggtggcgcac   1920
aacctcctcc tggctcatgc caaagtctgg catctctaca atacttcttt ccgtcccact   1980
cagggaggtc aggtgtccat tgccctaagc tctcactgga tcaatcctcg aagaatgacc   2040
gaccacagca tcaaagaatg tcaaaaatct ctggactttg tactaggttg gtttgccaaa   2100
cccgtattta ttgatggtga ctatcccgag agcatgaaga ataacctttc atctattctg   2160 cctgattta ctgaatctga gaaaaagttc atcaaaggaa ctgctgactt ttttgctctt    2220
tgctttggac ccaccttgag ttttcaactt ttggaccctc acatgaagtt ccgccaattg   2280
gaatctccca acctgaggca actgctttcc tggattgacc ttgaatttaa ccatcctcaa   2340
atatttattg tggaaaatgg ctggtttgtc tcagggacca ccaagagaga tgatgccaaa   2400
tatatgtatt acctcaaaaa gttcatcatg gaaaccttaa aagccatcaa gctggatggg   2460
gtggatgtca tcgggtatac cgcatggtcc ctcatggatg gtttcgagtg gcacagaggt   2520
tacagcatca ggcgtggact cttctatgtt gactttctaa gccaggacaa gatgttgttg   2580
ccaaagtctt cagccttgtt ctaccaaaag ctgatagaga aaaatggctt ccctccttta   2640
cctgaaaatc agcccctaga agggacattt ccctgtgact ttgcttgggg agttgttgac   2700
aactacattc agctgagtcc tttgacaaaa cccagtgtcg gcctcttgct tcctcactaa   2760
gggccgcttc cctttagtga gggttaatgc ttcgagcaga catgataaga tacattgatg   2820
agtttggaca aaccacaact agaatgcagt gaaaaaaatg ctttatttgt gaaatttgtg   2880
atgctattgc tttatttgta accattataa gctgcaataa acaagttaac aacaacaatt   2940
gcattcattt tatgtttcag gttcaggggg agatgtggga ggtttttaa agcaagtaaa    3000 acctctacaa atgtggta                                                 3018
```

<210> SEQ ID NO 5

<211> LENGTH: 1650
<212> TYPE: DNA
<213> ORGANISM: Homo sapiens

<400> SEQUENCE: 5

| | | | | | |
|---|---|---|---|---|---|
| atgcccgcca | gcgccccgcc | gcgccgcccg | cggccgccgc | cgccgtcgct | gtcgctgctg | 60 |
| ctggtgctgc | tgggcctggg | cggccgccgc | ctgcgtgcgg | agccgggcga | cggcgcgcag | 120 |
| acctgggccc | gtgtctcgcg | gcctcctgcc | cccgaggccg | cgggcctctt | ccagggcacc | 180 |
| ttccccgacg | gcttcctctg | ggccgtgggc | agcgccgcct | accagaccga | gggcggctgg | 240 |
| cagcagcacg | gcaagggtgc | gtccatctgg | gacacgttca | cccaccaccc | cctggcaccc | 300 |
| ccgggagact | cccggaacgc | cagtctgccg | ttgggcgccc | cgtcgccgct | gcagcccgcc | 360 |
| accggggacg | tagccagcga | cagctacaac | aacgtcttcc | gcgacacgga | ggcgctgcgc | 420 |
| gagctcgggg | tcactcacta | ccgcttctcc | atctcgtggg | cgcgagtgct | ccccaatggc | 480 |
| agcgcgggcg | tccccaaccg | cgaggggctg | cgctactacc | ggcgcctgct | ggagcggctg | 540 |
| cgggagctgg | gcgtgcagcc | cgtggtcacc | ctgtaccact | gggacctgcc | ccagcgcctg | 600 |
| caggacgcct | acggcggctg | ggccaaccgc | gccctggccg | accacttcag | ggattacgcg | 660 |
| gagctctgct | tccgccactt | cggcggtcag | gtcaagtact | ggatcaccat | cgacaacccc | 720 |
| tacgtggtgg | cctggcacgg | ctacgccacc | gggcgcctgg | cccccggcat | ccggggcagc | 780 |
| ccgcggctcg | ggtacctggt | ggcgcacaac | ctcctcctgg | ctcatgccaa | agtctggcat | 840 |
| ctctacaata | cttctttccg | tcccactcag | ggaggtcagg | tgtccattgc | cctaagctct | 900 |
| cactggatca | atcctcgaag | aatgaccgac | acacagcatca | aagaatgtca | aaaatctctg | 960 |
| gactttgtac | taggttggtt | tgccaaaccc | gtatttattg | atggtgacta | ccccgagagc | 1020 |
| atgaagaata | acctttcatc | tattctgcct | gattttactg | aatctgagaa | aaagttcatc | 1080 |
| aaaggaactg | ctgactttttt | tgctctttgc | tttggaccca | ccttgagttt | tcaactttttg | 1140 |
| gaccctcaca | tgaagttccg | ccaattggaa | tctcccaacc | tgaggcaact | gctttcctgg | 1200 |
| attgaccttg | aatttaacca | tcctcaaata | tttattgtgg | aaaatggctg | gtttgtctca | 1260 |
| gggaccacca | agagagatga | tgccaaatat | atgtattacc | tcaaaaagtt | catcatggaa | 1320 |
| accttaaaag | ccatcaagct | ggatggggtg | gatgtcatcg | ggtataccgc | atggtccctc | 1380 |
| atggatggtt | tcgagtggca | cagaggttac | agcatcaggc | gtggactctt | ctatgttgac | 1440 |
| tttctaagcc | aggacaagat | gttgttgcca | aagtcttcag | ccttgttcta | ccaaaagctg | 1500 |
| atagagaaaa | atggcttccc | tcctttacct | gaaaatcagc | ccctagaagg | gacatttccc | 1560 |
| tgtgactttg | cttggggagt | tgttgacaac | tacattcaag | taagtcagct | gacaaaacca | 1620 |
| atcagcagtc | tcaccaagcc | ctatcactag | | | | 1650 |

<210> SEQ ID NO 6
<211> LENGTH: 1653
<212> TYPE: DNA
<213> ORGANISM: Mus musculus

<400> SEQUENCE: 6

| | | | | | |
|---|---|---|---|---|---|
| atgctagccc | gcgcccctcc | tcgccgcccg | ccgcggctgg | tgctgctccg | tttgctgttg | 60 |
| ctgcatctgc | tgctgctcgc | cctgcgcgcc | cgctgcctga | gcgctgagcc | gggtcagggc | 120 |
| gcgcagacct | gggctcgctt | cgcgcgcgct | cctgccccag | aggccgctgg | cctcctccac | 180 |
| gacaccttcc | ccgacggttt | cctctgggcg | gtaggcagcg | ccgcctatca | gaccgagggc | 240 |
| ggctggcgac | agcacggcaa | aggcgcgtcc | atctgggaca | ctttcaccca | tcactctggg | 300 |

```
gcggccccgt ccgactcccc gatcgtcgtg gcgccgtcgg gtgccccgtc gcctcccctg    360
tcctccactg gagatgtggc cagcgatagt tacaacaacg tctaccgcga cacagagggg    420
ctgcgcgaac tgggggtcac ccactaccgc ttctccatat cgtgggcgcg ggtgctcccc    480
aatggcaccg cgggcactcc caaccgcgag gggctgcgct actaccggcg gctgctggag    540
cggctgcggg agctgggcgt gcagccggtg gttaccctgt accattggga cctgccacag    600
cgcctgcagg acacctatgg cggatgggcc aatcgcgccc tggccgacca tttcagggat    660
tatgccgagc tctgcttccg ccacttcggt ggtcaggtca agtactggat caccattgac    720 aaccccctacg tggtggcctg gcacgggtat gccaccgggc gcctggcccc gggcgtgagg    780
ggcagctcca ggctcgggta cctggttgcc cacaacctac ttttggctca tgccaaagtc    840
tggcatctct acaacacctc tttccgcccc acacagggag gccgggtgtc tatcgcctta    900
agctcccatt ggatcaatcc tcgaagaatg actgactata atatcagaga atgccagaag    960
tctcttgact ttgtgctagg ctggtttgcc aaacccatat ttattgatgg cgactaccca   1020
gagagtatga agaacaacct ctcgtctctt ctgcctgatt ttactgaatc tgagaagagg   1080
ctcatcagag gaactgctga ctttttttgct ctctccttcg gaccaacctt gagctttcag   1140
ctattggacc ctaacatgaa gttccgccaa ttggagtctc ccaacctgag gcagcttctg   1200
tcttggatag atctggaata taaccaccct ccaatattta ttgtggaaaa tggctggttt   1260
gtctcgggaa ccaccaaaag ggatgatgcc aaatatatgt attatctcaa gaagttcata   1320
atggaaacct taaaagcaat cagactggat ggggtcgacg tcattgggta caccgcgtgg   1380
tcgctcatgg acggtttcga gtggcatagg ggctacagca tccggcgagg actcttctac   1440
gttgactttc tgagtcagga caaggagctg ttgccaaagt cttcggcctt gttctaccaa   1500
aagctgatag aggacaatgg cttttcctcct ttacctgaaa accagcccct tgaagggaca   1560
tttccctgtg actttgcttg gggagttgtt gacaactacg ttcaagtaag tcctttgaca   1620
aaacccagtg tcggcctctt gcttcctcac taa                                1653
```

<210> SEQ ID NO 7
<211> LENGTH: 20
<212> TYPE: DNA
<213> ORGANISM: Artificial
<220> FEATURE:
<223> OTHER INFORMATION: forward primer

<400> SEQUENCE: 7
ttcaaacccg gaagtctttg                                                 20

<210> SEQ ID NO 8
<211> LENGTH: 20
<212> TYPE: DNA
<213> ORGANISM: Artificial
<220> FEATURE:
<223> OTHER INFORMATION: Reverse primer

<400> SEQUENCE: 8
ccaggcagac gttcacatta                                                 20

<210> SEQ ID NO 9
<211> LENGTH: 20
<212> TYPE: DNA
<213> ORGANISM: Artificial
<220> FEATURE:
<223> OTHER INFORMATION: Forward primer

```
<400> SEQUENCE: 9
tggctttcct cctttacctg                                              20

<210> SEQ ID NO 10
<211> LENGTH: 18
<212> TYPE: DNA
<213> ORGANISM: Artificial
<220> FEATURE:
<223> OTHER INFORMATION: Reverse primer

<400> SEQUENCE: 10
gccgacactg ggttttgt                                                18

<210> SEQ ID NO 11
<211> LENGTH: 14
<212> TYPE: PRT
<213> ORGANISM: Mus musculus

<400> SEQUENCE: 11

Ser Pro Leu Thr Lys Pro Ser Val Gly Leu Leu Leu Pro His
1               5                   10

<210> SEQ ID NO 12
<211> LENGTH: 5421
<212> TYPE: DNA
<213> ORGANISM: Artificial
<220> FEATURE:
<223> OTHER INFORMATION: Plasmid pGG2
<220> FEATURE:
<221> NAME/KEY: promoter
<222> LOCATION: (206)..(955)
<223> OTHER INFORMATION: CMV IE enhancer/promoter
<220> FEATURE:
<221> NAME/KEY: Intron
<222> LOCATION: (1095)..(1227)
<223> OTHER INFORMATION: Intron from pCl-neo
<220> FEATURE:
<221> NAME/KEY: misc_feature
<222> LOCATION: (1227)..(1334)
<223> OTHER INFORMATION: Multiple Cloning Site (MCS)
<220> FEATURE:
<221> NAME/KEY: polyA_signal
<222> LOCATION: (1369)..(1590)
<223> OTHER INFORMATION: SV40 late poly A signal

<400> SEQUENCE: 12
cagcagctgc gcgctcgctc gctcactgag gccgcccggg caaagcccgg gcgtcgggcg    60
acctttggtc gcccggcctc agtgagcgag cgagcgcgca gagagggagt ggccaactcc   120
atcactaggg gttccttgta gttaatgatt aacccgccat gctacttatc tacgtagcca   180
tgctctagac atggctcgac agatctcaat attggccatt agccatatta ttcattggtt   240
atatagcata aatcaatatt ggctattggc cattgcatac gttgtatcta tcataata    300 tgtacattta tattggctca tgtccaatat gaccgccatg ttggcattga ttattgacta   360
gttattaata gtaatcaatt acggggtcat tagttcatag cccatatatg gagttccgcg   420
ttacataact tacggtaaat ggcccgcctg gctgaccgcc caacgacccc gcccattga    480 cgtcaataat gacgtatgtt cccatagtaa cgccaatagg gactttccat tgacgtcaat   540
gggtggagta tttacggtaa actgcccact tggcagtaca tcaagtgtat catatgccaa   600 gtccgcccc tattgacgtc aatgacggta aatggcccgc ctggcattat gcccagtaca   660
tgaccttacg ggactttcct acttggcagt acatctacgt attagtcatc gctattacca   720
tggtgatgcg gttttggcag tacaccaatg ggcgtggata gcggtttgac tcacggggat   780
```

```
ttccaagtct ccaccccatt gacgtcaatg ggagtttgtt ttggcaccaa aatcaacggg    840
actttccaaa atgtcgtaac aactgcgatc gcccgcccg ttgacgcaaa tgggcggtag     900
gcgtgtacgg tgggaggtct atataagcag agctcgttta gtgaaccgtc agatcactag    960
aagctttatt gcggtagttt atcacagtta aattgctaac gcagtcagtg cttctgacac   1020
aacagtctcg aacttaagct gcagtgactc tcttaaggta gccttgcaga gttggtcgt    1080
gaggcactgg gcaggtaagt atcaaggtta caagacaggt ttaaggagac aatagaaac    1140
tgggcttgtc gagacagaga agactcttgc gtttctgata ggcacctatt ggtcttactg   1200
acatccactt tgccttttctc tccacaggtg tccactccca gttcaattac agctcttaag  1260
gctagagtac ttaatacgac tcactatagg ctagcctcga cctcgagacg cgtgatatcg   1320
gatcccggcc ggcggccgct tccctttagt gagggttaat gcttcgagca gacatgataa   1380
gatacattga tgagtttgga caaaccacaa ctagaatgca gtgaaaaaaa tgctttattt   1440
gtgaaatttg tgatgctatt gctttatttg taaccattat aagctgcaat aaacaagtta   1500
acaacaacaa ttgcattcat tttatgtttc aggttcaggg ggagatgtgg gaggtttttt   1560
aaagcaagta aaacctctac aaatgtggta aaatccgata agggactaga gcatggctac   1620
gtagataagt agcatggcgg gttaatcatt aactacaagg aaccccctagt gatggagttg   1680
gccactccct ctctgcgcgc tcgctcgctc actgaggccg ggcgaccaaa ggtcgcccga   1740
cgcccgggct tgcccgggc ggcctcagtg agcgagcgag cgcgccagct ggcgtaatag   1800
cgaagaggcc cgcaccgatc gcccttccca acagttgcgc agcctgaatg gcgaatggaa   1860
ttccagacga ttgagcgtca aaatgtaggt atttccatga gcgttttttcc gttgcaatgg   1920
ctggcggtaa tattgttctg gatattacca gcaaggccga tagtttgagt tcttctactc   1980
aggcaagtga tgttattact aatcaaagaa gtattgcgac aacggttaat ttgcgtgatg   2040
gacagactct tttactcggt ggcctcactg attataaaaa cacttctcag gattctggcg   2100
taccgttcct gtctaaaatc cctttaatcg gcctcctgtt tagctcccgc tctgattcta   2160
acgaggaaag cacgttatac gtgctcgtca aagcaaccat agtacgcgcc ctgtagcggc   2220
gcattaagcg cggcgggtgt ggtggttacg cgcagcgtga ccgctacact tgccagcgcc   2280
ctagcgcccg ctcctttcgc tttcttccct tcctttctcg ccacgttcgc cggctttccc   2340
cgtcaagctc taaatcgggg gctccctta gggttccgat ttagtgcttt acggcacctc   2400
gaccccaaaa aacttgatta gggtgatggt tcacgtagtg ggccatcgcc ctgatagacg   2460
gttttttcgcc ctttgacgtt ggagtccacg ttctttaata gtggactctt gttccaaact   2520
ggaacaacac tcaaccctat ctcggtctat tcttttgatt tataagggat tttgccgatt   2580
tcggcctatt ggttaaaaaa tgagctgatt taacaaaaat ttaacgcgaa ttttaacaaa   2640
atattaacgt ctacaattta aatatttgct tatacaatct tcctgttttt ggggcttttc   2700
tgattatcaa ccgggtaca tatgattgac atgctagttt tacgattacc gttcatcgat   2760
tctcttgttt gctccagact ctcaggcaat gacctgatag cctttgtaga gacctctcaa   2820
aaatagctac cctctccggc atgaatttat cagctagaac ggttgaatat catattgatg   2880
gtgatttgac tgtctccggc ctttctcacc cgtttgaatc tttacctaca cattactcag   2940
gcattgcatt taaaatatat gagggttcta aaaattttta tccttgcgtt gaaataaagg   3000
cttctcccgc aaaagtatta cagggtcata atgtttttgg tacaaccgat ttagctttat   3060
gctctgaggc tttattgctt aattttgcta attctttgcc ttgcctgtat gatttattgg   3120
atgttggaat cgcctgatgc ggtattttct ccttacgcat ctgtgcggta tttcacaccg   3180
```

```
catatggtgc actctcagta caatctgctc tgatgccgca tagttaagcc agccccgaca    3240
cccgccaaca cccgctgacg cgccctgacg ggcttgtctg ctcccggcat ccgcttacag    3300
acaagctgtg accgtctccg ggagctgcat gtgtcagagg ttttcaccgt catcaccgaa    3360
acgcgcgaga cgaaagggcc tcgtgatacg cctatttta taggttaatg tcatgataat    3420
aatggtttct tagacgtcag gtggcacttt tcggggaaat gtgcgcggaa cccctatttg    3480
tttattttc taaatacatt caaatatgta tccgctcatg acaataac cctgataaat    3540
gcttcaataa tattgaaaaa ggaagagtat gagtattcaa catttccgtg tcgcccttat    3600
tccctttttt gcggcatttt gccttcctgt ttttgctcac ccagaaacgc tggtgaaagt    3660
aaaagatgct gaagatcagt tgggtgcacg agtgggttac atcgaactgg atctcaacag    3720
cggtaagatc cttgagagtt ttcgccccga agaacgtttt ccaatgatga gcacttttaa    3780
agttctgcta tgtggcgcgg tattatcccg tattgacgcc gggcaagagc aactcggtcg    3840
ccgcatacac tattctcaga atgacttggt tgagtactca ccagtcacag aaaagcatct    3900
tacggatggc atgacagtaa gagaattatg cagtgctgcc ataaccatga gtgataacac    3960
tgcggccaac ttacttctga caacgatcgg aggaccgaag gagctaaccg cttttttgca    4020
caacatgggg gatcatgtaa ctcgccttga tcgttgggaa ccggagctga atgaagccat    4080
accaaacgac gagcgtgaca ccacgatgcc tgtagcaatg gcaacaacgt tgcgcaaact    4140
attaactggc gaactactta ctctagcttc ccggcaacaa ttaatagact ggatggaggc    4200
ggataaagtt gcaggaccac ttctgcgctc ggcccttccg gctggctggt ttattgctga    4260
taaatctgga gccggtgagc gtgggtctcg cggtatcatt gcagcactgg ggccagatgg    4320
taagccctcc cgtatcgtag ttatctacac gacgggagt caggcaacta tggatgaacg    4380
aaatagacag atcgctgaga taggtgcctc actgattaag cattggtaac tgtcagacca    4440
agtttactca tatatacttt agattgattt aaaacttcat ttttaattta aaaggatcta    4500
ggtgaagatc cttttttgata atctcatgac caaaatccct taacgtgagt tttcgttcca    4560
ctgagcgtca gaccccgtag aaaagatcaa aggatcttct tgagatcctt ttttttctgcg    4620
cgtaatctgc tgcttgcaaa caaaaaaacc accgctacca gcggtggttt gtttgccgga    4680
tcaagagcta ccaactcttt ttccgaaggt aactggcttc agcagagcgc agataccaaa    4740
tactgtcctt ctagtgtagc cgtagttagg ccaccacttc aagaactctg tagcaccgcc    4800
tacataccctc gctctgctaa tcctgttacc agtggctgct gccagtggcg ataagtcgtg    4860
tcttaccggg ttggactcaa gacgatagtt accggataag gcgcagcggt cgggctgaac    4920
ggggggttcg tgcacacagc ccagcttgga gcgaacgacc tacaccgaac tgagatacct    4980
acagcgtgag ctatgagaaa gcgccacgct tcccgaaggg agaaaggcgg acaggtatcc    5040
ggtaagcggc agggtcggaa caggagagcg cacgagggag cttccagggg gaaacgcctg    5100
gtatctttat agtcctgtcg ggtttcgcca cctctgactt gagcgtcgat ttttgtgatg    5160
ctcgtcaggg gggcggagcc tatggaaaaa cgccagcaac gcggcctttt tacggttcct    5220
ggccttttgc tggccttttg ctcacatgtt ctttcctgcg ttatcccctg attctgtgga    5280
taaccgtatt accgcctttg agtgagctga taccgctcgc cgcagccgaa cgaccgagcg    5340
cagcgagtca gtgagcgagg aagcggaaga gcgcccaata cgcaaaccgc ctctccccgc    5400
gcgttggccg attcattaat g                                              5421

<210> SEQ ID NO 13
```

<211> LENGTH: 8335
<212> TYPE: DNA
<213> ORGANISM: Artificial
<220> FEATURE:
<223> OTHER INFORMATION: pGG2 plasmid comprising sequences of CMV IE
      promoter and the sequence coding for mouse m-KL (pGG2-m-KL)

<400> SEQUENCE: 13

```
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca     180
tgctctagac atggctcgac agatctcaat attggccatt agccatatta ttcattggtt     240
atatagcata aatcaatatt ggctattggc cattgcatac gttgtatcta tatcataata     300
tgtacattta tattggctca tgtccaatat gaccgccatg ttggcattga ttattgacta     360
gttattaata gtaatcaatt acggggtcat tagttcatag cccatatatg gagttccgcg     420
ttacataact tacggtaaat ggcccgcctg gctgaccgcc caacgacccc cgcccattga     480
cgtcaataat gacgtatgtt cccatagtaa cgccaatagg actttccat tgacgtcaat     540 gggtggagta tttacggtaa actgcccact tggcagtaca tcaagtgtat catatgccaa     600
gtccgccccc tattgacgtc aatgacggta atggcccgc ctggcattat gcccagtaca     660
tgaccttacg ggactttcct acttggcagt acatctacgt attagtcatc gctattacca     720
tggtgatgcg gttttggcag tacaccaatg ggcgtggata gcggtttgac tcacggggat     780
ttccaagtct ccaccccatt gacgtcaatg ggagtttgtt ttggcaccaa aatcaacggg     840
actttccaaa atgtcgtaac aactgcgatc gcccgccccg ttgacgcaaa tgggcggtag     900
gcgtgtacgg tgggaggtct atataagcag agctcgttta gtgaaccgtc agatcactag     960
aagcttgata tcgaattcgc ccttgataat cattgctcgt ggggcggcgg gagcggggt    1020 gggcaccgcg tagggagggc ggcggggcgc gggcatatag gggcgcggcg cggtgccctc    1080
ccggctcccg cagcatgcta gcccgcgccc ctcctcgccg cccgccgcgg ctggtgctgc    1140
tccgtttgct gttgctgcat ctgctgctgc tcgccctgcg cgcccgctgc ctgagcgctg    1200
agccgggtca gggcgcgcag acctgggctc gcttcgcgcg cgctcctgcc ccagaggccg    1260
ctggcctcct ccacgacacc ttccccgacg gtttcctctg gcggtaggc agcgccgcct    1320 atcagaccga gggcggctgg cgacagcacg gcaaaggcgc gtccatctgg gacactttca    1380
cccatcactc tggggcggcc ccgtccgact ccccgatcgt cgtggcgccg tcgggtgccc    1440
cgtcgcctcc cctgtcctcc actggagatg tggccagcga tagttacaac aacgtctacc    1500
gcgacacaga ggggctgcgc gaactggggg tcacccacta ccgcttctcc atatcgtggg    1560
cgcgggtgct cccaatggc accgcgggca ctcccaaccg cgaggggctg cgctactacc    1620
ggcggctgct ggagcggctg cgggagctgg gcgtgcagcc ggtggttacc ctgtaccatt    1680
gggacctgcc acagcgcctg caggacacct atggcggatg gccaatcgc gccctggccg    1740 accatttcag ggattatgcc gagctctgct ccgccactt cggtggtcag gtcaagtact    1800
ggatcaccat tgacaacccc tacgtggtgg cctggcacgg gtatgccacc gggcgcctgg    1860
ccccgggcgt gaggggcagc tccaggctcg ggtacctggt gcccacaac ctactttgg    1920 ctcatgccaa agtctggcat ctctacaaca cctctttccg ccccacacag ggaggccggg    1980
tgtctatcgc cttaagctcc cattggatca atcctcgaag aatgactgac tataatatca    2040
gagaatgcca gaagtctctt gactttgtgc taggctggtt tgccaaaccc atatttattg    2100
```

```
atggcgacta cccagagagt atgaagaaca acctctcgtc tcttctgcct gattttactg    2160
aatctgagaa gaggctcatc agaggaactg ctgactttt tgctctctcc ttcggaccaa     2220
ccttgagctt tcagctattg gaccctaaca tgaagttccg ccaattggag tctcccaacc    2280
tgaggcagct tctgtcttgg atagatctgg aatataacca ccctccaata tttattgtgg    2340
aaaatggctg gtttgtctcg ggaaccacca aaagggatga tgccaaatat atgtattatc    2400
tcaagaagtt cataatggaa accttaaaag caatcagact ggatgggggtc gacgtcattg   2460
ggtacaccgc gtggtcgctc atggacggtt tcgagtggca taggggctac agcatccggc   2520
gaggactctt ctacgttgac tttctgagtc aggacaagga gctgttgcca aagtcttcgg   2580
ccttgttcta ccaaaagctg atagaggaca atggctttcc tcctttacct gaaaaccagc   2640
cccttgaagg gacatttccc tgtgactttg cttggggagt tgttgacaac tacgttcaag   2700
tggacactac tctctctcag tttactgacc cgaatgtcta tctgtgggat gtgcatcaca   2760
gtaagaggct tattaaagta gacgggggttg tagccaagaa gagaaaacct tactgtgttg   2820
atttctctgc catccggcct cagataacct tacttcgaga aatgcgggtc acccactttc    2880
gcttctccct ggactgggcc ctgatcttgc ctctgggtaa ccagacccaa gtgaaccaca   2940
cggttctgca cttctaccgc tgcatgatca gcgagctggt gcacgccaac atcactccag   3000
tggtggccct gtggcagcca gcagccccgc accaaggcct gccacatgcc cttgcaaaac   3060
atgggggcctg ggagaacccg cacactgctc tggcgtttgc agactacgca aacctgtgtt   3120
ttaaagagtt gggtcactgg gtcaatctct ggatcaccat gaacgagcca acacacgga    3180
acatgaccta tcgtgccggg caccacctcc tgagagccca tgccttggct tggcatctgt   3240
acgatgacaa gtttagggcg gctcagaaag gcaaaatatc catcgccttg caggctgact   3300
ggatagaacc ggcctgccct ttctctcaaa atgacaaaga agtggccgag agagttttgg   3360
aatttgatat aggctggctg gcagagccta ttttggttc cggagattat ccacgtgtga    3420
tgaggggactg gctgaaccaa aaaaacaatt ttcttttgcc ctatttcacc gaagatgaaa   3480
aaaagctagt ccgggggttcc tttgacttcc tggcggtgag tcattacacc accattctgg   3540
tagactggga aaaggaggat ccgatgaaat acaacgatta cttggaggta caggagatga   3600
ctgacatcac atggctcaac tctcccagtc aggtggcagt ggtgccttgg gggctgcgca   3660
aagtgctcaa ctggctaagg ttcaagtacg gagacctccc gatgtatgtg acagccaatg   3720
gaatcgatga tgaccccccac gccgagcaag actcactgag gatctattat attaagaatt   3780
atgtgaatga ggctctgaaa gcctacgtgt tggacgacat caacctttgt ggctactttg   3840
cgtattcact tagtgatcgc tcagctccca gtctggcctt ttatcgatat gctgcgaatc   3900
agtttgagcc caaaccatct atgaaacatt acaggaaaat tattgacagc aatggcttcc   3960
tggggttctgg aacactggga aggttttgtc cagaagaata cactgtgtgc accgaatgtg   4020
gatttttca aaccccggaag tctttgctgg tcttcatctc gtttcttgtt tttactttta   4080
ttatttctct tgctctcatt tttcactact ccaagaaagg ccagagaagt tataagtaat    4140
gtgaacgtct gcctggccat tcgctttggg atcaagatgt acacgccgtc agccgtttgc    4200
acctctctgt gttgtgagcc gcattccaca catttcgatt ctagagcggc cgcttccctt    4260
tagtgagggt taatgcttcg agcagacatg ataagataca ttgatgagtt tggacaaacc    4320
acaactagaa tgcagtgaaa aaatgcttt atttgtgaaa tttgtgatgc tattgcttta    4380
tttgtaacca tttaagcctg caataaacaa gttaacaaca caattgcat tcattttatg     4440
tttcaggttc agggggggagat gtgggaggtt ttttaaagca agtaaaaacct ctacaaatgt   4500
```

```
ggtaaaatcc gataagggac tagagcatgg ctacgtagat aagtagcatg gcgggttaat    4560
cattaactac aaggaacccc tagtgatgga gttggccact ccctctctgc gcgctcgctc    4620
gctcactgag gccgggcgac caaaggtcgc ccgacgcccg ggctttgccc gggcggcctc    4680
agtgagcgag cgagcgcgcc agctggcgta atagcgaaga ggcccgcacc gatcgccctt    4740
cccaacagtt gcgcagcctg aatggcgaat ggaattccag acgattgagc gtcaaaatgt    4800
aggtatttcc atgagcgttt ttccgttgca atggctggcg gtaatattgt tctggatatt    4860
accagcaagg ccgatagttt gagttcttct actcaggcaa gtgatgttat tactaatcaa    4920
agaagtattg cgacaacggt taatttgcgt gatggacaga ctcttttact cggtggcctc    4980
actgattata aaacacttc tcaggattct ggcgtaccgt tcctgtctaa atccctttta    5040
atcggcctcc tgtttagctc ccgctctgat tctaacgagg aaagcacgtt atacgtgctc    5100
gtcaaagcaa ccatagtacg cgccctgtag cggcgcatta agcgcggcgg gtgtggtggt    5160
tacgcgcagc gtgaccgcta cacttgccag cgccctagcg cccgctcctt tcgctttctt    5220
cccttccttt ctcgccacgt tcgccggctt tccccgtcaa gctctaaatc ggggggctccc    5280 tttagggttc cgatttagtg ctttacggca cctcgacccc aaaaaacttg attagggtga    5340
tggttcacgt agtgggccat cgccctgata gacggttttt cgccctttga cgttggagtc    5400
cacgttcttt aatagtggac tcttgttcca aactggaaca acactcaacc ctatctcggt    5460
ctattctttt gatttataag ggattttgcc gatttcggcc tattggttaa aaaatgagct    5520
gatttaacaa aaatttaacg cgaattttaa caaaatatta acgtctacaa tttaaatatt    5580
tgcttataca atcttcctgt ttttggggct tttctgatta tcaaccgggg tacatatgat    5640
tgacatgcta gttttacgat taccgttcat cgattctctt gtttgctcca gactctcagg    5700
caatgacctg atagcctttg tagagacctc tcaaaaatag ctaccctctc cggcatgaat    5760
ttatcagcta gaacggttga atatcatatt gatggtgatt tgactgtctc cggcctttct    5820
cacccgtttg aatctttacc tacacattac tcaggcattg catttaaaat atgtgagggt    5880
tctaaaaatt tttatccttg cgttgaaata aaggcttctc ccgcaaaagt attacagggt    5940
cataatgttt ttggtacaac cgatttagct ttatgctctg aggctttatt gcttaatttt    6000
gctaattctt tgccttgcct gtatgattta ttggatgttg gaatcgcctg atgcggtatt    6060
ttctccttac gcatctgtgc ggtatttcac accgcatatg gtgcactctc agtacaatct    6120
gctctgatgc cgcatagtta agccagcccc gacacccgcc aacacccgct gacgcgccct    6180
gacgggcttg tctgctcccg gcatccgctt acagacaagc tgtgaccgtc tccgggagct    6240
gcatgtgtca gaggttttca ccgtcatcac cgaaacgcgc gagacgaaag gcctcgtga    6300 tacgcctatt tttataggtt aatgtcatga taataatggt ttcttagacg tcaggtggca    6360
cttttcgggg aaatgtgcgc ggaaccccta tttgtttatt tttctaaata cattcaaata    6420
tgtatccgct catgagacaa taaccctgat aaatgcttca ataatattga aaaggaaga    6480 gtatgagtat tcaacatttc cgtgtcgccc ttattccctt ttttgcggca ttttgccttc    6540 ctgttttgc tcacccagaa acgctggtga agtaaaaga tgctgaagat cagttgggtg    6600
cacgagtggg ttacatcgaa ctggatctca acagcggtaa gatccttgag agttttcgcc    6660
ccgaagaacg ttttccaatg atgagcactt taaagttct gctatgtggc gcggtattat    6720
cccgtattga cgccgggcaa gagcaactcg gtcgccgcat acactattct cagaatgact    6780
tggttgagta ctcaccagtc acagaaaagc atcttacgga tggcatgaca gtaagagaat    6840
```

| | |
|---|---:|
| tatgcagtgc tgccataacc atgagtgata acactgcggc caacttactt ctgacaacga | 6900 |
| tcggaggacc gaaggagcta accgcttttt tgcacaacat gggggatcat gtaactcgcc | 6960 |
| ttgatcgttg ggaaccggag ctgaatgaag ccataccaaa cgacgagcgt gacaccacga | 7020 |
| tgcctgtagc aatggcaaca acgttgcgca aactattaac tggcgaacta cttactctag | 7080 |
| cttcccggca acaattaata gactggatgg aggcggataa agttgcagga ccacttctgc | 7140 |
| gctcggccct ccggctggc tggtttattg ctgataaatc tggagccggt gagcgtgggt | 7200 |
| ctcgcggtat cattgcagca ctggggccag atggtaagcc ctcccgtatc gtagttatct | 7260 |
| acacgacggg gagtcaggca actatggatg aacgaaatag acagatcgct gagataggtg | 7320 |
| cctcactgat taagcattgg taactgtcag accaagttta ctcatatata ctttagattg | 7380 |
| atttaaaact tcatttttaa tttaaaagga tctaggtgaa gatcctttt gataatctca | 7440 |
| tgaccaaaat cccttaacgt gagttttcgt tccactgagc gtcagacccc gtagaaaaga | 7500 |
| tcaaaggatc ttcttgagat cctttttttc tgcgcgtaat ctgctgcttg caaacaaaaa | 7560 |
| aaccaccgct accagcggtg gtttgtttgc cggatcaaga gctaccaact cttttccga | 7620 |
| aggtaactgg cttcagcaga gcgcagatac caaatactgt ccttctagtg tagccgtagt | 7680 |
| taggccacca cttcaagaac tctgtagcac cgcctacata cctcgctctg ctaatcctgt | 7740 |
| taccagtggc tgctgccagt ggcgataagt cgtgtcttac cgggttggac tcaagacgat | 7800 |
| agttaccgga taaggcgcag cggtcgggct gaacggggg ttcgtgcaca cagcccagct | 7860 |
| tggagcgaac gacctacacc gaactgagat acctacagcg tgagctatga aaagcgcca | 7920 |
| cgcttcccga agggagaaag gcggacaggt atccggtaag cggcagggtc ggaacaggag | 7980 |
| agcgcacgag ggagcttcca gggggaaacg cctggtatct ttatagtcct gtcgggtttc | 8040 |
| gccacctctg acttgagcgt cgatttttgt gatgctcgtc aggggggcgg agcctatgga | 8100 |
| aaaacgccag caacgcggcc ttttacggt tcctggcctt tgctggcct tttgctcaca | 8160 |
| tgttctttcc tgcgttatcc cctgattctg tggataaccg tattaccgcc tttgagtgag | 8220 |
| ctgataccgc tcgccgcagc cgaacgaccg agcgcagcga gtcagtgagc gaggaagcgg | 8280 |
| aagagcgccc aatacgcaaa ccgcctctcc ccgcgcgttg gccgattcat taatg | 8335 |

<210> SEQ ID NO 14
<211> LENGTH: 5640
<212> TYPE: DNA
<213> ORGANISM: Artificial
<220> FEATURE:
<223> OTHER INFORMATION: synthetic plasmid pUC57-KL (GenScript, USA)

<400> SEQUENCE: 14

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aaggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cttctagaat gctcgcccgc | 420 |
| gccctcctc gccgcccgcc gcggctggtg ctgctccgtt tgctgttgct gcatctgctg | 480 |
| ctgctcgccc tgcgcgcccg ctgcctgagc gctgagccgg tcagggcgc gcagacctgg | 540 |
| gctcgcttcg cgcgcgctcc tgccccagag gccgctggcc tcctccacga caccttcccc | 600 |

-continued

```
gacggtttcc tctgggcggt aggcagcgcc gcctatcaga ccgagggcgg ctggcgacag    660
cacggcaaag gcgcgtccat ctgggacact ttcacccatc actctggggc ggccccgtcc    720
gactccccga tcgtcgtggc gccgtcgggt gccccgtcgc ctccctgtc ctccactgga     780 gatgtggcca gcgatagtta caacaacgtc taccgcgaca cagaggggct gcgcgaactg    840
ggggtcaccc actaccgctt ctccatatcg tgggcgcggg tgctccccaa tggcaccgcg    900
ggcactccca accgcgaggg gctgcgctac taccggcggc tgctggagcg gctgcgggag    960
ctgggcgtgc agccggtggt taccctgtac cattgggacc tgccacagcg cctgcaggac    1020
acctatggcg gatgggccaa tcgcgccctg gccgaccatt tcaggattat tgccgagctc    1080
tgcttccgcc acttcggtgg tcaggtcaag tactggatca ccattgacaa cccctacgtg    1140
gtggcctgga cgggtatgc caccgggcgc ctggccccgg gcgtgagggg cagctccagg     1200
ctcgggtacc tggttgccca aacctactt ttggctcatg ccaaagtctg gcatctctac      1260
aacacctctt tccgccccac acagggaggc cgggtgtcta tcgccttaag ctcccattgg    1320
atcaatcctc gaagaatgac tgactataat atcagagaat gccagaagtc tcttgacttt    1380
gtgctaggct ggtttgccaa acccatattt attgatggcg actacccaga gagtatgaag    1440
aacaacctct cgtctcttct gcctgatttt actgaatctg agaagaggct catcagagga    1500
actgctgact ttttgctct ctccttcgga ccaaccttga gctttcagct attggaccct      1560
aacatgaagt tccgccaatt ggagtctccc aacctgaggc agcttctgtc ttggatagat    1620
ctggaatata accaccctcc aatatttatt gtggaaaatg gctggtttgt tcgggaacc     1680 accaaaaggg atgatgccaa atatatgtat tatctcaaga agttcataat ggaaacctta    1740
aaagcaatca gactggatgg ggtcgacgtc attgggtaca ccgcgtggtc gctcatggac    1800
ggtttcgagt ggcatagggg ctacagcatc cggcgaggac tcttctacgt tgactttctg    1860
agtcaggaca aggagctgtt gccaaagtct tcggccttgt tctaccaaaa gctgatagag    1920
gacaatggct ttcctccttt acctgaaaac cagccccttg aagggacatt tccctgtgac    1980
tttgcttggg gagttgttga caactacgtt cagctgagtc tttgacaaa acccagtgtc      2040 ggcctcttgc ttcctcacta agggcccaga gactgaagct ttacgtagac actactctct    2100
ctcagtttac tgacccgaat gtctatctgt gggatgtgca tcacagtaag aggcttatta    2160
aagtagacgg ggttgtagcc aaggctagca aaccttactg tgttgatttc tctgccatcc    2220
ggcctcagat aaccttactt cgagaaatgc gggtcaccca ctttcgcttc tccctggact    2280
gggcgctgat cttgcctctg gtaaccagac cccaagtgaa ccacacggtt ctgcacttct    2340
accgctgcat gatcagcgag ctggtgcacg ccaacatcac tccagtggtg gccctgtggc    2400
agccagcagc cccgcaccaa ggcctgccac atgcccttgc aaaacatggg gcctgggaga    2460
acccgcacac tgctctggcg tttgcagact acgcaaacct gtgttttaaa gagttgggtc    2520
actgggtcaa tctctggatc accatgaacg agccaaacac acggaacatg acctatcgtg    2580
ccgggcacca cctcctgaga gcccatgcct tggcttggca tctgtacgat gacaagttta    2640
gggcggctca gaaaggcaaa atatccatcg ccttgcaggc tgactggata gaaccggcct    2700 gcccttttctc tcaaaatgac aaagaagtgg ccgagagagt tttggaattt gatataggct    2760
ggctggcaga gcctattttt ggttccggag attatccacg tgtgatgagg gactggctga    2820
accaaaaaaa caatttttctt ttgccctatt tcaccgaaga tgaaaaaaag ctagtccggg    2880
gttcctttga cttcctggcg gtgagtcatt acaccaccat tctggtagac tgggaaaagg    2940
```

-continued

```
aggatccgat gaaatacaac gattacttgg aggtacagga gatgactgac atcacatggc    3000
tcaactctcc cagtcaggtg gcagtggtgc cttgggggct gcgcaaagtg ctcaactggc    3060
taaggttcaa gtacggagac ctcccgatgt atgtgacagc caatggaatc gatgatgacc    3120
cccacgccga gcaagactca ctgaggatct attatattaa gaattatgtg aatgaggctc    3180
tgaaagccta cgtgttggac gacatcaacc tttgtggcta ctttgcgtat tcacttagtg    3240
atcgctcagc tcccaagtct ggcttttatc gatatgctgc gaatcagttt gagcccaaac    3300
catctatgaa acattacagg aaaattattg acagcaatgg cttcctgggt tctggaacac    3360
tgggaaggtt ttgtccagaa gaataagcgg ccgcgcatgc aagcttggcg taatcatggt    3420
catagctgtt tcctgtgtga aattgttatc cgctcacaat tccacacaac atacgagccg    3480
gaagcataaa gtgtaaagcc tggggtgcct aatgagtgag ctaactcaca ttaattgcgt    3540
tgcgctcact gcccgctttc cagtcgggaa acctgtcgtg ccagctgcat taatgaatcg    3600
gccaacgcgc ggggagaggc ggtttgcgta ttgggcgctc ttccgcttcc tcgctcactg    3660
actcgctgcg ctcggtcgtt cggctgcggc gagcggtatc agctcactca aaggcggtaa    3720
tacggttatc cacagaatca ggggataacg caggaaagaa catgtgagca aaaggccagc    3780
aaaaggccag gaaccgtaaa aaggccgcgt tgctggcgtt tttccatagg ctccgccccc    3840
ctgacgagca tcacaaaaat cgacgctcaa gtcagaggtg gcgaaacccg acaggactat    3900
aaagatacca ggcgtttccc cctggaagct ccctcgtgcg ctctcctgtt ccgaccctgc    3960
cgcttaccgg atacctgtcc gcctttctcc cttcgggaag cgtggcgctt tctcatagct    4020
cacgctgtag gtatctcagt tcggtgtagg tcgttcgctc caagctgggc tgtgtgcacg    4080
aaccccccgt tcagcccgac cgctgcgcct tatccggtaa ctatcgtctt gagtccaacc    4140
cggtaagaca cgacttatcg ccactggcag cagccactgg taacaggatt agcagagcga    4200
ggtatgtagg cggtgctaca gagttcttga agtggtggcc taactacggc tacactagaa    4260
gaacagtatt tggtatctgc gctctgctga agccagttac cttcggaaaa agagttggta    4320
gctcttgatc cggcaaacaa accaccgctg gtagcggtgg ttttttttgtt tgcaagcagc    4380 agattacgcg cagaaaaaaa ggatctcaag aagatccttt gatcttttct acggggtctg    4440
acgctcagtg gaacgaaaac tcacgttaag ggattttggt catgagatta tcaaaaagga    4500
tcttcaccta gatcctttta aattaaaaat gaagttttaa atcaatctaa agtatatatg    4560
agtaaacttg gtctgacagt taccaatgct taatcagtga ggcacctatc tcagcgatct    4620
gtctatttcg ttcatccata gttgcctgac tccccgtcgt gtagataact acgatacggg    4680
agggcttacc atctggcccc agtgctgcaa tgataccgcg agacccacgc tcaccggctc    4740
cagatttatc agcaataaac cagccagccg gaagggccga gcgcagaagt ggtcctgcaa    4800
ctttatccgc ctccatccag tctattaatt gttgccggga agctagagta agtagttcgc    4860
cagttaatag tttgcgcaac gttgttgcca ttgctacagg catcgtggtg tcacgctcgt    4920
cgtttggtat ggcttcattc agctccggtt cccaacgatc aaggcgagtt acatgatccc    4980
ccatgttgtg caaaaaagcg gttagctcct tcggtcctcc gatcgttgtc agaagtaagt    5040
tggccgcagt gttatcactc atggttatgg cagcactgca taattctctt actgtcatgc    5100
catccgtaag atgcttttct gtgactggtg agtactcaac caagtcattc tgagaatagt    5160
gtatgcggcg accgagttgc tcttgcccgg cgtcaatacg ggataatacc gcgccacata    5220
gcagaacttt aaaagtgctc atcattggaa aacgttcttc ggggcgaaaa ctctcaagga    5280
tcttaccgct gttgagatcc agttcgatgt aacccactcg tgcacccaac tgatcttcag    5340
```

```
catcttttac tttcaccagc gtttctgggt gagcaaaaac aggaaggcaa aatgccgcaa    5400
aaaagggaat aagggcgaca cggaaatgtt gaatactcat actcttcctt tttcaatatt    5460
attgaagcat ttatcagggt tattgtctca tgagcggata catatttgaa tgtatttaga    5520
aaaataaaca aataggggtt ccgcgcacat ttccccgaaa agtgccacct gacgtctaag    5580
aaaccattat tatcatgaca ttaacctata aaaataggcg tatcacgagg ccctttcgtc    5640
```

<210> SEQ ID NO 15
<211> LENGTH: 5931
<212> TYPE: DNA
<213> ORGANISM: Artificial
<220> FEATURE:
<223> OTHER INFORMATION: pGG2 plasmid comprising sequences of CMV IE
      promoter and the sequence coding for mouse s-KL (pGG2-s-KL)

<400> SEQUENCE: 15

```
cagcagctgc gcgctcgctc gctcactgag gccgcccggg caaagcccgg gcgtcgggcg      60
acctttggtc gcccggcctc agtgagcgag cgagcgcgca gagggagt ggccaactcc      120 atcactaggg gttccttgta gttaatgatt aacccgccat gctacttatc tacgtagcca     180
tgctctagaa tgctcgcccg cgcccctcct cgccgcccgc cgcggctggt gctgctccgt     240
ttgctgttgc tgcatctgct gctgctcgcc ctgcgcgccc gctgcctgag cgctgagccg     300
ggtcagggcg cgcagacctg ggctcgcttc gcgcgcgctc ctgccccaga ggccgctggc     360
ctcctccacg acaccttccc cgacggtttc tctgggcgg taggcagcgc cgcctatcag     420
accgagggcg gctggcgaca gcacggcaaa ggcgcgtcca tctgggacac tttcacccat     480
cactctgggg cggccccgtc cgactccccg atcgtcgtgg cgccgtcggg tgccccgtcg     540
cctcccctgt cctccactgg agatgtggcc agcgatagtt acaacaacgt ctaccgcgac     600
acagaggggc tgcgcgaact gggggtcacc cactaccgct tctccatatc gtgggcgcgg     660
gtgctcccca tggcaccgc gggcactccc aaccgcgagg ggctgcgcta ctaccggcgg     720
ctgctggagc ggctgcggga gctgggcgtg cagccggtgg ttaccctgta ccattgggac     780
ctgccacagc gcctgcagga cacctatggc ggatgggcca atcgcgccct ggccgaccat     840
ttcagggatt atgccgagct ctgcttccgc cacttcggtg gtcaggtcaa gtactggatc     900
accattgaca cccctacgt ggtggcctgg cacgggtatg ccaccggcg cctggccccg     960 ggcgtgaggg gcagctccag gctcgggtac ctggttgccc acaacctact tttggctcat    1020
gccaaagtct ggcatctcta caacacctct tccgccccca cagggagg ccgggtgtct    1080 atcgccttaa gctcccattg gatcaatcct cgaagaatga ctgactataa tatcagagaa    1140
tgccagaagt ctcttgactt tgtgctaggc tggtttgcca aacccatatt tattgatggc    1200
gactacccag agagtatgaa gaacaacctc tcgtctcttc tgcctgattt tactgaatct    1260
gagaagaggc tcatcagagg aactgctgac ttttttgctc tctccttcgg accaaccttg    1320
agctttcagc tattggaccc taacatgaag ttccgccaat ggagtctcc caacctgagg    1380 cagcttctgt cttggataga tctggaatat aaccaccctc caatatttat tgtggaaaat    1440
ggctggtttg tctcgggaac caccaaaagg gatgatgcca aatatatgta ttatctcaag    1500
aagttcataa tggaaaacctt aaaagcaatc agactggatg gggtcgacgt cattgggtac    1560
accgcgtggt cgctcatgga cggtttcgag tggcataggg ctacagcat ccggcgagga    1620 ctcttctacg ttgactttct gagtcaggac aaggagctgt tgccaaagtc ttcggccttg    1680
ttctaccaaa agctgataga ggacaatggc tttcctcctt tacctgaaaa ccagcccctt    1740
```

```
gaagggacat tcccctgtga ctttgcttgg ggagttgttg acaactacgt tcagctgagt    1800
cctttgacaa aacccagtgt cggcctcttg cttcctcact aagggccgct tcccctttagt   1860 gagggttaat gcttcgagca gacatgataa gatacattga tgagtttgga caaaccacaa    1920
ctagaatgca gtgaaaaaaa tgctttattt gtgaaatttg tgatgctatt gctttatttg    1980
taaccattat aagctgcaat aaacaagtta acaacaacaa ttgcattcat tttatgtttc    2040
aggttcaggg ggagatgtgg gaggtttttt aaagcaagta aaacctctac aaatgtggta    2100
aaatccgata agggactaga gcatggctac gtagataagt agcatggcgg gttaatcatt    2160
aactacaagg aaccccctagt gatggagttg gccactccct ctctgcgcgc tcgctcgctc    2220
actgaggccg ggcgaccaaa ggtcgcccga cgcccgggct ttgcccgggc ggcctcagtg    2280
agcgagcgag cgcgccagct ggcgtaatag cgaagaggcc cgcaccgatc gcccttccca    2340
acagttgcgc agcctgaatg gcgaatggaa ttccagacga ttgagcgtca aaatgtaggt    2400
atttccatga gcgttttttcc gttgcaatgg ctggcggtaa tattgttctg gatattacca    2460
gcaaggccga tagtttgagt tcttctactc aggcaagtga tgttattact aatcaaagaa    2520
gtattgcgac aacggttaat ttgcgtgatg gacagactct tttactcggt ggcctcactg    2580
attataaaaa cacttctcag gattctggcg taccgttcct gtctaaaatc cctttaatcg    2640
gcctcctgtt tagctcccgc tctgattcta acgaggaaag cacgttatac gtgctcgtca    2700
aagcaaccat agtacgcgcc ctgtagcggc gcattaagcg cggcgggtgt ggtggttacg    2760
cgcagcgtga ccgctacact tgccagcgcc ctagcgcccg ctcctttcgc tttcttccct    2820
tcctttctcg ccacgttcgc cggctttccc cgtcaagctc taaatcgggg gctcccttta    2880
gggttccgat ttagtgcttt acggcacctc gaccccaaaa aacttgatta gggtgatggt    2940
tcacgtagtg ggccatcgcc ctgatagacg gttttttcgcc ctttgacgtt ggagtccacg    3000
ttctttaata gtggactctt gttccaaact ggaacaacac tcaaccctat ctcggtctat    3060
tcttttgatt tataagggat tttgccgatt tcggcctatt ggttaaaaaa tgagctgatt    3120
taacaaaaat ttaacgcgaa ttttaacaaa atattaacgt ctacaattta aatatttgct    3180
tatacaatct tcctgttttt ggggcttttc tgattatcaa ccggggtaca tatgattgac    3240
atgctagttt tacgattacc gttcatcgat tctcttgttt gctccagact ctcaggcaat    3300
gacctgatag ccttttgtaga gacctctcaa aaatagctac cctctccggc atgaatttat    3360
cagctagaac ggttgaatat catattgatg gtgatttgac tgtctccggc ctttctcacc    3420
cgtttgaatc tttacctaca cattactcag gcattgcatt taaaatatat gagggttcta    3480 aaaatttta tccttgcgtt gaaataaagg cttctcccgc aaaagtatta cagggtcata    3540
atgtttttgg tacaaccgat ttagctttat gctctgaggc tttattgctt aattttgcta    3600 attcctttgcc ttgcctgtat gatttattgg atgttggaat cgcctgatgc ggtattttct    3660
ccttacgcat ctgtgcggta tttcacaccg catatggtgc actctcagta caatctgctc    3720
tgatgccgca tagttaagcc agccccgaca cccgccaaca cccgctgacg cgccctgacg    3780
ggcttgtctg ctcccggcat ccgcttacag acaagctgtg accgtctccg ggagctgcat    3840
gtgtcagagg ttttcaccgt catcaccgaa acgcgcgaga cgaaagggcc tcgtgatacg    3900
cctattttta taggttaatg tcatgataat aatggtttct tagacgtcag gtggcacttt    3960
tcggggaaat gtgcgcggaa cccctatttg tttattttct aaatacatt caaatatgta    4020 tccgctcatg agacaataac cctgataaat gcttcaataa tattgaaaaa ggaagagtat    4080
```

```
gagtattcaa catttccgtg tcgcccttat tccctttttt gcggcatttt gccttcctgt    4140
ttttgctcac ccagaaacgc tggtgaaagt aaaagatgct gaagatcagt tgggtgcacg    4200
agtgggttac atcgaactgg atctcaacag cggtaagatc cttgagagtt ttcgccccga    4260
agaacgtttt ccaatgatga gcacttttaa agttctgcta tgtggcgcgg tattatcccg    4320
tattgacgcc gggcaagagc aactcggtcg ccgcatacac tattctcaga atgacttggt    4380
tgagtactca ccagtcacag aaaagcatct tacggatggc atgacagtaa gagaattatg    4440
cagtgctgcc ataaccatga gtgataacac tgcggccaac ttacttctga caacgatcgg    4500
aggaccgaag gagctaaccg cttttttgca acatggggg  atcatgtaa ctcgccttga    4560 tcgttgggaa ccggagctga atgaagccat accaaacgac gagcgtgaca ccacgatgcc    4620
tgtagcaatg gcaacaacgt tgcgcaaact attaactggc gaactactta ctctagcttc    4680
ccggcaacaa ttaatagact ggatggaggc ggataaagtt gcaggaccac ttctgcgctc    4740
ggcccttccg gctggctggt ttattgctga taaatctgga gccggtgagc gtgggtctcg    4800
cggtatcatt gcagcactgg ggccagatgg taagccctcc cgtatcgtag ttatctacac    4860
gacggggagt caggcaacta tggatgaacg aaatagacag atcgctgaga taggtgcctc    4920
actgattaag cattggtaac tgtcagacca agtttactca tatatacttt agattgattt    4980
aaaacttcat ttttaattta aaaggatcta ggtgaagatc ctttttgata atctcatgac    5040
caaaatccct taacgtgagt tttcgttcca ctgagcgtca ccccgtag  aaaagatcaa    5100 aggatcttct tgagatcctt ttttctgcg  cgtaatctgc tgcttgcaaa caaaaaaacc    5160
accgctacca gcggtggttt gtttgccgga tcaagagcta ccaactcttt ttccgaaggt    5220
aactggcttc agcagagcgc agataccaaa tactgtcctt ctagtgtagc cgtagttagg    5280
ccaccacttc aagaactctg tagcaccgcc tacatacctc gctctgctaa tcctgttacc    5340
agtggctgct gccagtggcg ataagtcgtg tcttaccggg ttggactcaa gacgatagtt    5400
accggataag gcgcagcggt cgggctgaac ggggggttcg tgcacacagc ccagcttgga    5460
gcgaacgacc tacaccgaac tgagatacct acagcgtgag ctatgagaaa gcgccacgct    5520
tcccgaaggg agaaaggcgg acaggtatcc ggtaagcggc agggtcggaa caggagagcg    5580
cacgagggag cttccagggg gaaacgcctg gtatctttat agtcctgtcg ggtttcgcca    5640
cctctgactt gagcgtcgat ttttgtgatg ctcgtcaggg gggcggagcc tatgaaaaa    5700 cgccagcaac gcggcctttt tacggttcct ggccttttgc tggccttttg ctcacatgtt    5760
ctttcctgcg ttatcccctg attctgtgga taaccgtatt accgcctttg agtgagctga    5820
taccgctcgc cgcagccgaa cgaccgagcg cagcgagtca gtgagcgagg aagcggaaga    5880
gcgcccaata cgcaaaccgc ctctccccgc gcgttggccg attcattaat g              5931
```

<210> SEQ ID NO 16
<211> LENGTH: 18689
<212> TYPE: DNA
<213> ORGANISM: Artificial
<220> FEATURE:
<223> OTHER INFORMATION: Plasmid pXX6

<400> SEQUENCE: 16

```
ttattttgga ttgaagccaa tatgataatg agggggtgga gtttgtgacg tggcgcgggg      60
cgtgggaacg gggcgggtga cgtagtagtg tggcggaagt gtgatgttgc aagtgtggcg     120
gaacacatgt aagcgacgga tgtggcaaaa gtgacgtttt tggtgtgcgc ggatccacag     180
gacgggtgtg gtcgccatga tcgcgtagtc gatagtggct ccaagtagcg aagcgagcag     240
```

```
gactgggcgg cggccaaagc ggtcggacag tgctccgaga acgggtgcgc atagaaattg      300
catcaacgca tatagcgcta gcagcacgcc atagtgactg gcgatgctgt cggaatggac      360
gatatcccgc aagaggcccg gcagtaccgg cataaccaag cctatgccta cagcatccag      420
ggtgacggtg ccgaggatga cgatgagcgc attgttagat tcatacacg gtgcctgact       480 gcgttagcaa tttaactgtg ataaactacc gcattaaagc ttatcgataa gcttgatatc      540
gaattcctgc agcccggggg atccactagt tctagagcgg ccgccaccgc ggtggagctc      600
caattcgccc tatagtgagt cgtattacgc gcgctcactg gccgtcgttt tacaacgtcg      660
tgactgggaa accctggcg ttacccaact taatcgcctt gcagcacatc cccctttcgc       720
cagctggcgt aatagcgaag aggcccgcac cgatcgccct tcccaacagt tgcgcagcct      780
gaatggcgaa tgggacgcgc cctgtagcgg cgcattaagc gcggcgggtg tggtggttac      840
gcgcagcgtg accgctacac ttgccagcgc cctagcgccc gctcctttcg ctttcttccc      900
ttcctttctc gccacgttcg ccggctttcc ccgtcaagct ctaaatcggg gctcccttt       960 agggttccga tttagtgctt tacggcacct cgaccccaaa aaacttgatt agggtgatgg      1020
ttcacgtagt gggccatcgc cctgatagac ggtttttcgc cctttgacgt tggagtccac      1080
gttctttaat agtggactct tgttccaaac tggaacaaca ctcaaccta tctcggtcta      1140 ttcttttgat ttataaggga ttttgccgat ttcggcctat tggttaaaaa atgagctgat      1200
ttaacaaaaa tttaacgcga attttaacaa atattaacg cttacaattt aggtggcact      1260
tttcggggaa atgtgcgcgg aaccctatt tgtttatttt tctaaataca ttcaaatatg      1320
tatccgctca tgagacaata accctgataa atgcttcaat aatattgaaa aaggaagagt      1380
atgagtattc aacatttccg tgtcgccctt attccctttt ttgcggcatt ttgccttcct      1440 gttttgctc acccagaaac gctggtgaaa gtaaaagatg ctgaagatca gttgggtgca      1500
cgagtgggtt acatcgaact ggatctcaac agcggtaaga tccttgagag ttttcgcccc      1560
gaagaacgtt ttccaatgat gagcactttt aaagttctgc tatgtggcgc ggtattatcc      1620
cgtattgacg ccgggcaaga gcaactcggt cgccgcatac actattctca gaatgacttg      1680
gttgagtact caccagtcac agaaaagcat cttacggatg gcatgacagt aagagaatta      1740
tgcagtgctg ccataaccat gagtgataac actgcggcca acttacttct gacaacgatc      1800
ggaggaccga aggagctaac cgcttttttg cacaacatgg gggatcatgt aactcgcctt      1860
gatcgttggg aaccggagct gaatgaagcc ataccaaacg acgagcgtga ccaccacgatg     1920 cctgtagcaa tggcaacaac gttgcgcaaa ctattaactg gcgaactact tactctagct      1980
tcccggcaac aattaataga ctggatggag gcggataaag ttgcaggacc acttctgcgc      2040
tcggcccttc cggctggctg gtttattgct gataaatctg gagccggtga gcgtgggtct      2100
cgcggtatca ttgcagcact ggggccagat ggtaagccct cccgtatcgt agttatctac      2160
acgacgggga gtcaggcaac tatggatgaa cgaaatagac agatcgctga ataggtgcc       2220 tcactgatta agcattggta actgtcagac caagtttact catatatact ttagattgat      2280
ttaaaacttc attttaatt taaaaggatc taggtgaaga tcctttttga taatctcatg      2340
accaaaatcc cttaacgtga gttttcgttc cactgagcgt cagaccccgt agaaaagatc      2400
aaaggatctt cttgagatcc ttttttttctg cgcgtaatct gctgcttgca acaaaaaaa       2460 ccaccgctac cagcggtggt ttgtttgccg gatcaagagc taccaactct ttttccgaag      2520
gtaactggct tcagcagagc gcagatacca aatactgtcc ttctagtgta gccgtagtta      2580
```

```
ggccaccact tcaagaactc tgtagcaccg cctacatacc tcgctctgct aatcctgtta    2640
ccagtggctg ctgccagtgg cgataagtcg tgtcttaccg ggttggactc aagacgatag    2700
ttaccggata aggcgcagcg gtcgggctga acgggggggtt cgtgcacaca gcccagcttg   2760
gagcgaacga cctacaccga actgagatac ctacagcgtg agctatgaga aagcgccacg    2820
cttcccgaag ggagaaaggc ggacaggtat ccggtaagcg gcagggtcgg aacaggagag    2880
cgcacgaggg agcttccagg gggaaacgcc tggtatcttt atagtcctgt cgggtttcgc    2940
cacctctgac ttgagcgtcg atttttgtga tgctcgtcag gggggcggag cctatggaaa    3000
aacgccagca acgcggcctt tttacggttc ctggcctttt gctggccttt tgctcacatg    3060
ttctttcctg cgttatcccc tgattctgtg gataaccgta ttaccgcctt tgagtgagct    3120
gataccgctc gccgcagccg aacgaccgag cgcagcgagt cagtgagcga ggaagcggaa    3180
gagcgcccaa tacgcaaacc gcctctcccc gcgcgttggc cgattcatta atgcagctgg    3240
cacgacaggt ttcccgactg gaaagcgggc agtgagcgca acgcaattaa tgtgagttag    3300
ctcactcatt aggcaccccca ggctttacac tttatgcttc cggctcgtat gttgtgtgga   3360
attgtgagcg gataacaatt tcacacagga aacagctatg accatgatta cgccaagcgc    3420
gcaattaacc ctcactaaag ggaacaaaag ctgggtaccg gccccccccct cgaggtcgac   3480
agaagcacca tgtccttggg tccggcctgc tgaatgcgca ggcggtcggc catgccccag    3540
gcttcgtttt gacatcggcg caggtctttg tagtagtctt gcatgagcct ttctaccggc    3600
acttcttctt ctccttcctc ttgtcctgca tctcttgcat ctatcgctgc ggcggcggcg    3660
gagtttggcc gtaggtggcg ccctcttcct cccatgcgtg tgaccccgaa gcccctcatc    3720
ggctgaagca gggctaggtc ggcgacaacg cgctcggcta atatggcctg ctgcacctgc    3780
gtgagggtag actggaagtc atccatgtcc acaaagcggt ggtatgcgcc cgtgttgatg    3840
gtgtaagtgc agttggccat aacggaccag ttaacggtct ggtgacccgg ctgcgagagc    3900
tcggtgtacc tgagacgcga gtaagccctc gagtcaaata cgtagtcgtt gcaagtccgc    3960
accaggtact ggtatcccac caaaaagtgc ggcggcggct ggcggtagag gggccagcgt    4020
agggtggccg gggctccggg ggcgagatct tccaacataa ggcgatgata tccgtagatg    4080
tacctggaca tccaggtgat gccggcggcg gtggtggagg cgcgcggaaa gtcgcggacg    4140
cggttccaga tgttgcgcag cggcaaaaag tgctccatgg tcgggacgct ctggccggtc    4200
aggcgcgcgc aatcgttgac gctctagcgt gcaaaaggag agcctgtaag cgggcactct    4260
tccgtggtct ggtggataaa ttcgcaaggg tatcatggcg gacgaccggg gttcgagccc    4320
cgtatccggc cgtccgccgt gatccatgcg gttaccgccc gcgtgtcgaa cccaggtgtg    4380
cgacgtcaga caacgggggga gtgctccttt tggcttcctt ccaggcgcgg cggctgctgc    4440
gctagctttt ttggccactg gccgcgcgca gcgtaagcgg ttaggctgga aagcgaaagc    4500
attaagtggc tcgctccctg tagccggagg gttatttttcc aagggttgag tcgcgggacc    4560
cccggttcga gtctcggacc ggccggactg cggcgaacgg gggtttgcct ccccgtcatg    4620
caagaccccg cttgcaaatt cctccggaaa cagggacgag ccccttttttt gcttttccca    4680
gatgcatccg gtgctgcggc agatgcgccc cctcctcag cagcggcaag agcaagagca    4740
gcggcagaca tgcagggcac cctcccctcc tcctaccgcg tcaggagggg cgacatccgc    4800
ggttgacgcg gcagcagatg gtgattacga acccccgcgg cgccgggccc ggcactacct    4860
ggacttggag gagggcgagg gcctggcgcg gctaggagcg ccctctcctg agcggtaccc    4920
aagggtgcag ctgaagcgtg atacgcgtga ggcgtacgtg ccgcggcaga acctgtttcg    4980
```

```
cgaccgcgag ggagaggagc ccgaggagat gcgggatcga aagttccacg cagggcgcga    5040
gctgcggcat ggcctgaatc gcgagcggtt gctgcgcgag gaggactttg agcccgacgc    5100
gcgaaccggg attagtcccg cgcgcgcaca cgtggcggcc gccgacctgg taaccgcata    5160
cgagcagacg gtgaaccagg agattaactt tcaaaaaagc tttaacaacc acgtgcgtac    5220
gcttgtggcg cgcgaggagg tggctatagg actgatgcat ctgtgggact ttgtaagcgc    5280
gctggagcaa aacccaaata gcaagccgct catggcgcag ctgttcctta tagtgcagca    5340
cagcagggac aacgaggcat tcagggatgc gctgctaaac atagtagagc ccgagggccg    5400
ctggctgctc gatttgataa acatcctgca gagcatagtg gtgcaggagc gcagcttgag    5460
cctggctgac aaggtggccg ccatcaacta ttccatgctt agcctgggca agttttacgc    5520
ccgcaagata taccataccc cttacgttcc catagacaag gaggtaaaga tcgaggggtt    5580
ctacatgcgc atggcgctga aggtgcttac cttgagcgac gacctgggcg tttatcgcaa    5640
cgagcgcatc cacaaggccg tgagcgtgag ccggcggcgc gagctcagcg accgcgagct    5700
gatgcacagc ctgcaaaggg ccctggctgg cacgggcagc ggcgatagag aggccgagtc    5760
ctactttgac gcgggcgctg acctgcgctg ggccccaagc cgacgcgccc tggaggcagc    5820
tggggccgga cctgggctgg cggtggcacc cgcgcgcgct ggcaacgtcg gcggcgtgga    5880
ggaatatgac gaggacgatg agtacgagcc agaggacggc gagtactaag cggtgatgtt    5940
tctgatcaga tgatgcaaga cgcaacggac ccggcggtgc gggcggcgct gcagagccag    6000
ccgtccggcc ttaactccac ggacgactgg cgccaggtca tggaccgcat catgtcgctg    6060
actgcgcgca atcctgacgc gttccggcag cagccgcagg ccaaccggct ctccgcaatt    6120
ctggaagcgg tggtcccggc gcgcgcaaac cccacgcacg agaaggtgct ggcgatcgta    6180
aacgcgctgg ccgaaaacag ggccatccgg cccgacgagg ccggcctggt ctacgacgcg    6240
ctgcttcagc gcgtggctcg ttacaacagc ggcaacgtgc agaccaacct ggaccggctg    6300
gtgggggatg tgcgcgaggc cgtggcgcag cgtgagcgcg cgcagcagca gggcaacctg    6360
ggctccatgg ttgcactaaa cgccttcctg agtacacagc ccgccaacgt gccgcgggga    6420
caggaggact acaccaactt tgtgagcgca ctgcggctaa tggtgactga cacaccgcaa    6480
agtgaggtgt accagtctgg gccagactat ttttttccaga ccagtagaca aggcctgcag    6540
accgtaaacc tgagccaggc tttcaaaaac ttgcaggggc tgtgggggt gcgggctccc    6600 acaggcgacc gcgcgaccgt gtctagcttg ctgacgccca actcgcgcct gttgctgctg    6660
ctaatagcgc ccttcacgga cagtggcagc gtgtcccggg acacataccct aggtcacttg    6720 ctgacactgt accgcgaggc cataggtcag gcgcatgtgg acgagcatac tttccaggag    6780
attacaagtg tcagccgcgc gctggggcag gaggacacgg gcagcctgga ggcaacccta    6840
aactacctgc tgaccaaccg gcggcagaag atcccctcgt tgcacagttt cgcacccttt    6900
ggcgcatccc attctccagt aactttatgt ccatggcgc actcacagac ctgggccaaa    6960
accttctcta cgccaactcc gcccacgcgc tagacatgac ttttgaggtg gatcccatgg    7020
acgagcccac ccttctttat gttttgtttg aagtctttga cgtggtccgt gtgcaccggc    7080
cgcaccgcgg cgtcatcgaa accgtgtacc tgcgcacgcc cttctcggcc ggcaacgcca    7140
caacataaag aagcaagcaa catcaacaac agctgccgcc atgggctcca gtgagcagga    7200
actgaaagcc attgtcaaag atcttggttg tgggccatat tttttgggca cctatgacaa    7260
gcgctttcca ggctttgttt ctccacacaa gctcgcctgc gccatagtca atacggccgg    7320
```

```
tcgcgagact gggggcgtac actggatggc ctttgcctgg aacccgcact caaaaacatg   7380 ctacctctt  gagcccttg  gctttctga   ccagcgactc aagcaggttt accagttga    7440 gtacgagtca ctcctgcgcc gtagcgccat tgcttcttcc cccgaccgct gtataacgct   7500
ggaaaagtcc acccaaagcg tacaggggcc caactcggcc gcctgtggac tattctgctg   7560
catgtttctc cacgcctttg ccaactggcc ccaaactccc atggatcaca accccaccat   7620
gaaccttatt accggggtac ccaactccat gctcaacagt ccccaggtac agcccaccct   7680
gcgtcgcaac caggaacagc tctacagctt cctggagcgc cactcgccct acttccgcag   7740
ccacagtgcg cagattagga gcgccacttc tttttgtcac ttgaaaaaca tgtaaaaata   7800
atgtactaga gacactttca ataaaggcaa atgcttttat ttgtacactc tcgggtgatt   7860
atttaccccc acccttgccg tctgcgccgt ttaaaaatca aaggggttct gccgcgcatc   7920
gctatgcgcc actggcaggg acgttgcg   atactggtgt ttagtgctcc acttaaactc   7980
aggcacaacc atccgcggca gctcggtgaa gttttcactc cacaggctgc gcaccatcac   8040 caacgcgtt  agcaggtcgg gcgccgatat cttgaagtcg cagttggggc ctccgccctg   8100
cgcgcgcgag ttgcgataca cagggttgca gcactggaac actatcagcg ccgggtggtg   8160
cacgctggcc agcacgctct tgtcggagat cagatccgcg tccaggtcct ccgcgttgct   8220
cagggcgaac ggagtcaact ttggtagctg ccttcccaaa aagggcgcgt gcccaggctt   8280
tgagttgcac tcgcaccgta gtggcatcaa aaggtgaccg tgcccggtct gggcgttagg   8340
atacagcgcc tgcataaaag ccttgatctg cttaaaagcc acctgagcct tgcgccttc    8400 agagaagaac atgccgcaag acttgccgga aaactgattg gccggacagg ccgcgtcgtg   8460
cacgcagcac cttgcgtcgg tgttggagat ctgcaccaca tttcggcccc accggttctt   8520
cacgatcttg gccttgctag actgctcctt cagcgcgcgc tgcccgtttt cgctcgtcac   8580
atccatttca atcacgtgct ccttattat  cataatgctt ccgtgtagac acttaagctc   8640
gccttcgatc tcagcgcagc ggtgcagcca caacgcgcag cccgtgggct cgtgatgctt   8700
gtaggtcacc tctgcaaacg actgcaggta cgcctgcagg aatcgcccca tcatcgtcac   8760
aaaggtcttg ttgctggtga aggtcagctg caacccgcgg tgctcctcgt tcagccaggt   8820
cttgcatacg gccgccagag cttccacttg gtcaggcagt agtttgaagt tcgcctttag   8880
atcgttatcc acgtggtact tgtccatcag cgcgcgcgca gcctccatgc ccttctccca   8940
cgcagacacg atcggcacac tcagcgggtt catcaccgta atttcacttt ccgcttcgct   9000
gggctcttcc tcttcctctt gcgtccgcat accacgcgcc actgggtcgt cttcattcag   9060
ccgccgcact gtgcgcttac ctcctttgcc atgcttgatt agcaccggtg ggttgctgaa   9120
acccaccatt gtagcgcca  catcttctct ttcttcctcg ctgtccacga ttacctctgg   9180
tgatggcggg cgctcgggct tgggagaagg gcgcttcttt ttcttcttgg gcgcaatggc   9240
caaatccgcc gccgaggtcg atggccgcgg gctgggtgtg gcggcacca  gcgcgtcttg   9300 tgatgagtct tcctcgtcct cggactcgat acgccgcctc atccgctttt tgggggcgc    9360 ccggggaggc ggcggcgacg gggacgggga cgacgtcc   tccatggttg ggggacgtcg   9420
cgccgcaccg cgtccgcgct cggggtggt  ttcgcgctgc tcctcttccc gactggccat   9480
ttccttctcc tataggcaga aaagatcat  ggagtcagtc gagaagaagg acagcctaac   9540 cgcccctct  gagttcgcca ccaccgcctc caccgatgcc gccaacgcgc ctaccacctt   9600
ccccgtcgag gcacccccgc ttgaggagga ggaagtgatt atcgagcagg acccaggttt   9660
tgtaagcgaa gacgacgagg accgctcagt accaacagag gataaaaagc aagaccagga   9720
```

```
caacgcagag gcaaacgagg aacaagtcgg gcgggggggac gaaaggcatg gcgactacct    9780
agatgtggga gacgacgtgc tgttgaagca tctgcagcgc cagtgcgcca ttatctgcga    9840
cgcgttgcaa gagcgcagcg atgtgccccct cgccatagcg gatgtcagcc ttgcctacga   9900
acgccaccta ttctcaccgc gcgtaccccc caaacgccaa gaaaacggca catgcgagcc    9960
caacccgcgc ctcaacttct accccgtatt tgccgtgcca gaggtgcttg ccacctatca   10020 catcttttc caaaactgca agatacccct atcctgccgt gccaaccgca gccgagcgga    10080
caagcagctg gccttgcggc agggcgctgt catacctgat atcgcctcgc tcaacgaagt   10140
gccaaaaatc tttgagggtc ttggacgcga cgagaagcgc gcggcaaacg ctctgcaaca   10200
ggaaaacagc gaaaatgaaa gtcactctgg agtgttggtg aactcgagg gtgacaacgc    10260 gcgcctagcc gtactaaaac gcagcatcga ggtcacccac tttgcctacc cggcacttaa   10320 cctaccccc aaggtcatga gcacagtcat gagtgagctg atcgtgcgcc gtgcgcagcc    10380
cctggagagg gatgcaaatt tgcaagaaca aacagaggag ggcctacccg cagttggcga   10440
cgagcagcta gcgcgctggc ttcaaacgcg cgagcctgcc gacttggagg agcgacgcaa   10500
actaatgatg gccgcagtgc tcgttaccgt ggagcttgag tgcatgcagc ggttctttgc    10560
tgacccggag atgcagcgca agctagagga acattgcac tacaccttc gacagggcta     10620 cgtacgccag gcctgcaaga tctccaacgt ggagctctgc aacctggtct cctaccttgg   10680
aattttgcac gaaaaccgcc ttgggcaaaa cgtgcttcat tccacgctca agggcgaggc   10740
gcgccgcgac tacgtccgcg actgcgttta cttatttcta tgctacacct ggcagacggc   10800
catgggcgtt tggcagcagt gcttggagga gtgcaacctc aaggagctgc agaaactgct   10860
aaagcaaaac ttgaaggacc tatggacggc cttcaacgag cgctccgtgg ccgcgcacct   10920
ggcggacatc attttccccg aacgcctgct taaaaccctg caacagggtc tgccagactt   10980
caccagtcaa agcatgttgc agaactttag gaactttatc ctagagcgct caggaatctt   11040
gcccgccacc tgctgtgcac ttcctagcga ctttgtgccc attaagtacc gcgaatgccc   11100
tccgccgctt tggggccact gctaccttct gcagctagcc aactaccttg cctaccactc   11160
tgacataatg gaagacgtga gcggtgacgg tctactggag tgtcactgtc gctgcaacct   11220 atgcacccg caccgctccc tggttttgcaa ttcgcagctg cttaacgaaa gtcaaattat    11280
cggtaccttt gagctgcagg gtccctcgcc tgacgaaaag tccgcggctc cggggttgaa    11340
actcactccg gggctgtgga cgtcggctta ccttcgcaaa tttgtacctg aggactacca    11400
cgcccacgag attaggttct acgaagacca atcccgcccg ccaaatgcgg agcttaccgc    11460
ctgcgtcatt acccagggcc acattcttgg ccaattgcaa gccatcaaca agcccgcca    11520 agagtttctg ctacgaaagg gacggggggt ttacttggac ccccagtccg gcgaggagct   11580 caaccccaatc cccccgccgc cgcagcccta tcagcagcag ccgcgggccc ttgcttccca   11640
ggatggcacc caaaaagaag ctgcagctgc cgccgccacc cacggacgag gaggaatact   11700
gggacagtca ggcagaggag gttttggacg aggaggagga ggacatgatg gaagactggg   11760
agagcctaga cgaggaagct tccgaggtcg aagaggtgtc agacgaaaca ccgtcaccct   11820
cggtcgcatt cccctcgccg gcgccccaga atcggcaac cggttccagc atggctacaa    11880
cctccgctcc tcaggcgccg ccggcactgc ccgttcgccg acccaaccgt agatgggaca   11940 ccactgaac cagggccggt aagtccaagc agccgccgcc gttagcccaa gagcaacaac   12000
agcgccaagg ctaccgctca tggcgcgggc acaagaacgc catagttgct tgcttgcaag   12060
```

-continued

```
actgtggggg caacatctcc ttcgcccgcc gctttcttct ctaccatcac ggcgtggcct    12120
tcccccgtaa catcctgcat tactaccgtc atctctacag cccatactgc accggcggca    12180
gcggcagcgg cagcaacagc agcggccaca cagaagcaaa ggcgaccgga tagcaagact    12240
ctgacaaagc ccagaaaatc cacagcggcg gcagcagcag gaggaggagc gctgcgtctg    12300
gcgcccaacg aacccgtatc gacccgcgag cttagaaaca ggattttcc cactctgtat     12360 gctatatttc aacagagcag gggccaagaa caagagctga aaataaaaaa caggtctctg    12420
cgatccctca cccgcagctg cctgtatcac aaaagcgaag atcagcttcg gcgcacgctg    12480
gaagacgcgg aggctctctt cagtaaatac tgcgcgctga ctcttaagga ctagtttcgc    12540
gccctttctc aaatttaagc gcgaaaacta cgtcatctcc agcggccaca cccggcgcca    12600
gcacctgtcg tcagcgccat tatgagcaag gaaattccca cgccctacat gtggagttac    12660
cagccacaaa tgggacttgc ggctggagct gcccaagact actcaacccg aataaactac    12720
atgagcgcgg gaccccacat gatatcccgg gtcaacggaa tccgcgccca ccgaaaccga    12780
attctcttgg aacaggcggc tattaccacc acacctcgta ataaccttaa tccccgtagt    12840
tggcccgctg ccctggtgta ccaggaaagt cccgctccca ccactgtggt acttcccaga    12900
gacgcccagg ccgaagttca gatgactaac tcaggggcgc agcttgcggg cggctttcgt    12960
cacagggtgc ggtcgcccgg gcagggtata actcacctga caatcagagg gcgaggtatt    13020
cagctcaacg acgagtcggt gagctcctcg cttggtctcc gtccggacgg gacatttcag    13080
atcggcggcg ccggccgtcc ttcattcacg cctcgtcagg caatcctaac tctgcagacc    13140
tcgtcctctg agccgcgctc tggaggcatt ggaactctgc aatttattga ggagtttgtg    13200
ccatcggtct actttaaccc cttctcggga cctcccggcc actatccgga tcaatttatt    13260
cctaactttg acgcggtaaa ggactcggcg gacggctacg actgaatgtt aagtggagag    13320
gcagagcaac tgcgcctgaa acacctggtc cactgtcgcc gccacaagtg ctttgcccgc    13380
gactccggta gttttgcta ctttgaattg cccgaggatc atatcgaggg cccggcgcac     13440
ggcgtccggc ttaccgccca gggagagctt gcccgtagcc tgattcggga gtttacccag    13500 cgcccctgc tagttgagcg ggacagggga ccctgtgttc tcactgtgat ttgcaactgt      13560
cctaaccttg gattacatca ccctttaac taataaaaaa aaataataaa gcatcactta      13620
cttaaaatca gttagcaaat ttctgtccag tttattcagc agcacctcct tgccctcctc    13680
ccagctctgg tattgcagct tcctcctggc tgcaaacttt ctccacaatc taaatggaat    13740
gtcagtttcc tcctgttcct gtccatccgc acccactatc ttcatgttgt tgcagatgaa    13800
gcgcgcaaga ccgtctgaag ataccttcaa ccccgtgtat ccatatgaca cggaaaccgg    13860
tcctccaact gtgccttttc ttactcctcc ctttgtatcc cccaatgggt ttcaagagag    13920 tcccctggg gtactctctt tgcgcctatc cgaacctcta gttacctcca atggcatgct      13980
tgcgctcaaa atgggcaacg gcctctctct ggacgaggcc ggcaacctta cctcccaaaa    14040
tgtaaccact gtgagcccac ctctcaaaaa aaccaagtca aacataaacc tggaaatatc    14100
tgcacccctc acagttacct cagaagccct aactgtggct gccgccgcac ctctaatggt    14160
cgcgggcaac acactcacca tgcaatcaca ggccccgcta accgtgcacg actccaaact    14220
tagcattgcc acccaaggac ccctcacagt gtcagaagga aagctagccc tgcaaacatc    14280 aggcccctc accaccaccg atagcagtac ccttactatc actgcctcac cccctctaac      14340
tactgccact ggtagcttgg gcattgactt gaaagagccc atttatacac aaaatgaaa      14400 actaggacta aagtacgggg ctcctttgca tgtaacagac gacctaaaca ctttgaccgt    14460
```

```
agcaactggt ccaggtgtga ctattaataa tacttccttg caaactaaag ttactggagc    14520
cttgggtttt gattcacaag gcaatatgca acttaatgta gcaggaggac taaggattga    14580
ttctcaaaac agacgcctta tacttgatgt tagttatccg tttgatgctc aaaaccaact    14640
aaatctaaga ctaggacagg gccctctttt tataaactca gcccacaact tggatattaa    14700
ctacaacaaa ggcctttact tgtttacagc ttcaaacaat tccaaaaagc ttgaggttaa    14760
cctaagcact gccaagggt tgatgtttga cgctacagcc atagccatta atgcaggaga    14820
tgggcttgaa tttggttcac ctaatgcacc aaacacaaat cccctcaaaa caaaaattgg    14880
ccatggccta gaatttgatt caaacaaggc tatggttcct aaactaggaa ctggccttag    14940
ttttgacagc acaggtgcca ttacagtagg aaacaaaaat aatgataagc taactttgtg    15000
gaccacacca gctccatctc ctaactgtag actaaatgca gagaaagatg ctaaactcac    15060
tttggtctta acaaaatgtg gcagtcaaat acttgctaca gtttcagttt tggctgttaa    15120
aggcagtttg gctccaatat ctggaacagt tcaaagtgct catcttatta taagatttga    15180
cgaaaatgga gtgctactaa acaattcctt cctggaccca gaatattgga actttagaaa    15240
tggagatctt actgaaggca cagcctatac aaacgctgtt ggatttatgc ctaacctatc    15300
agcttatcca aaatctcacg gtaaaactgc caaaagtaac attgtcagtc aagtttactt    15360
aaacggagac aaaactaaac ctgtaacact aaccattaca ctaaacggta cacaggaaac    15420
aggagacaca actccaagtg catactctat gtcattttca tgggactggt ctggccacaa    15480
ctacattaat gaaatatttg ccacatcctc ttacactttt tcatacattg cccaagaata    15540
aagaatcgtt tgtgttatgt ttcaacgtgt ttattttttca attgcagaaa atttcaagtc    15600 attttttcatt cagtagtata gccccaccac cacatagctt atacagatca ccgtaccttta   15660 atcaaactca cagaaccta gtattcaacc tgccacctcc ctcccaacac acagagtaca    15720
cagtcctttc tccccggctg ccttaaaaa gcatcatatc atgggtaaca gacatattct    15780
taggtgttat attccacacg gtttcctgtc gagccaaacg ctcatcagtg atattaataa    15840
actccccggg cagctcactt aagttcatgt cgctgtccag ctgctgagcc acaggctgct    15900
gtccaacttg cggttgctta acgggcggcg aaggagaagt ccacgcctac atgggggtag    15960
agtcataatc gtgcatcagg atagggcggt ggtgctgcag cagcgcgcga ataaactgct    16020
gccgccgccg ctccgtcctg caggaataca acatggcagt ggtctcctca gcgatgattc    16080
gcaccgcccg cagcataagg cgccttgtcc tccgggcaca gcagcgcacc ctgatctcac    16140
ttaaatcagc acagtaactg cagcacagca ccacaatatt gttcaaaatc ccacagtgca    16200
aggcgctgta tccaaagctc atggcgggga ccacagaacc cacgtggcca tcataccaca    16260
agcgcaggta gattaagtgg cgaccctca taaaacgct ggacataaac attacctctt    16320
ttggcatgtt gtaattcacc acctcccggt accatataaa cctctgatta aacatggcgc    16380
catccaccac catcctaaac cagctggcca aaacctgccc gccggctata cactgcaggg    16440
aaccgggact ggaacaatga cagtggagag cccaggactc gtaaccatgg atcatcatgc    16500
tcgtcatgat atcaatgttg gcacaacaca ggcacacgtg catacacttc ctcaggatta    16560
caagctcctc ccgcgttaga accatatccc agggaacaac ccattcctga atcagcgtaa    16620
atcccacact gcagggaaga cctcgcacgt aactcacgtt gtgcattgtc aaagtgttac    16680
attcgggcag cagcggatga tcctccagta tggtagcgcg ggtttctgtc tcaaaaggag    16740
gtagacgatc cctactgtac ggagtgcgcc gagacaaccg agatcgtgtt ggtcgtagtg    16800
```

```
tcatgccaaa tggaacgccg gacgtagtca tatttcctga agcaaaacca ggtgcgggcg    16860
tgacaaacag atctgcgtct ccggtctcgc cgcttagatc gctctgtgta gtagttgtag    16920
tatatccact ctctcaaagc atccaggcgc ccctggctt cgggttctat gtaaactcct     16980
tcatgcgccg ctgccctgat aacatccacc accgcagaat aagccacacc cagccaacct    17040
acacattcgt tctgcgagtc acacacggga ggagcgggaa gagctggaag aaccatgttt    17100
ttttttttat tccaaaagat tatccaaaac ctcaaaatga agatctatta agtgaacgcg    17160
ctcccctccg gtggcgtggt caaactctac agccaaagaa cagataatgg catttgtaag    17220
atgttgcaca atggcttcca aaaggcaaac ggccctcacg tccaagtgga cgtaaaggct    17280
aaacccttca gggtgaatct cctctataaa cattccagca ccttcaacca tgcccaaata    17340
attctcatct cgccaccttc tcaatatatc tctaagcaaa tcccgaatat taagtccggc    17400
cattgtaaaa atctgctcca gagcgccctc caccttcagc ctcaagcagc gaatcatgat    17460
tgcaaaaatt caggttcctc acagacctgt ataagattca aaagcggaac attaacaaaa    17520
ataccgcgat cccgtaggtc ccttcgcagg gccagctgaa cataatcgtg caggtctgca    17580
cggaccagcg cggccacttc cccgccagga accttgacaa agaacccac actgattatg      17640
acacgcatac tcggagctat gctaaccagc gtagccccga tgtaagcttt gttgcatggg    17700
cggcgatata aaatgcaagg tgctgctcaa aaaatcaggc aaagcctcgc gcaaaaaaga    17760
aagcacatcg tagtcatgct catgcagata aaggcaggta agctccggaa ccaccacaga    17820
aaaagacacc atttttctct caaacatgtc tgcgggtttc tgcataaaca caaataaaa     17880
taacaaaaaa acatttaaac attagaagcc tgtcttacaa caggaaaaac aacccttata    17940
agcataagac ggactacggc catgccggcg tgaccgtaaa aaaactggtc accgtgatta    18000
aaaagcacca ccgacagctc ctcggtcatg tccggagtca taatgtaaga ctcggtaaac    18060
acatcaggtt gattcatcgg tcagtgctaa aaagcgaccg aaatagcccg ggggaataca    18120
tacccgcagg cgtagagaca acattacagc ccccatagga ggtataacaa aattaatagg    18180
agagaaaaac acataaacac ctgaaaaacc ctcctgccta ggcaaaatag caccctcccg    18240
ctccagaaca acatacagcg cttcacagcg gcagcctaac agtcagcctt accagtaaaa    18300
aagaaaacct attaaaaaaa caccactcga cacggcacca gctcaatcag tcacagtgta    18360
aaaaagggcc aagtgcagag cgagtatata taggactaaa aaatgacgta acggttaaag    18420
tccacaaaaa acacccagaa aaccgcacgc gaacctacgc ccagaaacga aagccaaaaa    18480
acccacaact tcctcaaatc gtcacttccg ttttcccacg ttacgtaact tcccattta     18540
agaaaactac aattcccaac acatacaagt tactccgccc taaaacctac gtcacccgcc    18600
ccgttcccac gccccgcgcc acgtcacaaa ctccacccc tcattatcat attggcttca     18660
atccaaaata aggtatatta ttgatgatg                                       18689

<210> SEQ ID NO 17
<211> LENGTH: 7335
<212> TYPE: DNA
<213> ORGANISM: Artificial
<220> FEATURE:
<223> OTHER INFORMATION: Plasmid pREp2Cap10

<400> SEQUENCE: 17
gattaaggtc cccagcgacc ttgacgagca tctgcccggc atttctgaca gctttgtgaa      60
ctgggtggcc gagaaggaat gggagttgcc gccagattct gacatggatc tgaatctgat    120
tgagcaggca cccctgaccg tggccgagaa gctgcagcgc gactttctga cggaatggcg    180
```

```
ccgtgtgagt aaggccccgg aggctctttt cttttgtgcaa tttgagaagg gagagagcta    240
cttccacatg cacgtgctcg tggaaaccac cggggtgaaa tccatggttt tgggacgttt    300
cctgagtcag attcgcgaaa aactgattca gagaatttac cgcgggatcg agccgacttt    360
gccaaactgg ttcgcggtca caaagaccag aaatggcgcc ggaggcggga caaggtggt    420
ggatgagtgc tacatcccca attacttgct ccccaaaacc cagcctgagc tccagtgggc    480
gtggactaat atggaacagt atttaagcgc ctgtttgaat ctcacggagc gtaaacggtt    540
ggtggcgcag catctgacgc acgtgtcgca gacgcaggag cagaacaaag agaatcagaa    600
tcccaattct gatgcgccgg tgatcagatc aaaaacttca gccaggtaca tggagctggt    660
cgggtggctc gtggacaagg ggattacctc ggagaagcag tggatccagg aggaccaggc    720
ctcatacatc tccttcaatg cggcctccaa ctcgcggtcc caaatcaagg ctgccttgga    780
caatgcggga agattatga gcctgactaa aaccgccccc gactacctgg tgggccagca    840
gcccgtggag gacatttcca gcaatcggat ttataaaatt ttggaactaa cgggtacga    900
tccccaatat gcggcttccg tctttctggg atgggccacg aaaaagttcg gcaagaggaa    960
caccatctgg ctgtttgggc ctgcaactac cgggaagacc aacatcgcgg aggccatagc    1020
ccacactgtg cccttctacg ggtgcgtaaa ctggaccaat gagaactttc ccttcaacga    1080
ctgtgtcgac aagatggtga tctggtggga ggaggggaag atgaccgcca aggtcgtgga    1140
gtcggccaaa gccattctcg gaggaagcaa ggtgcgcgtg gaccagaaat gcaagtcctc    1200
ggcccagata gacccgactc ccgtgatcgt cacctccaac accaacatgt gcgccgtgat    1260
tgacgggaac tcaacgacct tcgaacacca gcagccgttg caagaccgga tgttcaaatt    1320
tgaactcacc cgccgtctgg atcatgactt tgggaaggtc accaagcagg aagtcaaaga    1380
cttttttccgg tgggcaaagg atcacgtggt tgaggtggag catgaattct acgtcaaaaa    1440
gggtggagcc aagaaaagac ccgccccag tgacgcagat ataagtgagc ccaaacgggt    1500
gcgcgagtca gttgcgcagc catcgacgtc agacgcggaa gcttcgatca actacgcaga    1560
caggtaccaa aacaaatgtt ctcgtcacgt gggcatgaat ctgatgctgt ttccctgcag    1620
acaatgcgag agaatgaatc agaattcaaa tatctgcttc actcacggac agaaagactg    1680
tttagagtgc tttcccgtgt cagaatctca acccgtttct gtcgtcaaaa aggcgtatca    1740
gaaactgtgc tacattcatc atatcatggg aaaggtgcca gacgcttgca ctgcctgcga    1800
tctggtcaat gtggatttgg atgactgcat cttttgaacaa taaatgattt aaatcaggta    1860
tggctgccga tggttatctt ccagattggc tcgaggacaa cctctctgag ggcattcgcg    1920
agtggtggga cttgaaacct ggagccccga aacccaaagc caaccagcaa agcaggacg    1980
acggccgggt tctggtgctt cctggctaca agtacctcgg acccttcaac ggactcgaca    2040
aggggagcc cgtcaacgcg gcggacgcag cggccctcga gcacgacaag gcctacgacc    2100
agcagctcaa agcgggtgac aatccgtacc tgcggtataa ccacgccgac gccgagtttc    2160
aggagcgtct gcaagaagat acgtcttttg ggggcaacct cgggcgagca gtcttccagg    2220
ccaagaagcg ggttctcgaa cctctcggtc tggttgagga aggcgctaag acggctcctg    2280
gaaagaagag accggtagag ccatcacccc agcgttctcc agactcctct acgggcatcg    2340
gcaagaaagg ccagcagccc gcgaaaaaga gactcaactt tgggcagact ggcgactcag    2400
agtcagtgcc cgaccctcaa ccaatcgag aaccccccgc aggcccctct ggtctgggat    2460
ctggtacaat ggctgcaggc ggtggcgctc caatggcaga caataacgaa ggcgccgacg    2520
```

```
gagtgggtag ttcctcagga aattggcatt gcgattccac atggctgggc gacagagtca    2580
tcaccaccag cacccgaacc tgggccctcc ccacctacaa caaccacctc tacaagcaaa    2640
tctccaacgg gacttcggga ggaagcacca acgacaacac ctacttcggc tacagcaccc    2700
cctgggggta ttttgacttt aacagattcc actgccactt ctcaccacgt gactggcagc    2760
gactcatcaa caacaactgg ggattccggc ccaagagact caacttcaag ctcttcaaca    2820
tccaggtcaa ggaggtcacg cagaatgaag gcaccaagac catcgccaat aaccttacca    2880
gcacgattca ggtctttacg gactcggaat accagctccc gtacgtcctc ggctctgcgc    2940
accagggctg cctgcctccg ttcccggcgg acgtcttcat gattcctcag tacgggtacc    3000
tgactctgaa caatggcagt caggccgtgg gccgttcctc cttctactgc ctggagtact    3060
ttccttctca aatgctgaga acgggcaaca actttgagtt cagctaccag tttgaggacg    3120
tgccttttca cagcagctac gcgcacagcc aaagcctgga ccggctgatg aaccccctca    3180
tcgaccagta cctgtactac ctgtctcgga ctcagtccac gggaggtacc gcaggaactc    3240
agcagttgct atttctcag gccgggccta ataacatgtc ggctcaggcc aaaaactggc    3300
tacccgggcc ctgctaccgg cagcaacgcg tctccacgac actgtcgcaa ataacaaca    3360 gcaactttgc ctggaccggt gccaccaagt atcatctgaa tggcagagac tctctggtaa    3420
atcccggtgt cgctatggca acccacaagg acgacgaaga gcgattttt ccgtccagcg    3480 gagtcttaat gtttgggaaa cagggagctg aaaagacaa cgtggactat agcagcgtta    3540
tgctaaccag tgaggaagaa attaaaacca ccaacccagt ggccacagaa cagtacggcg    3600
tggtggccga taacctgcaa cagcaaaacg ccgctcctat tgtagggggcc gtcaacagtc    3660 aaggagcctt acctggcatg gtctggcaga accgggacgt gtacctgcag ggtcctatct    3720
gggccaagat tcctcacacg gacggaaact ttcatccctc gccgctgatg ggaggctttg    3780
gactgaaaca cccgcctcct cagatcctga ttaagaatac acctgttccc gcggatcctc    3840
caactacctt cagtcaagct aagctggcgt cgttcatcac gcagtacagc accgacagg    3900 tcagcgtgga aattgaatgg gagctgcaga agaaaacag caaacgctgg aacccagaga    3960
ttcaatacac ttccaactac tacaaatcta caaatgtgga ctttgctgtt aacacagatg    4020
gcacttattc tgagcctcgc cccatcggca cccgttacct cacccgtaat ctgtaattgc    4080
ttgttaatca ataaaccggt tgattcgttt cagttgaact ttggtctctg catatgcgca    4140
attcgtttaa acctgcagga ctagagtcct gtattagagg tcacgtgagt gttttgcgac    4200
attttgcgac accatgtggt cacgctgggt atttaagccc gagtgagcac gcagggtctc    4260
cattttgaag cgggaggttt gaacgcgcag ccgccaagcc gaattctgca gatatccatc    4320
acactggcgg ccgctcgact agagcggccg ccaccgcgt ggagctccag cttttgttcc    4380
ctttagtgag ggttaattgc gcgcttggcg taatcatggt catagctgtt tcctgtgtga    4440
aattgttatc cgctcacaat tccacacaac atacgagccg aagcataaa gtgtaaagcc    4500 tggggtgcct aatgagtgag ctaactcaca ttaattgcgt tgcgctcact gcccgctttc    4560
cagtcgggaa acctgtcgtg ccagctgcat taatgaatcg gccaacgcgc ggggagaggc    4620
ggtttgcgta ttgggcgctc ttccgcttcc tcgctcactg actcgctgcg ctcggtcgtt    4680
cggctgcggc gagcggtatc agctcactca aaggcggtaa tacggttatc cacagaatca    4740
ggggataacg caggaaagaa catgtgagca aaaggccagc aaaaggccag gaaccgtaaa    4800
aaggccgcgt tgctggcgtt tttccatagg ctccgccccc ctgacgagca tcacaaaaat    4860
cgacgctcaa gtcagaggtg gcgaaacccg acaggactat aaagatacca ggcgtttccc    4920
```

```
cctggaagct ccctcgtgcg ctctcctgtt ccgaccctgc cgcttaccgg atacctgtcc   4980
gcctttctcc cttcgggaag cgtggcgctt tctcatagct cacgctgtag gtatctcagt   5040
tcggtgtagg tcgttcgctc caagctgggc tgtgtgcacg aacccccgt tcagcccgac    5100 cgctgcgcct tatccggtaa ctatcgtctt gagtccaacc cggtaagaca cgacttatcg   5160
ccactggcag cagccactgg taacaggatt agcagagcga ggtatgtagg cggtgctaca   5220
gagttcttga agtggtggcc taactacggc tacactagaa gaacagtatt tggtatctgc   5280
gctctgctga agccagttac cttcggaaaa agagttggta gctcttgatc cggcaaacaa   5340
accaccgctg gtagcggtgg ttttttgtt tgcaagcagc agattacgcg cagaaaaaaa    5400
ggatctcaag aagatccttt gatcttttct acggggtctg acgctcagtg gaacgaaaac   5460
tcacgttaag ggattttggt catgagatta tcaaaaagga tcttcaccta gatccttta    5520 aattaaaaat gaagttttaa atcaatctaa agtatatatg agtaaacttg gtctgacagt   5580
taccaatgct taatcagtga ggcacctatc tcagcgatct gtctatttcg ttcatccata   5640
gttgcctgac tccccgtcgt gtagataact acgatacggg agggcttacc atctggcccc   5700
agtgctgcaa tgataccgcg agacccacgc tcaccggctc cagatttatc agcaataaac   5760
cagccagccg gaagggccga gcgcagaagt ggtcctgcaa ctttatccgc ctccatccag   5820
tctattaatt gttgccggga agctagagta agtagttcgc cagttaatag tttgcgcaac   5880
gttgttgcca ttgctacagg catcgtggtg tcacgctcgt cgtttggtat ggcttcattc   5940
agctccggtt cccaacgatc aaggcgagtt acatgatccc ccatgttgtg caaaaaagcg   6000
gttagctcct tcggtcctcc gatcgttgtc agaagtaagt tggccgcagt gttatcactc   6060
atggttatgg cagcactgca taattctctt actgtcatgc catccgtaag atgcttttct   6120
gtgactggtg agtactcaac caagtcattc tgagaatagt gtatgcggcg accgagttgc   6180
tcttgcccgg cgtcaatacg ggataatacc gcgccacata gcagaacttt aaaagtgctc   6240
atcattggaa aacgttcttc ggggcgaaaa ctctcaagga tcttaccgct gttgagatcc   6300
agttcgatgt aacccactcg tgcacccaac tgatcttcag catctttac tttcaccagc     6360 gtttctgggt gagcaaaaac aggaaggcaa aatgccgcaa aaaagggaat aagggcgaca   6420
cggaaatgtt gaatactcat actcttcctt tttcaatatt attgaagcat ttatcagggt   6480
tattgtctca tgagcggata catatttgaa tgtatttaga aaaataaaca atagggggtt   6540
ccgcgcacat ttccccgaaa agtgccacct aaattgtaag cgttaatatt ttgttaaaat   6600
tcgcgttaaa ttttgttaa atcagctcat tttttaacca ataggccgaa atcggcaaaa   6660
tcccttataa atcaaaagaa tagaccgaga tagggttgag tgttgttcca gtttggaaca   6720
agagtccact attaaagaac gtggactcca acgtcaaagg gcgaaaaacc gtctatcagg   6780
gcgatggccc actacgtgaa ccatcaccct aatcaagttt tttggggtcg aggtgccgta   6840
aagcactaaa tcggaaccct aaagggagcc ccgatttag agcttgacgg ggaaagccgg   6900
cgaacgtggc gagaaaggaa gggaagaaag cgaaaggagc gggcgctagg gcgctggcaa   6960
gtgtagcggt cacgctgcgc gtaaccacca cacccgccgc gcttaatgcg ccgctacagg   7020
gcgcgtccca ttcgccattc aggctgcgca actgttggga agggcgatcg gtgcgggcct   7080
cttcgctatt acgccagctg gcgaaagggg gatgtgctgc aaggcgatta agttgggtaa   7140
cgccaggggt ttcccagtca cgacgttgta aaacgacggc cagtgagcgc gcgtaatacg   7200
actcactata gggcgaattg ggtaccgggc cccccctcga tcgaggtcga cggtatcggg   7260
```

```
ggagctcgca gggtctccat tttgaagcgg gaggtttgaa cgcgcagccg ccatgccggg    7320
gttttacgag attgt                                                     7335

<210> SEQ ID NO 18
<211> LENGTH: 22
<212> TYPE: DNA
<213> ORGANISM: Artificial
<220> FEATURE:
<223> OTHER INFORMATION: Forward primer

<400> SEQUENCE: 18
tacataactt acggtaaatg gc                                             22

<210> SEQ ID NO 19
<211> LENGTH: 21
<212> TYPE: DNA
<213> ORGANISM: Artificial
<220> FEATURE:
<223> OTHER INFORMATION: Reverse primer

<400> SEQUENCE: 19
aaagtcccta ttggcgttac t                                              21
```